United States Patent
Kendirgi et al.

(10) Patent No.: US 11,591,274 B2
(45) Date of Patent: *Feb. 28, 2023

(54) DEFINED MICROBIAL COMPOSITIONS

(71) Applicant: AMVAC Chemical Corporation, Newport Beach, CA (US)

(72) Inventors: Frederic Kendirgi, Woodland, CA (US); Xing Liang Liu, Lake Oswego, OR (US); D. Ry Wagner, Pleasant Hill, OR (US); Sung-Yong H. Yoon, Lake Oswego, OR (US)

(73) Assignee: AMVAC Chemical Corporation, Newport Beach, CA (US)

(*) Notice: Subject to any disclaimer, the term of this patent is extended or adjusted under 35 U.S.C. 154(b) by 522 days.

This patent is subject to a terminal disclaimer.

(21) Appl. No.: 16/328,597

(22) PCT Filed: Aug. 30, 2017

(86) PCT No.: PCT/US2017/049326
§ 371 (c)(1),
(2) Date: Feb. 26, 2019

(87) PCT Pub. No.: WO2018/045004
PCT Pub. Date: Mar. 8, 2018

(65) Prior Publication Data
US 2019/0183131 A1    Jun. 20, 2019

Related U.S. Application Data

(60) Provisional application No. 62/381,441, filed on Aug. 30, 2016.

(51) Int. Cl.
| | | |
|---|---|---|
| C05F 11/08 | (2006.01) |
| C12N 1/20 | (2006.01) |
| C05F 1/00 | (2006.01) |
| A01N 63/10 | (2020.01) |
| A01N 63/20 | (2020.01) |
| A01N 63/22 | (2020.01) |
| A01N 63/25 | (2020.01) |
| A01N 63/27 | (2020.01) |
| A01N 63/28 | (2020.01) |
| C12R 1/01 | (2006.01) |
| C12R 1/02 | (2006.01) |
| C12R 1/10 | (2006.01) |
| C12R 1/125 | (2006.01) |
| C12R 1/145 | (2006.01) |
| C12R 1/225 | (2006.01) |

(52) U.S. Cl.
CPC ............ *C05F 11/08* (2013.01); *A01N 63/10* (2020.01); *A01N 63/20* (2020.01); *A01N 63/22* (2020.01); *A01N 63/25* (2020.01); *A01N 63/27* (2020.01); *A01N 63/28* (2020.01); *C05F 1/002* (2013.01); *C12N 1/20* (2013.01); *C12N 1/205* (2021.05); *C12R 2001/01* (2021.05); *C12R 2001/02* (2021.05); *C12R 2001/10* (2021.05); *C12R 2001/125* (2021.05); *C12R 2001/145* (2021.05); *C12R 2001/225* (2021.05); *Y02A 40/10* (2018.01); *Y02A 40/20* (2018.01); *Y02P 20/145* (2015.11)

(58) Field of Classification Search
CPC .......... C05F 11/08; C05F 1/002; C12N 1/205; C12N 1/20; A01N 63/22; A01N 63/25; A01N 63/27; A01N 63/28; A01N 63/20; C12R 2001/02; C12R 2001/10; C12R 2001/125; C12R 2001/145; C12R 2001/225; Y02A 40/10; Y02A 40/20
See application file for complete search history.

(56) References Cited

U.S. PATENT DOCUMENTS

| | | | |
|---|---|---|---|
| 2,853,416 A * | 9/1958 | Kellog | .................... A01N 43/36 424/78.25 |
| 9,175,258 B2 | 11/2015 | Bywater-Ekegard et al. | |
| 10,954,173 B2 * | 3/2021 | Venkatramesh | .......... C05C 1/00 |
| 11,066,341 B2 * | 7/2021 | Yoon | ....................... A01N 63/22 |
| 2011/0151508 A1 * | 6/2011 | Lopez-Cervantes | ..... C12N 1/20 435/42 |
| 2012/0329135 A1 | 12/2012 | Lopez-Cervantes | |
| 2012/0329650 A1 | 12/2012 | Lopez-Cervantes | |
| 2013/0255338 A1 | 10/2013 | Lopez-Cervantes | |

FOREIGN PATENT DOCUMENTS

| | | | |
|---|---|---|---|
| CN | 105779344 A | 7/2016 | |
| WO | WO 2011/157747 | 12/2011 | |
| WO | WO-2011157747 A2 * | 12/2011 | ............. A01N 63/00 |
| WO | WO 2016/135698 | 9/2016 | |
| WO | WO 2016/135699 | 9/2016 | |
| WO | WO 2016/135700 | 9/2016 | |
| WO | WO 2017/131821 | 8/2017 | |

* cited by examiner

*Primary Examiner* — Lynn Y Fan
(74) *Attorney, Agent, or Firm* — Klarquist Sparkman, LLP

(57) ABSTRACT

Disclosed herein are compositions including cells of defined sets of microbial species (for example, 3, 16, 18, 19, 21, or 22 microbial species). Also disclosed are methods of using the microbial compositions that include contacting soil, plants, plant parts, or seeds with the composition. The microbial compositions are also used in methods of degrading biological materials, such as chitin-containing biological materials.

10 Claims, 4 Drawing Sheets

Specification includes a Sequence Listing.

SEQUENCE LISTING

```
<160> NUMBER OF SEQ ID NOS: 136

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
agrgtttgat cmtggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 2
ggttaccttg ttacgactt                                               19

<210> SEQ ID NO 3
<211> LENGTH: 1549
<212> TYPE: DNA
<213> ORGANISM: Bacillus megaterium

<400> SEQUENCE: 3
tcggagagtt tgatcctggc tcaggatgaa cgctggcggc gtgcctaata catgcaagtc     60
gagcgaactg attagaagct tgcttctatg acgttagcgg cggacgggtg agtaacacgt    120
```

```
gggcaacctg cctgtaagac tgggataact tcgggaaacc gaagctaata ccggatagga      180
tcttctcctt catgggagat gattgaaaga tggtttcggc tatcacttac agatgggccc      240
gcggtgcatt agctagttgg tgaggtaacg gctcaccaag gcaacgatgc atagccgacc      300
tgagagggtg atcggccaca ctgggactga gacacggccc agactcctac gggaggcagc      360
agtagggaat cttccgcaat ggacgaaagt ctgacggagc aacgccgcgt gagtgatgaa      420
ggctttcggg tcgtaaaact ctgttgttag ggaagaacaa gtacgagagt aactgctcgt      480
accttgacgg tacctaacca gaaagccacg gctaactacg tgccagcagc cgcggtaata      540
cgtaggtggc aagcgttatc cggaattatt gggcgtaaag cgcgcgcagg cggtttctta      600
agtctgatgt gaaagcccac ggctcaaccg tggagggtca ttggaaactg ggaacttga      660 gtgcagaaga gaaaagcgga attccacgtg tagcggtgaa atgcgtagag atgtggagga      720
acaccagtgg cgaaggcggc ttttggtct gtaactgacg ctgaggcgcg aaagcgtggg      780
gagcaaacag gattagatac cctggtagtc cacgccgtaa acgatgagtg ctaagtgtta      840
gagggtttcc gcccttagt gctgcagcta acgcattaag cactccgcct ggggagtacg      900
gtcgcaagac tgaaactcaa aggaattgac ggggcccgc acaagcggtg gagcatgtgg      960
tttaattcga agcaacgcga agaaccttac caggtcttga catcctctga caactctaga     1020
gatagagcgt tccccttcgg gggacagagt gacaggtggt gcatggttgt cgtcagctcg     1080
tgtcgtgaga tgttgggtta agtcccgcaa cgagcgcaac ccttgatctt agttgccagc     1140
atttagttgg gcactctaag gtgactgccg gtgacaaacc ggaggaaggt ggggatgacg     1200
tcaaatcatc atgccccta tgacctgggc tacacacgtg ctacaatgga tggtacaaag     1260
ggctgcaaga ccgcgaggtc aagccaatcc cataaaacca ttctcagttc ggattgtagg     1320
ctgcaactcg cctacatgaa gctggaatcg ctagtaatcg cggatcagca tgccgcggtg     1380
aatacgttcc cgggccttgt acacaccgcc cgtcacacca cgagagtttg taacacccga     1440
agtcggtgga gtaaccgtaa ggagctagcc gcctaaggtg gacagatga ttgggggtgaa     1500 gtcgtaacaa ggtagccgta tcggaaggtg cggctggatc acctccttt                 1549

<210> SEQ ID NO 4
<211> LENGTH: 1567
<212> TYPE: DNA
<213> ORGANISM: Lactobacillus casei/paracasei

<400> SEQUENCE: 4
tatgagagtt tgatcctggc tcaggatgaa cgctggcggc gtgcctaata catgcaagtc       60
gaacgagttc tcgttgatga tcggtgcttg caccgagatt caacatggaa cgagtggcgg      120
acgggtgagt aacacgtggg taacctgccc ttaagtgggg gataacattt ggaaacagat      180
gctaataccg catagatcca agaaccgcat ggttcttggc tgaaagatgg cgtaagctat      240
cgcttttgga tggacccgcg gcgtattagc tagttggtga ggtaacggct caccaaggcg      300
atgatacgta gccgaactga gaggttgatc ggccacattg gactgagaca cggcccaaa      360 ctcctacggg aggcagcagt agggaatctt ccacaatgga cgcaagtctg atggagcaac      420
gccgcgtgag tgaagaaggc tttcgggtcg taaaactctg ttgttggaga agaatggtcg      480
gcagagtaac tgttgtcggc gtgacggtat ccaaccagaa agccacggct aactacgtgc      540
cagcagccgc ggtaatacgt aggtggcaag cgttatccgg atttattggg cgtaaagcga      600
gcgcaggcgg tttttttaagt ctgatgtgaa agccctcggc ttaaccgagg aagcgcatcg      660
gaaactggga aacttgagtg cagaagagga cagtggaact ccatgtgtag cggtgaaatg      720
```

```
cgtagatata tggaagaaca ccagtggcga aggcggctgt ctggtctgta actgacgctg      780
aggctcgaaa gcatgggtag cgaacaggat tagataccct ggtagtccat gccgtaaacg      840
atgaatgcta ggtgttggag ggtttccgcc cttcagtgcc gcagctaacg cattaagcat      900
tccgcctggg gagtacgacc gcaaggttga aactcaaagg aattgacggg ggcccgcaca      960
agcggtggag catgtggttt aattcgaagc aacgcgaaga accttaccag gtcttgacat     1020
cttttgatca cctgagagat caggtttccc cttcggggga aaaatgacag gtggtgcatg     1080
gttgtcgtca gctcgtgtcg tgagatgttg ggttaagtcc cgcaacgagc gcaaccctta     1140
tgactagttg ccagcattta gttgggcact ctagtaagac tgccggtgac aaaccggagg     1200
aaggtgggga tgacgtcaaa tcatcatgcc ccttatgacc tgggctacac acgtgctaca     1260
atggatggta caacgagttg cgagaccgcg aggtcaagct aatctcttaa agccattctc     1320
agttcggact gtaggctgca actcgcctac acgaagtcgg aatcgctagt aatcgcggat     1380
cagcacgccg cggtgaatac gttcccgggc cttgtacaca ccgcccgtca ccatgaga     1440 gtttgtaaca cccgaagccg gtggcgtaac cctttttaggg agcgagccgt ctaaggtggg     1500
acaaatgatt agggtgaagt cgtaacaagg tagccgtagg agaacctgcg gctggatcac     1560
ctccttt                                                              1567

<210> SEQ ID NO 5
<211> LENGTH: 1510
<212> TYPE: DNA
<213> ORGANISM: Clostridium beijerinckii

<400> SEQUENCE: 5
tattgagagt ttgatcctgg ctcaggacga acgctggcgg cgtgcttaac acatgcaagt       60
cgagcgatga agttccttcg ggaatggatt agcggcggac gggtgagtaa cacgtgggta      120
acctgcctca tagaggggaa tagcctttcg aaaggaagat taataccgca taagattgta      180
gtgccgcatg gcatagcaat taaaggagta atccgctatg agatggaccc gcgtcgcatt      240
agctagttgg tgaggtaacg gctcaccaag gcgacgatgc gtagccgacc tgagagggtg      300
atcggccaca ttgggactga gacacggccc agactcctac gggaggcagc agtggggaat      360
attgcacaat gggggaaacc ctgatgcagc aacgccgcgt gagtgatgac ggtcttcgga      420
ttgtaaagct ctgtcttcag ggacgataat gacggtacct gaggaggaag ccacggctaa      480
ctacgtgcca gcagccgcgg taatacgtag gtggcaagcg ttgtccggat ttactgggcg      540
taaagggagc gtaggtggat atttaagtgg gatgtgaaat actcgggctt aacctgggtg      600
ctgcattcca aactggatat ctagagtgca ggagaggaaa gtagaattcc tagtgtagcg      660
gtgaaatgcg tagagattag gaagaatacc agtggcgaag cgactttctg gactgtaac      720 tgacactgag gctcgaaagc gtggggagca acaggatta gatacctgg tagtccacgc      780 cgtaaacgat gaatactagg tgtagggggt gtcatgacct ctgtgccgcc gctaacgcat      840
taagtattcc gcctggggag tacggtcgca agattaaaac tcaaaggaat tgacggggc      900 ccgcacaagc agcggagcat gtggtttaat tcgaagcaac gcgaagaacc ttacctagac      960
ttgacatctc ctgaattacc cttaatcggg gaagcccttc ggggcaggaa gacaggtggt     1020
gcatggttgt cgtcagctcg tgtcgtgaga tgttgggtta agtcccgcaa cgagcgcaac     1080
ccttattgtt agttgctacc atttagttga gcactctagc gagactgccc gggttaaccg     1140
ggaggaaggt ggggatgacg tcaaatcatc atgcccctta tgtctagggc tacacacgtg     1200
```

| | |
|---|---|
| ctacaatggc tggtacagag agatgctaaa ccgtgaggtg gagccaaact ttaaaaccag | 1260 |
| tctcagttcg gattgtaggc tgaaactcgc ctacatgaag ctggagttgc tagtaatcgc | 1320 |
| gaatcagaat gtcgcggtga atacgttccc gggccttgta caccgcccg tcacaccat | 1380 |
| gagagttggc aatacccaaa gttcgtgagc taacgcgcaa gcggggcagc gacctaaggt | 1440 |
| agggtcagcg attggggtga agtcgtaaca aggtagccgt aggagaacct gcggctggat | 1500 |
| cacctccttt | 1510 |

<210> SEQ ID NO 6
<211> LENGTH: 1485
<212> TYPE: DNA
<213> ORGANISM: Acetobacter pasteurianus

<400> SEQUENCE: 6

| | |
|---|---|
| cctgagagtt tgatcctggc tcagagcgaa cgctggcggc atgcttaaca catgcaagtc | 60 |
| gcacgaaggt ttcggcctta gtggcggacg ggtgagtaac gcgtaggtat ctatccatgg | 120 |
| gtgggggata cactgggaa actggtgcta ataccgcatg acacctgagg gtcaaaggcg | 180 |
| caagtcgcct gtggaggagc ctgcgtttga ttagctagtt ggtggggtaa aggcctacca | 240 |
| aggcgatgat caatagctgg tttgagagga tgatcagcca cactgggact gagacacggc | 300 |
| ccagactcct acgggaggca gcagtgggga atattggaca atgggggcaa ccctgatcca | 360 |
| gcaatgccgc gtgtgtgaag aaggtcttcg gattgtaaag cactttcgac ggggacgatg | 420 |
| atgacggtac ccgtagaaga agccccggct aacttcgtgc cagcagccgc ggtaatacga | 480 |
| aggggggctag cgttgctcgg aatgactggg cgtaaagggc gtgtaggcgg tttgtacagt | 540 |
| cagatgtgaa atccccgggc ttaacctggg agctgcattt gatacgtgca gactagagtg | 600 |
| tgagagaggg ttgtggaatt cccagtgtag aggtgaaatt cgtagatatt gggaagaaca | 660 |
| ccggtggcga aggcggcaac ctggctcatt actgacgctg aggcgcgaaa gcgtggggag | 720 |
| caaacaggat tagataccct ggtagtccac gctgtaaacg atgtgtgcta gatgttgggt | 780 |
| gacttagtca ttcagtgtcg cagttaacgc gttaagcaca ccgcctgggg agtacggccg | 840 |
| caaggttgaa actcaaagga attgacgggg cccgcacaa gcggtggagc atgtggttta | 900 |
| attcgaagca acgcgcagaa ccttaccagg gcttgaatgt agaggctgca agcagagatg | 960 |
| tttgtttccc gcaagggacc tctaacacag gtgctgcatg gctgtcgtca gctcgtgtcg | 1020 |
| tgagatgttg ggttaagtcc cgcaacgagc gcaacccta tctttagttg ccatcaggtt | 1080 |
| gggctgggca ctctagagag actgccggtg acaagccgga ggaaggtggg gatgacgtca | 1140 |
| agtcctcatg gcccttatgt cctgggctac acacgtgcta caatggcggt gacagtggga | 1200 |
| agctaggtgg tgacaccatg ctgatctcta aaagccgtct cagttcggat tgcactctgc | 1260 |
| aactcgagtg catgaaggtg gaatcgctag taatcgcgga tcagcatgcc gcggtgaata | 1320 |
| cgttcccggg ccttgtacac accgcccgtc acaccatggg agttggtttg accttaagcc | 1380 |
| ggtgagcgaa ccgcaaggac gcagccgacc acggtcgggt cagcgactgg ggtgaagtcg | 1440 |
| taacaaggta gccgtagggg aacctgcggc tggatcaccct cctttt | 1485 |

<210> SEQ ID NO 7
<211> LENGTH: 1571
<212> TYPE: DNA
<213> ORGANISM: Lactobacillus buchneri

<400> SEQUENCE: 7

| | |
|---|---|
| atgagagttt gatcctggct caggacgaac gctggcggcg tgcctaatac atgcaagtcg | 60 |

```
aacgcgtctc cgttaatgat tttaggtgct tgcacttgaa agatttaaca ttgagacgag    120
tggcgaactg gtgagtaaca cgtgggtaac ctgcccttga agtaggggat aacacttgga    180
aacaggtgct aataccgtat aacaaccaaa accacctggt tttggtttaa aagacggctt    240
cggctgtcac tttaggatgg acccgcggcg tattagcttg ttggtaaggt aacggcctac    300
caaggcgatg atacgtagcc gacctgagag ggtaatcggc cacattggga ctgagacacg    360
gcccaaactc ctacgggagg cagcagtagg gaatcttcca caatggacga agtctgatg    420 gagcaacgcc gcgtgagtga tgaagggttt cggctcgtaa aactctgttg ttggagaaga    480
acaggtgtca gagtaactgt tgacatcttg acggtatcca accagaaagc cacggctaac    540
tacgtgccag cagccgcggt aatacgtagg tggcaagcgt tgtccggatt tattgggcgt    600
aaagcgagcg caggcggttt tttaggtctg atgtgaaagc cttcggctta accgagaag    660 tgcatcggaa accgggagac ttgagtgcag aagaggacag tggaactcca tgtgtagcgg    720
tgaaatgcgt agatatatgg aagaacacca gtggcgaagg cggctgtctg gtctgtaact    780
gacgctgagg ctcgaaagca tgggtagcga acaggattag ataccctggt agtccatgcc    840
gtaaacgatg agtgctaagt gttggagggt ttccgcccct cagtgctgca gctaacgcat    900
taagcactcc gcctggggag tacgaccgca aggttgaaac tcaaaggaat tgacgggggc    960
ccgcacaagc ggtggagcat gtggtttaat tcgatgctac gcgaagaacc ttaccaggtc   1020
ttgacatctt ctgccaactt aagagattag gcgttccctt cggggacaga atgacaggtg   1080
gtgcatggtt gtcgtcagct cgtgtcgtga gatgttgggt taagtcccgc aacgagcgca   1140 accttattg ttagttgcca gcattcagtt gggcactcta gcaagactgc cggtgacaaa   1200
ccggaggaag gtggggatga cgtcaaatca tcatgcccct tatgacctgg gctacacacg   1260
tgctacaatg gacggtacaa cgagtcgcga accgcgagg tcaagctaat ctcttaaagc   1320
cgttctcagt tcggattgta ggctgcaact cgcctacatg aagttggaat cgctagtaat   1380
cgtggatcag catgccacgg tgaatacgtt cccgggcctt gtacacaccg cccgtcacac   1440
catgagagtt tgtaacaccc aaagccggtg aggtaacctt cggggaccag ccgtctaagg   1500
tggggcagat gattagggtg aagtcgtaac aaggtagccg taggagaacc tgcggctgga   1560
tcacctcctt t                                                         1571
```

<210> SEQ ID NO 8
<211> LENGTH: 1548
<212> TYPE: DNA
<213> ORGANISM: Bacillus subtilis

<400> SEQUENCE: 8

```
atcggagagt ttgatcctgg ctcaggacga acgctggcgg cgtgcctaat acatgcaagt     60
cgagcggaca gatgggagct tgctccctga tgttagcggc ggacgggtga gtaacacgtg    120
ggtaacctgc ctgtaagact gggataactc cgggaaaccg gggctaatac cggatggttg    180
tttgaaccgc atggttcaaa cataaaaggt ggcttcggct accacttaca gatggacccg    240
cggcgcatta gctagttggt gaggtaacgg ctcaccaagg caacgatgcg tagccgacct    300
gagagggtga tcggccacac tgggactgag acacggccca gactcctacg ggaggcagca    360
gtagggaatc ttccgcaatg gacgaaagtc tgacggagca acgccgcgtg agtgatgaag    420
gttttcggat cgtaaagctc tgttgttagg gaagaacaag taccgttcga ataggccggt    480
accttgacgg tacctaacca gaaagccacg gctaactacg tgccagcagc cgcggtaata    540
```

-continued

```
cgtaggtggc aagcgttgtc cggaattatt gggcgtaaag ggctcgcagg cggtttctta      600
agtctgatgt gaaagccccc ggctcaaccg gggagggtca ttggaaactg ggaacttga       660 gtgcagaaga ggagagtgga attccacgtg tagcggtgaa atgcgtagag atgtggagga     720
acaccagtgg cgaaggcgac tctctggtct gtaactgacg ctgaggagcg aaagcgtggg     780
gagcgaacag gattagatac cctggtagtc cacgccgtaa acgatgagtg ctaagtgtta    840
gggggtttcc gccccttagt gctgcagcta acgcattaag cactccgcct ggggagtacg     900
gtcgcaagac tgaaactcaa aggaattgac ggggcccgc acaagcggtg gagcatgtgg     960
tttaattcga agcaacgcga agaaccttac caggtcttga catcctctga caatcctaga    1020
gataggacgt ccccttcggg ggcagagtga caggtggtgc atggttgtcg tcagctcgtg    1080
tcgtgagatg ttgggttaag tcccgcaacg agcgcaaccc ttgatcttag ttgccagcat    1140
tcagttgggc actctaaggt gactgccggt gacaaaccgg aggaaggtgg ggatgacgtc    1200
aaatcatcat gccccttatg acctgggcta cacacgtgct acaatggaca gaacaaaggg    1260
cagcgaaacc gcgaggttaa gccaatccca caaatctgtt ctcagttcgg atcgcagtct    1320
gcaactcgac tgcgtgaagc tggaatcgct agtaatcgcg gatcagcatg ccgcggtgaa    1380
tacgttcccg ggccttgtac acaccgcccg tcacaccacg agagtttgta acacccgaag    1440
tcggtgaggt aacctttag gagccagccg ccgaaggtgg gacagatgat tgggtgaag     1500 tcgtaacaag gtagccgtat cggaaggtgc ggctggatca cctccttt                 1548
```

<210> SEQ ID NO 9
<211> LENGTH: 1552
<212> TYPE: DNA
<213> ORGANISM: Paenibacillus cookii

<400> SEQUENCE: 9

```
cttgagagt ttgatcctgg ctcaggacga acgctggcgg cgtgcctaat acatgcaagt      60
cgagcggagt tgatggggag cttgctctcc tgagacttag cggcggacgg gtgagtaaca     120
cgtaggcaac ctgcccgtaa gaccgggata actaccggaa acggtagcta ataccggata    180
atttatcgct tcgcatggag cggtaatgaa agacggagca atctgtcact tacggatggg    240
cctgcggcgc attagctagt tggtgaggta acggctcacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc caggaagaa cgtcgggtag agtaactgct     480
atccgagtga cggtacctga aagaaagcc ccggctaact acgtgccagc agccgcggta     540
atacgtaggg ggcaagcgtt gtccggaatt attgggcgta aagcgcgcgc aggcggtcac    600
ttaagtctgg tgtttaaggc tagggctcaa ctctagttcg cactggaaac tgggtgactt    660
gagtgcagaa gaggaaagtg gaattccacg tgtagcggtg aaatgcgtag agatgtggag    720
gaacaccagt ggcgaaggcg actttctggg ctgtaactga cgctgaggcg cgaaagcgtg    780
gggagcaaac aggattagat accctggtag tccacgccgt aaacgatgaa tgctaggtgt    840
taggggtttc gataccttg gtgccgaagt taacacatta gcattccgc ctggggagta      900 cggtcgcaag actgaaactc aaaggaattg acggggaccc gcacaagcag tggagtatgt    960
ggtttaattc gaagcaacgc gaagaacctt accaggtctt gacatcctct gaatcctct     1020 agagatagag cgccttcg ggacagagga gacaggtggt gcatggttgt cgtcagctcg     1080
tgtcgtgaga tgttgggtta agtcccgcaa cgagcgcaac ccttgatttt agttgccagc    1140
```

-continued

```
acattaaggt gggcactcta gaatgactgc cggtgacaaa ccggaggaag gcggggatga    1200
cgtcaaatca tcatgcccct tatgacctgg gctacacacg tactacaatg gccagtacaa    1260
cgggaagcga agtcgcgaga cggagccaat cctatcaaag ctggtctcag ttcggattgc    1320
aggctgcaac ccgcctgcat gaagtcggaa ttgctagtaa tcgcggatca gcatgccgcg    1380
gtgaatacgt tcccgggtct tgtacacacc gcccgtcaca ccacgagagt ttacaacacc    1440
cgaagtcggt ggggtaaccg caaggagcca gccgccgaag gtggggtaga tgattggggt    1500
gaagtcgtaa caaggtagcc gtatcggaag gtgcggctgg atcacctcct tt            1552
```

<210> SEQ ID NO 10
<211> LENGTH: 1554
<212> TYPE: DNA
<213> ORGANISM: Lactobacillus vini

<400> SEQUENCE: 10

```
aatgagagtt tgatcctggc tcaggacgaa cgctggcggc gtgcctaata catgcaagtc     60
gaacgagact ttttatttga tgcttgcatc tttaaaaag ttgagtggcg aacgggtgag     120
taacacgtgg gtaacctgcc ttaaagtggg ggataacact tggaaacagg tgctaatacc    180
gcataaccat caaaaccgcc tggttttgat gttaaagatg gttctgctat cgctttaaga    240
tggacccgcg gcgtattagc tagttggtga ggtaacggct accaaggca atgatacgta     300 gccgaactga gaggttgatc ggccacattg gactgagac acggcccaaa ctcctacggg     360
aggcagcagt agggaatctt tcacaatgga cgaaagtctg atggagcaac gccgcgtgag    420
tgaagaaggt tttcggatcg taaaactctg ttgtcagaga gaacgtgtg tgagagtaac    480 tgttcacgca gtgacggtat ctgaccagaa agtcacggct aactacgtgc cagcagccgc    540
ggtaatacgt aggtggcaag cgttgtccgg atttattggg cgtaaaggga acgcaggcgg    600
tcttttaagt ctgatgtgaa agccttcggc ttaaccgaag tcgggcattg gaaactggga    660
gacttgagtg cagaagagga gagtggaact ccatgtgtag cggtgaaatg cgtagatata    720
tggaagaaca ccagtggcga aagcggctct ctggtctgta actgacgctg aggttcgaaa    780
gcgtgggtag caaacaggat tagataccct ggtagtccac gccgtaaacg atgaatgcta    840
agtgttggag ggtttccgcc cttcagtgcc gcagctaacg cattaagcat tccgcctggg    900
gagtacgatc gcaagattga aactcaaagg aattgacggg ggcccgcaca gcggtggag    960 catgtggttt aattcgaagc aacgcgaaga accttaccag gtcttgacat cttttgctaa    1020
cctgagagat caggtgttcc cttcggggac aaaatgacag gtggtgcatg gttgtcgtca    1080
gctcgtgtcg tgagatgttg ggttaagtcc cgcaacgagc gcaacccttt a ttgttagttg    1140 ccagcattta gttgggcact ctaacgagac tgccggtgac aaaccggagg aaggtgggga    1200
tgacgtcaaa tcatcatgcc ccttatgacc tgggctacac acgtgctaca atggacggta    1260
caacgagtcg caagaccgcg aggtcaagct aatctctgaa aaccgttctc agttcggatt    1320
gcaggctgca actcgcctgc atgaagtcgg aatcgctagt aatcgcggat cagcatgccg    1380
cggtgaatac gttcccgggc cttgtacaca ccgcccgtca caccatgaga gtttgtaaca    1440
cccaaagccg gtggggtaac ctttgggagc cagccgtcta aggtgggaca gatgattggg    1500
gtgaagtcgt aacaaggtag ccgtaggaga acctgcggct ggatcacctc cttt            1554
```

<210> SEQ ID NO 11
<211> LENGTH: 1549
<212> TYPE: DNA

<213> ORGANISM: Bacillus licheniformis

<400> SEQUENCE: 11

```
catggagagt tgatcctgg ctcaggacga acgctggcgg cgtgcctaat acatgcaagt      60
cgagcggacc gacgggagct tgctccctta ggtcagcggc ggacgggtga gtaacacgtg     120
ggtaacctgc ctgtaagact gggataactc cgggaaaccg gggctaatac cggatgcttg    180
attgaaccgc atggttccaa tcataaaagg tggcttttag ctaccactta cagatggacc    240
cgcggcgcat tagctagttg gtgaggtaac ggctcaccaa ggcgacgatg cgtagccgac    300
ctgagagggt gatcggccac actgggactg agacacggcc cagactccta cgggaggcag    360
cagtagggaa tcttccgcaa tggacgaaag tctgacggag caacgccgcg tgagtgatga    420
aggttttcgg atcgtaaaac tctgttgtta gggaagaaca agtaccgttc gaatagggcg    480
gcaccttgac ggtacctaac cagaaagcca cggctaacta cgtgccagca gccgcggtaa    540
tacgtaggtg gcaagcgttg tccggaatta ttgggcgtaa agcgcgcgca ggcggttttct   600
taagtctgat gtgaaagccc ccggctcaac cggggagggt cattggaaac tggggaactt    660
gagtgcagaa gaggagagtg gaattccacg tgtagcggtg aaatgcgtag agatgtggag    720
gaacaccagt ggcgaaggcg actctctggt ctgtaactga cgctgaggcg cgaaagcgtg    780
gggagcgaac aggattagat accctggtag tccacgccgt aaacgatgag tgctaagtgt    840
tagagggttt ccgcccttta gtgctgcagc aaacgcatta agcactccgc ctggggagta    900
cggtcgcaag actgaaactc aaaggaattg acggggcccc gcacaagcgg tggagcatgt    960
ggtttaattc gaagcaacgc gaagaacctt accaggtctt gacatcctct gacaacccta   1020
gagatagggc ttccccttcg ggggcagagt gacaggtggt gcatggttgt cgtcagctcg   1080
tgtcgtgaga tgttgggtta agtcccgcaa cgagcgcaac ccttgatctt agttgccagc   1140
attcagttgg gcactctaag gtgactgccg gtgacaaacc ggaggaaggt ggggatgacg   1200
tcaaatcatc atgccccctta tgacctgggc tacacacgtg ctacaatggg cagaacaaag  1260
ggcagcgaag ccgcgaggct aagccaatcc cacaaatctg ttctcagttc ggatcgcagt   1320
ctgcaactcg actgcgtgaa gctggaatcg ctagtaatcg cggatcagca tgccgcggtg   1380
aatacgttcc cgggccttgt acacaccgcc cgtcacacca cgagagtttg taacacccga   1440
agtcggtgag gtaaccttt ggagccagcc gccgaaggtg gacagatga ttggggtgaa     1500
gtcgtaacaa ggtagccgta tcggaaggtg cggctggatc acctccttt              1549
```

<210> SEQ ID NO 12
<211> LENGTH: 1553
<212> TYPE: DNA
<213> ORGANISM: Paenibacillus lautus

<400> SEQUENCE: 12

```
attggagagt tgatcctgg ctcaggacga acgctggcgg cgtgcctaat acatgcaagt      60
cgagcggact tgatggagtg cttgcactcc tgaaggttag cggcggacgg gtgagtaaca    120
cgtaggcaac ctgccctcaa gactgggata actaccggaa acggtagcta ataccggata    180
atttattttg cagcattgtg aaataatgaa aggcggagca atctgtcact tgaggatggg    240
cctgcggcgc attagctagt tggtggggta acggcccacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc caaggaagaa cgtcttctag agtaactgct    480
```

```
aggagagtga cggtacttga gaagaaagcc ccggctaact acgtgccagc agccgcggta      540
atacgtaggg ggcaagcgtt gtccggaatt attgggcgta aagcgcgcgc aggcggttct      600
ttaagtctgg tgtttaaacc cgaggctcaa cttcgggtcg cactggaaac tgggggaactt    660 gagtgcagaa gaggagagtg gaattccacg tgtagcggtg aaatgcgtag atatgtggag     720
gaacaccagt ggcgaaggcg actctctggg ctgtaactga cgctgaggcg cgaaagcgtg     780
gggagcaaac aggattagat accctggtag tccacgccgt aaacgatgaa tgctaggtgt    840
taggggtttc gataccctttg gtgccgaagt taacacatta agcattccgc ctggggagta   900
cggtcgcaag actgaaactc aaaggaattg acggggaccc gcacaagcag tggagtatgt    960
ggtttaattc gaagcaacgc gaagaacctt accaagtctt gacatccctc tgaatcctct    1020
agagatagag gcggccttcg ggacagaggt gacaggtggt gcatggttgt cgtcagctcg    1080
tgtcgtgaga tgttgggtta agtcccgcaa cgagcgcaac ccttgatttt agttgccagc    1140
acttcgggtg ggcactctag aatgactgcc ggtgacaaac cggaggaagg cggggatgac   1200
gtcaaatcat catgcccctt atgacttggg ctacacacgt actacaatgg ctggtacaac    1260
gggaagcgaa gccgcgaggt ggagccaatc ctataaaagc cagtctcagt tcggattgca    1320
ggctgcaact cgcctgcatg aagtcggaat tgctagtaat cgcggatcag catgccgcgg    1380
tgaatacgtt cccgggtctt gtacacaccg cccgtcacac cacgagagtt tacaacaccc   1440
gaagtcggtg ggtaacccct aggggagcc agccgccgaa ggtggggtag atgattgggg    1500
tgaagtcgta acaaggtagc cgtatcggaa ggtgcggctg gatcacctcc ttt           1553

<210> SEQ ID NO 13
<211> LENGTH: 1561
<212> TYPE: DNA
<213> ORGANISM: Oceanobacillus oncorhynchi

<400> SEQUENCE: 13
ttatggagag tttgatcttg gctcaggacg aacgctggcg gcgtgcctaa tacatgcaag      60
tcgagcgcgg gaagcgaacg gaactcttcg gagggaagtt cgtggaacga gcggcggacg    120
ggtgagtaac acgtaggcaa cctgcctgta agactggat aactcgcgga aacgcgagct    180
aataccggat aacactttct atcacctgat ggaaagttga aggcggcttt tgctgtcac    240 ttacagatgg gcctgcggcg cattagctag ttggtgaggt aacggctcac caaggcgacg   300
atgcgtagcc gacctgagag ggtgatcggc cacactggga ctgagacacg gcccagactc    360
ctacgggagg cagcagtagg gaatcttccg caatggacga aagtctgacg gagcaacgcc    420
gcgtgagtga tgaaggtttt cggatcgtaa aactctgttg tcaggaagaa acaagtacga    480
tagtaactga tcgtaccttg acggtacctg accagaaagc cacggctaac tacgtgccag   540
cagccgcggt aatacgtagg tggcaagcgt tgtccggaat tattgggcgt aaagcgctcg    600
caggcggttc tttaagtctg atgtgaaatc ttgcggctca accgcaaacg tgcattggaa    660
actggaggac ttgagtgcag aagaggagag tggaattcca cgtgtagcgg tgaaatgcgt    720
agagatgtgg aggaacacca gtggcgaagg cgactctctg gtctgtaact gacgctgagg    780
agcgaaagcg tggggagcga acaggattag ataccctggt agtccacgcc gtaaacgatg    840
agtgctaggt gttaggggg ttccgccccct tagtgctgaa gttaacgcat taagcactcc   900
gcctggggag tacggccgca aggctgaaac tcaaaagaat tgacgggac ccgcacaagc    960 ggtggagcat gtggtttaat tcgaagcaac gcgaagaacc ttaccaggtc ttgacatcct   1020
```

```
ttgaccgctc tagagataga gttttcccctt cggggacaaa gtgacaggtg gtgcatggtt   1080
gtcgtcagct cgtgtcgtga gatgttgggt taagtcccgc aacgagcgca acccttaatc   1140
ttagttgcca gcatttagtt gggcactcta aggtgactgc cggtgacaaa ccggaggaag   1200
gtggggatga cgtcaaatca tcatgcccct tatgacctgg gctacacacg tgctacaatg   1260
gacggaacaa agggaagcga acccgcgagg tccagcaaat cccataaaac cgttctcagt   1320
tcggattgca ggctgcaact cgcctgcatg aagccggaat cgctagtaat cgcggatcag   1380
catgccgcgg tgaatacgtt cccgggtctt gtacacaccg cccgtcacac cacgagagtt   1440
cgtaacaccc gaagtcggtg aggtaacctt tggagccag ccgccgaagg tgggacgaat   1500
gattggggtg aagtcgtaac aaggtagccg tatcggaagg tgcggctgga tcacctcctt   1560
t                                                                  1561

<210> SEQ ID NO 14
<211> LENGTH: 1548
<212> TYPE: DNA
<213> ORGANISM: Bacillus amyloliquefaciens

<400> SEQUENCE: 14
atcggagagt ttgatcctgg ctcaggacga acgctggcgg cgtgcctaat acatgcaagt     60
cgagcggaca gatgggagct tgctccctga tgttagcggc ggacgggtga gtaacacgtg    120
ggtaacctgc ctgtaagact gggataactc cgggaaaccg gggctaatac cggatggttg    180
tctgaaccgc atggttcaga cataaaaggt ggcttcggct accacttaca gatggacccg    240
cggcgcatta gctagttggt gaggtaacgg ctcaccaagg cgacgatgcg tagccgacct    300
gagagggtga tcggccacac tgggactgag acacggccca gactcctacg ggaggcagca    360
gtagggaatc ttccgcaatg gacgaaagtc tgacggagca acgccgcgtg agtgatgaag    420
gttttcggat cgtaaagctc tgttgttagg gaagaacaag tgccgttcaa atagggcggc    480
accttgacgt tacctaacca gaaagccacg gctaactacg tgccagcagc cgcggtaata    540
cgtaggtggc aagcgttgtc cggaattatt gggcgtaaag ggctcgcagg cggtttctta    600
agtctgatgt gaaagccccc ggctcaaccg ggagggtca ttggaaactg ggaacttga     660
gtgcagaaga ggagagtgga attccacgtg tagcggtgaa atgcgtagag atgtggagga    720
acaccagtgg cgaaggcgac tctctggtct gtaactgacg ctgaggagcg aaagcgtggg    780
gagcgaacag gattagatac cctggtagtc cacgccgtaa acgatgagtg ctaagtgtta    840
gggggtttcc gccccttagt gctgcagcta acgcattaag cactccgcct ggggagtacg    900
gtcgcaagac tgaaactcaa aggaattgac ggggcccgc acaagcggtg gagcatgtgg    960
tttaattcga agcaacgcga agaacctta caggtcttga catcctctga caatcctaga   1020
gataggacgt ccccttcggg ggcagagtga caggtggtgc atggttgtcg tcagctcgtg   1080
tcgtgagatg ttgggttaag tcccgcaacg agcgcaaccc ttgatcttag ttgccagcat   1140
tcagttgggc actctaaggt gactgccggt gacaaaccgg aggaaggtgg ggatgacgtc   1200
aaatcatcat gccccttatg acctgggcta cacacgtgct acaatggaca gaacaaaggg   1260
cagcgaaacc gcgaggttaa gccaatccca caaatctgtt ctcagttcgg atcgcagtct   1320
gcaactcgac tgcgtgaagc tggaatcgct agtaatcgcg gatcagcatg ccgcggtgaa   1380
tacgttcccg ggccttgtac acaccgcccg tcacaccacg agagtttgta acacccgaag   1440
tcggtgaggt aacctttatg gagccagccg ccgaaggtgg gacagatgat tggggtgaag   1500
tcgtaacaag gtagccgtat cggaaggtgc ggctggatca cctcccttt              1548
```

<210> SEQ ID NO 15
<211> LENGTH: 1547
<212> TYPE: DNA
<213> ORGANISM: Bacillus sp.

<400> SEQUENCE: 15

```
attggagagt tgatcctgg ctcaggacga acgctggcgg cgtgcctaat acatgcaagt      60
cgagcgaatc tgagggagct tgctcccaaa gattagcggc ggacgggtga gtaacacgtg     120
ggcaacctgc ctgtaagact gggataactc cgggaaaccg gggctaatac cggataatat     180
ctatttatac atataattag attgaaagat ggttctgcta tcacttacag atgggcccgc     240
ggcgcattag ctagttggtg aggtaacggc tcaccaaggc gacgatgcgt agccgacctg     300
agagggtgat cggccacact gggactgaga cacggcccag actcctacgg gaggcagcag     360
tagggaatct tccgcaatgg acgaaagtct gacggagcaa cgccgcgtga gtgatgaagg     420
ttttcggatc gtaaaactct gttgttaggg aagaacaagt atcggagtaa ctgccggtac     480
cttgacggta cctaaccaga aagccacggc taactacgtg ccagcagccg cggtaatacg     540
taggtggcaa gcgttgtccg gaattattgg gcgtaaagcg cgcgcaggcg gttccttaag     600
tctgatgtga aagcccacgg ctcaaccgtg agggtcatt ggaaactggg gaacttgagt     660
gcagaagagg aaagtggaat tccaagtgta gcggtgaaat gcgtagagat ttggaggaac     720
accagtggcg aaggcgactt tctggtctgt aactgacgct gaggcgcgaa agcgtgggga     780
gcaaacagga ttagataccc tggtagtcca cgccgtaaac gatgagtgct aagtgttaga     840
gggtttccgc cctttagtgc tgcagcaaac gcattaagca ctccgcctgg ggagtacgac     900
cgcaaggttg aaactcaaag gaattgacgg gggcccgcac aagcggtgga gcatgtggtt     960
taattcgaag caacgcgaag aaccttacca ggtcttgaca tcctctgaca atcctagaga    1020
taggactttc cccttcgggg gacagagtga caggtggtgc atggttgtcg tcagctcgtg    1080
tcgtgagatg ttgggttaag tcccgcaacg agcgcaaccc ttgatcttag ttgccagcat    1140
ttagttgggc actctaaggt gactgccggt gacaaaccgg aggaaggtgg ggatgacgtc    1200
aaatcatcat gccccttatg acctgggcta cacacgtgct acaatggatg gtacaaaggg    1260
ctgcaagacc gcgaggttta gccaatccca taaaaccatt ctcagttcgg attgtaggct    1320
gcaactcgcc tacatgaagc cggaatcgct agtaatcgcg gatcagcatg ccgcggtgaa    1380
tacgttcccg ggccttgtac acaccgcccg tcacaccacg agagtttgta cacccgaag     1440
tcggtggggt aaccttttgg agccagccgc ctaaggtggg acagatgatt ggggtgaagt    1500
cgtaacaagg tagccgtatc ggaaggtgcg gctggatcac ctcctttt                 1547
```

<210> SEQ ID NO 16
<211> LENGTH: 1533
<212> TYPE: DNA
<213> ORGANISM: Pseudomonas putida

<400> SEQUENCE: 16

```
ctgaagagtt tgatcatggc tcagattgaa cgctggcggc aggcctaaca catgcaagtc      60
gagcggatga aagagcttg ctcttcgatt cagcggcgga cgggtgagta atgcctagga     120
atctgcctgg tagtggggga caacgtttcg aaaggaacgc taataccgca tacgtcctac     180
gggagaaagc aggggacctt cgggccttgc gctatcagat gagcctaggt cggattagct     240
agttggtgag gtaatggctc accaaggcga cgatccgtaa ctggtctgag aggatgatca     300
```

```
gtcacactgg aactgagaca cggtccagac tcctacggga ggcagcagtg gggaatattg    360
gacaatgggc gaaagcctga tccagccatg ccgcgtgtgt gaagaaggtc ttcggattgt    420
aaagcacttt aagttgggag gaagggcatt aacctaatac gttagtgttt tgacgttacc    480
gacagaataa gcaccggcta actctgtgcc agcagccgcg gtaatacaga gggtgcaagc    540
gttaatcgga attactgggc gtaaagcgcg cgtaggtggt tgttaagtt ggatgtgaaa     600 gccccgggct caacctggga actgcatcca aaactggcaa gctagagtac ggtagagggt    660
ggtggaattt cctgtgtagc ggtgaaatgc gtagatatag gaaggaacac cagtggcgaa    720
ggcgaccacc tggactgata ctgacactga ggtgcgaaag cgtggggagc aaacaggatt    780
agataccctg gtagtccacg ccgtaaacga tgtcaactag ccgttggaat ccttgagatt    840
ttagtggcgc agctaacgca ttaagttgac cgcctgggga gtacggccgc aaggttaaaa    900
ctcaaatgaa ttgacggggg cccgcacaag cggtggagca tgtggtttaa ttcgaagcaa    960
cgcgaagaac cttaccaggc cttgacatgc agagaacttt ccagagatgg attggtgcct   1020
tcgggaactc tgacacaggt gctgcatggc tgtcgtcagc tcgtgtcgtg agatgttggg   1080
ttaagtcccg taacgagcgc aacccttgtc cttagttacc agcacgtaat ggtgggcact   1140
ctaaggagac tgccggtgac aaaccggagg aaggtgggga tgacgtcaag tcatcatggc   1200
ccttacggcc tgggctacac acgtgctaca atggtcggta cagagggttg ccaagccgcg   1260
aggtggagct aatctcacaa aaccgatcgt agtccggatc gcagtctgca actcgactgc   1320
gtgaagtcgg aatcgctagt aatcgcgaat cagaatgtcg cggtgaatac gttcccgggc   1380
cttgtacaca ccgcccgtca ccatgggagt ggggttgca ccagaagtag ctagtctaac   1440
cttcgggagg acggttacca cggtgtgatt catgactggg gtgaagtcgt aacaaggtag   1500
ccgtagggga acctgcggct ggatcacctc ctt                                1533
```

<210> SEQ ID NO 17
<211> LENGTH: 1533
<212> TYPE: DNA
<213> ORGANISM: Pseudomonas sp.

<400> SEQUENCE: 17

```
ctgaagagtt tgatcatggc tcagattgaa cgctggcggc aggcctaaca catgcaagtc     60
gagcggatga cgggagcttg ctccttgatt cagcggcgga cgggtgagta atgcctagga    120
atctgcctgg tagtggggga caacgtttcg aaaggaacgc taataccgca tacgtcctac    180
gggagaaagc aggggacctt cgggccttgc gctatcagat gagcctaggt cggattagct    240
agtaggtgag gtaatggctc acctaggcga cgatccgtaa ctggtctgag aggatgatca    300
gtcacactgg aactgagaca cggtccagac tcctacggga ggcagcagtg gggaatattg    360
gacaatgggc gaaagcctga tccagccatg ccgcgtgtgt gaagaaggtc ttcggattgt    420
aaagcacttt aagttgggag gaagggcagt aagctaatac cttgctgttt tgacgttacc    480
gacagaataa gcaccggcta actctgtgcc agcagccgcg gtaatacaga gggtgcaagc    540
gttaatcgga attactgggc gtaaagcgcg cgtaggtggt tcgttaagtt ggatgtgaaa    600
gccccgggct caacctggga actgcatcca aaactggcga gctagagtat ggtagagggt    660
ggtggaattt cctgtgtagc ggtgaaatgc gtagatatag gaaggaacac cagtggcgaa    720
ggcgaccacc tggactgata ctgacactga ggtgcgaaag cgtggggagc aaacaggatt    780
agataccctg gtagtccacg ccgtaaacga tgtcaactag ccgttggaat ccttgagatt    840
ttagtggcgc agctaacgca ttaagttgac cgcctgggga gtacggccgc aaggttaaaa    900
```

```
ctcaaatgaa ttgacggggg cccgcacaag cggtggagca tgtggtttaa ttcgaagcaa      960
cgcgaagaac cttaccaggc cttgacatgc agagaacttt ccagagatgg attggtgcct     1020
tcgggaactc tgacacaggt gctgcatggc tgtcgtcagc tcgtgtcgtg agatgttggg     1080
ttaagtcccg taacgagcgc aaccettgtc cttagttacc agcacgttat ggtgggcact     1140
ctaaggagac tgccggtgac aaaccggagg aaggtgggga tgacgtcaag tcatcatggc     1200
ccttacggcc tgggctacac acgtgctaca atggtcggta cagaggggttg ccaagccgcg     1260 aggtggagct aatctcacaa aaccgatcgt agtccggatc gcagtctgca actcgactgc     1320
gtgaagtcgg aatcgctagt aatcgcaaat cagaatgttg cggtgaatac gttcccgggc     1380
cttgtacaca ccgcccgtca ccatgggag tgggttgca ccagaagtag ctagtctaac     1440 cttcggggg acgttacca cggtgtgatt catgactggg gtgaagtcgt aacaaggtag     1500
ccgtagggga acctgcggct ggatcacctc ctt                                  1533

<210> SEQ ID NO 18
<211> LENGTH: 1523
<212> TYPE: DNA
<213> ORGANISM: Streptomyces griseus

<400> SEQUENCE: 18
acggagagtt tgatcctggc tcaggacgaa cgctggcggc gtgcttaaca catgcaagtc       60
gaacgatgaa gcctttcggg gtggattagt ggcgaacggg tgagtaacac gtgggcaatc      120
tgcccttcac tctgggacaa gccctggaaa cggggtctaa taccggataa cactctgtcc      180
cgcatgggac ggggttaaaa gctccggcgg tgaaggatga gcccgcggcc tatcagcttg      240
ttggtggggt aatggcctac caaggcgacg acgggtagcc ggcctgagag ggcgaccggc      300
cacactggga ctgagacacg gcccagactc ctacgggagg cagcagtggg gaatattgca      360
caatgggcga aagcctgatg cagcgacgcc gcgtgaggga tgacggcctt cgggttgtaa      420
acctctttca gcagggaaga agcgagagtg acggtacctg cagaagaagc gccggctaac      480
tacgtgccag cagccgcggt aatacgtagg gcgcaagcgt tgtccggaat tattgggcgt      540
aaagagctcg taggcggctt gtcacgtcgg atgtgaaagc ccggggctta accccgggtc      600
tgcattcgat acgggctagc tagagtgtgg taggggagat cggaattcct ggtgtagcgg      660
tgaaatgcgc agatatcagg aggaacaccg gtggcgaagg cggatctctg gccattact       720 gacgctgagg agcgaaagcg tggggagcga acaggattag ataccctggt agtccacgcc      780
gtaaacgttg ggaactaggt gttggcgaca ttccacgtcg tcggtgccgc agctaacgca      840
ttaagttccc cgcctgggga gtacggccgc aaggctaaaa ctcaaaggaa ttgacggggg      900
cccgcacaag cagcggagca tgtggcttaa ttcgacgcaa cgcgaagaac cttaccaagg      960
cttgacatat accggaaagc atcagagatg gtgcccccct tgtggtcggt atacaggtgg     1020
tgcatggctg tcgtcagctc gtgtcgtgag atgttgggtt aagtcccgca acgagcgcaa     1080
cccttgttct gtgttgccag catgcccttc ggggtgatgg ggactcacag gagactgccg     1140
gggtcaactc ggaggaaggt ggggacgacg tcaagtcatc atgccccctta tgtcttgggc     1200 tgcacacgtg ctacaatggc cggtacaatg agctgcgatg ccgcgaggcg gagcgaatct     1260
caaaaagccg gtctcagttc ggattggggt ctgcaactcg accccatgaa gtcggagttg     1320
ctagtaatcg cagatcagca ttgctgcggt gaatacgttc ccgggccttg tacacaccgc     1380
ccgtcacgtc acgaaagtcg gtaacacccg aagccggtgg cccaaccccct tgtgggaggg     1440
```

```
agctgtcgaa ggtgggactg gcgattggga cgaagtcgta acaaggtagc cgtaccggaa    1500
ggtgcggctg gatcacctcc ttt                                            1523

<210> SEQ ID NO 19
<211> LENGTH: 1553
<212> TYPE: DNA
<213> ORGANISM: Paenibacillus chibensis

<400> SEQUENCE: 19
cttggagagt ttgatcctgg ctcaggacga acgctggcgg cgtgcctaat acatgcaagt      60
cgagcggagt tgatgaggtg cttgcacctc tgatgcttag cggcggacgg gtgagtaaca     120
cgtaggtaac ctgcctgtaa gactgggata actaccggaa acggtagcta ataccggata     180
atttattttc tctcctgggg agataatgaa agacggagca atctgtcact tacagatggg     240
cctgcggcgc attagctagt tggtgaggta acggctcacc aaggcgacga tgcgtagccg     300
acctgagagg gtgaacggcc acactgggac tgagacacgg cccagactcc tacgggaggc     360
agcagtaggg aatcttccgc aatggacgaa agtctgacgg agcaacgccg cgtgagtgat     420
gaaggttttc ggatcgtaaa gctctgttgc agggaagaa cgtccggtag agtaactgct     480
accggagtga cggtacctga aagaaagcc cggctaact acgtgccagc agccgcggta     540
atacgtaggg ggcaagcgtt gtccggaatt attgggcgta aagcgcgcgc aggcggtcac     600
ttaagtctgg tgtttaaggc caaggctcaa ccttggttcg cactgaaac tgggtgactt     660 gagtgcagaa gaggagagtg gaattccacg tgtagcggtg aaatgcgtag atatgtggag     720
gaacaccagt ggcgaaggcg actctctggg ctgtaactga cgctgaggcg cgaaagcgtg     780
gggagcaaac aggattagat accctggtag tccacgccgt aaacgatgaa tgctaggtgt     840
taggggtttc gataccccttg gtgccgaagt taacacatta gcattccgc ctggggagta     900 cggtcgcaag actgaaactc aaaggaattg acggggaccc gcacaagcag tggagtatgt     960
ggtttaattc gaagcaacgc gaagaacctt accaagtctt gacatccctc tgaatcctct    1020
agagatagag gcggccttcg ggacagaggt gacaggtggt gcatggttgt cgtcagctcg    1080
tgtcgtgaga tgttgggtta agtcccgcaa cgagcgcaac ccttgatttt agttgccagc    1140
atttcggatg ggcactctag aatgactgcc ggtgacaaac cggaggaagg cggggatgac    1200
gtcaaatcat catgcccctt atgacttggg ctacacacgt actacaatgg ccagtacaac    1260
gggaagcgaa atcgcgagat ggagccaatc ctatcaaagc tggtctcagt tcggattgca    1320
ggctgcaacc cgcctgcatg aagtcggaat tgctagtaat cgcggatcag catgccgcgg    1380
tgaatacgtt cccgggtctt gtacacaccg cccgtcacac cacgagagtt tacaacaccc    1440
gaagtcggtg gggtaacccg caaggagcc agccgccgaa ggtggggtag atgattgggg    1500
tgaagtcgta acaaggtagc cgtatcggaa ggtgcggctg gatcacctcc ttt           1553

<210> SEQ ID NO 20
<211> LENGTH: 1550
<212> TYPE: DNA
<213> ORGANISM: Bacillus flexus

<400> SEQUENCE: 20
tcggagagtt tgatcctggc tcaggatgaa cgctggcggc gtgcctaata catgcaagtc      60
gagcgaactg attagaagct tgcttctatg acgttagcgg cggacgggtg agtaacacgt     120
gggcaacctg cctgtaagac tgggataact ccgggaaacc ggagctaata ccggataaca     180
ttttctcttg cataagagaa aattgaaaga tggtttcggc tatcacttac agatgggccc     240
```

```
gcggtgcatt agctagttgg tgaggtaacg gctcaccaag gcaacgatgc atagccgacc    300
tgagagggtg atcggccaca ctgggactga gacacggccc agactcctac gggaggcagc    360
agtagggaat cttccgcaat ggacgaaagt ctgacggagc aacgccgcgt gagtgatgaa    420
ggctttcggg tcgtaaaact ctgttgttag ggaagaacaa gtacaagagt aactgcttgt    480
accttgacgg tacctaacca gaaagccacg gctaactacg tgccagcagc cgcggtaata    540
cgtaggtggc aagcgttatc cggaattatt gggcgtaaag cgcgcgcagg cggtttctta    600
agtctgatgt gaaagcccac ggctcaaccg tgagggtca ttggaaactg ggaacttga     660 gtgcagaaga gaaaagcgga attccacgtg tagcggtgaa atgcgtagag atgtggagga    720
acaccagtgg cgaaggcggc tttttggtct gtaactgacg ctgaggcgcg aaagcgtggg    780
gagcaaacag gattagatac cctggtagtc cacgccgtaa acgatgagtg ctaagtgtta    840
gagggtttcc gcccttt agt gctgcagcta acgcattaag cactccgcct ggggagtacg    900
gtcgcaagac tgaaactcaa aggaattgac ggggcccgc acaagcggtg gagcatgtgg    960
tttaattcga agcaacgcga gaaccttac caggtcttga catcctctga caactctaga   1020
gatagagcgt tccccttcgg gggacagagt gacaggtggt gcatggttgt cgtcagctcg   1080
tgtcgtgaga tgttgggtta agtcccgcaa cgagcgcaac ccttgatctt agttgccagc   1140
atttagttgg gcactctaag gtgactgccg gtgacaaacc ggaggaaggt ggggatgacg   1200
tcaaatcatc atgccccta tgacctgggc tacacacgtg ctacaatgga tggtacaaag   1260
ggctgcaaga ccgcgaggtc aagccaatcc cataaaacca ttctcagttc ggattgtagg   1320
ctgcaactcg cctacatgaa gctggaatcg ctagtaatcg cggatcagca tgccgcggtg   1380
aatacgttcc cgggccttgt acacaccgcc cgtcacacca cgagagtttg taacacccga   1440
agtcggtggg gtaaccttta tggagccagc cgcctaaggt gggacagatg attggggtga   1500
agtcgtaaca aggtagccgt atcggaaggt gcggctggat caccctcttt              1550

<210> SEQ ID NO 21
<211> LENGTH: 1505
<212> TYPE: DNA
<213> ORGANISM: Clostridium pasteurianum

<400> SEQUENCE: 21
aattgagagt ttgatcctgg ctcaggacga acgctggcgg cgtgcttaac acatgcaagt     60
cgagcgagaa accttcgggt ttctagcggc ggacgggtga gtaacacgtg gtaacctgc    120 ctcaaagagg ggaatagcct cccgaaaggg agattaatac cgcataatat tacagcttcg    180
catgaagcag taattaaagg agtaatccgc tttgagatgg accgcgcgcg cattagctag    240
ttggagaggt aacggctcac caaggcgacg atgcgtagcc gacctgagag ggtgatcggc    300
cacattggaa ctgagacacg gtccagactc ctacgggagg cagcagtggg gaatattgca    360
caatgggcga aagcctgatg cagcaacgcc gcgtgagtga tgacggtctt cggattgtaa    420
agctctgtct tttgggacga taatgacggt accaaaggag gaagccacgg ctaactacgt    480
gccagcagcc gcggtaatac gtaggtggca agcgttgtcc ggatttactg gcgtaaaagg    540
atgtgtaggc ggatacttaa gtgagatgtg aaagccccgg gcttaacttg ggactgcat    600 ttcaaactgg gtgtctagag tgcaggagag gaaagcggaa ttcctagtgt agcggtgaaa    660
tgcgtagaga ttaggaagaa catcagtggc gaaggcggct ttctgactg taactgacgc    720 tgaggcatga aagcgtgggg agcaaacagg attagatacc ctggtagtcc acgccgtaaa    780
```

```
cgatgagtac taggtgtagg aggtatcgac tccttctgtg ccgcagtaaa cacaataagt    840
actccgcctg ggaagtacgg tcgcaagatt aaaactcaaa ggaattgacg ggggcccgca    900
caagcagcgg agcatgtggt ttaattcgaa gcaacgcgaa gaaccttacc tagacttgac    960
atctcctgaa tagcgtagag atacgtgaag cccttcgggg caggaagaca ggtggtgcat   1020
ggttgtcgtc agctcgtgtc gtgagatgtt gggttaagtc ccgcaacgag cgcaacccct   1080
atcattagtt gctaccatta agttgagcac tctagtgaga ctgcccgggt taaccgggag   1140
gaaggcgggg atgacgtcaa atcatcatgc cccttatgtc tagggctaca cacgtgctac   1200
aatggtgaga acaacgagat gcaataccgc gaggtggagc caaacttgaa aactcatccc   1260
agttcggatt gtaggctgaa attcgcctac atgaagttgg agttgctagt aatcgcgaat   1320
cagaatgtcg cggtgaatac gttcccgggc cttgtacaca ccgcccgtca ccatgagag   1380 gctggtaaca cccgaagtcc gtgaggtaac ctttatggag ccagcggccg aaggtgggat   1440
tagtgattgg ggtgaagtcg taacaaggta gccgtaggag aacctgcggc tggatcacct   1500
cctttt                                                              1505
```

<210> SEQ ID NO 22
<211> LENGTH: 1532
<212> TYPE: DNA
<213> ORGANISM: Azotobacter vinelandii

<400> SEQUENCE: 22

```
ctgaagagtt tgatcatggc tcagattgaa cgctggcggc aggcctaaca catgcaagtc     60
gagcggcagc gggaccttcg ggttgccggc gagcggcgga cgggtgagta atgcctagga    120
atctgcctgt tagtggggga taacgcgggg aaactcgcgc taataccgca tacgtcctac    180
gggagaaagt gggggacctt cgggcctcac gctaacagat gagcctaggt cggattagct    240
ggttggtggg gtaacggccc accaaggcga cgatccgtaa ctggtctgag aggatgatca    300
gtcacactgg aactgagaca cggtccagac tcctacggga ggcagcagtg gggaatattg    360
gacaatgggc gaaagcctga tccagccatg ccgcgtgtgt gaagaaggtc ttcggattgt    420
aaagcacttt aagtcgggag gaagggctgt aggcgaatac cctgcagttt tgacgttacc    480
gacagaataa gcaccggcta acttcgtgcc agcagccgcg gtaatacgaa gggtgcaagc    540
gttaatcgga attactgggc gtaaagcgcg cgtaggtggt ttggtaagtt ggatgtgaaa    600
gccccgggct caacctggga actgcatcca aaactgccag gctagagtac ggtagagggt    660
ggtggaattt cctgtgtagc ggtgaaatgc gtagatatag gaaggaacac cagtggcgaa    720
ggcgaccacc tggactgata ctgacactga ggtgcgaaag cgtgggagc aaacaggatt    780 agatacctg gtagtccacg ccgtaaacga tgtcgactag ccgttgggct ccttgagagc    840
ttagtggcgc agctaacgca ttaagtcgac cgcctgggga gtacggccgc aaggttaaaa    900
ctcaaatgaa ttgacggggg cccgcacaag cggtggagca tgtggtttaa ttcgaagcaa    960
cgcgaagaac cttacctggc cttgacatcc tgcgaactgg gtagagatac ccgggtgcct   1020
tcgggaacgc agagacaggt gctgcatggc tgtcgtcagc tcgtgtcgtg agatgttggg   1080
ttaagtcccg taacgagcgc aaccttgtc cttagttacc agcacctcgg gtgggcactc   1140
taaggagact gccggtgaca aaccggagga aggtgggat gacgtcaagt catcatggcc   1200
cttacgccca gggctacaca cgtgctacaa tggtcggtac agagggttgc caagccgcga   1260 ggcgagcta atcccagaaa accgatcgta gtccggatcg cagtctgcaa ctcgactgcg   1320
tgaagtcgga atcgctagta atcgcgaatc agaatgtcgc ggtgaatacg ttcccgggcc   1380
```

```
ttgtacacac cgcccgtcac accatgggag tgggttgctc agaagtagc tagtctaacc    1440 ctcgggagga cggttaccac ggagtgattc atgactgggg tgaagtcgta acaaggtagc    1500 cgtagggaa cctgcggctg atcacctcc tt                                   1532
```

<210> SEQ ID NO 23
<211> LENGTH: 1566
<212> TYPE: DNA
<213> ORGANISM: Virgibacillus halophilus

<400> SEQUENCE: 23

```
ttttggagag tttgatcttg gctcaggacg aacgctggcg gcgtgcctaa tacatgcaag      60
tcgagcgcgg gaagcaggat gatcctcatc tgaggtgatt cctgtggaac gagcggcgga    120
cgggtgagta acacgtgggc aacctgcctg taagatcggg ataactcgtg gaaacgcgag    180
ctaataccgg atgatacttt tcatcgcatg gtgagaagtt gaaagatggc tttaagctat    240
cacttacaga tgggcccgcg gcgcattagc tagttggtgg ggtaacggcc taccaaggca    300
acgatgcgta gccgacctga gagggtgatc ggccacactg gactgagac acggcccaga    360 ctcctacggg aggcagcagt agggaatctt ccgcaatgga cgaaagtctg acggagcaac    420
gccgcgtgag tgatgaaggt tttcggatcg taaaactctg ttgtcaggga agaacaagtg    480
ccgtttgaat aaggcggcac cttgacggta cctgaccaga aagccccggc taactacgtg    540
ccagcagccg cggtaatacg tagggggcaa gcgttgtccg gaattattgg gcgtaaagcg    600
cgcgcaggcg gtctttttaag tctgatgtga aagcccacgg cttaaccgtg agggtcatt    660 ggaaactgga ggacttgagt gcagaagagg agagtggaat tccatgtgta gcggtgaaat    720
gcgtagagat atggaggaac accagtggcg aaggcgactc tctggtctgc aactgacgct    780
gaggcgcgaa agcgtgggta gcgaacagga ttagataccc tggtagtcca cgccgtaaac    840
gatgagtgct aggtgttagg gggtttccgc cccttagtgc tgaagttaac gcattaagca    900
ctccgcctgg ggagtacggc cgcaaggctg aaactcaaaa gaattgacgg gggcccgcac    960
aagcggtgga gcatgtggtt taattcgaag caacgcgaag aaccttacca ggtcttgaca   1020
tcctctgaca gccttagaga taaggtgttc ccttcgggga cagagtgaca ggtggtgcat   1080
ggttgtcgtc agctcgtgtc gtgagatgtt gggttaagtc ccgcaacgag cgcaaccctt   1140
gagattagtt gccagcatta agttgggcac tctaatctga ctgccggtga caaaccggag   1200
gaaggtgggg atgacgtcaa atcatcatgc cccttatgac ctgggctaca cacgtgctac   1260
aatggatggt acagagggaa gcgaagccgc gaggtgaagc aaatcccaca aaaccattct   1320
cagttcggat tgcaggctgc aactcgcctg catgaagccg gaatcgctag taatcgcgga   1380
tcagcatgcc gcggtgaata cgttcccggg ccttgtacac accgcccgtc acaccacgag   1440
agttggtaac acccgaagtc ggtgaggtaa ccttttttgga gccagccgcc gaaggtggga   1500
cgaatgattg gggtgaagtc gtaacaaggt agccgtatcg gaaggtgcgg ctggatcacc   1560
tcctt                                                              1566
```

<210> SEQ ID NO 24
<211> LENGTH: 1561
<212> TYPE: DNA
<213> ORGANISM: Lactobacillus delbrueckii

<400> SEQUENCE: 24

```
attgagagtt tgatcctggc tcaggacgaa cgctggcggc gtgcctaata catgcaagtc      60
```

```
gagcgagctg aattcaaaga tcccttcggg gtgatttgtt ggacgctagc ggcggatggg      120
tgagtaacac gtgggcaatc tgccctaaag actgggatac cacttggaaa caggtgctaa      180
taccggataa caacatgaat cgcatgattc aagtttgaaa ggcggcgcaa gctgtcactt      240
taggatgagc ccgcggcgca ttagctagtt ggtggggtaa aggcctacca aggcaatgat      300
gcgtagccga gttgagagac tgatcggcca cattgggact gagacacggc ccaaactcct      360 acggaggca gcagtaggga atcttccaca atggacgcaa gtctgatgga gcaacgccgc      420
gtgagtgaag aaggtcttcg gatcgtaaag ctctgttgtt ggtgaagaag atagaggca      480 gtaactggtc tttatttgac ggtaatcaac cagaaagtca cggctaacta cgtgccagca      540
gccgcggtaa tacgtaggtg gcaagcgttg tccggattta ttgggcgtaa agcgagcgca      600
ggcggaatga taagtctgat gtgaaagccc acggcttaac cgtggaactg catcggaaac      660
tgtcattctt gagtgcagaa gaggagagtg gaactccatg tgtagcggtg aatgcgtag      720 atatatggaa gaacaccagt ggcgaaggcg gctctctggt ctgcaactga cgctgaggct      780
cgaaagcatg ggtagcgaac aggattagat accctgtag tccatgccgt aaacgatgag      840
cgctaggtgt tggggacttt ccggttctca gtgccgcagc aaacgcgtta agcgctccgc      900
ctggggagta cgaccgcaag gttgaaactc aaaggaattg acgggggccc gcacaagcgg      960
tggagcatgt ggtttaattc gaagcaacgc gaagaacctt accaggtctt gacatcctgc     1020
gctacaccta gagataggtg gttcccttcg gggacgcaga gacaggtggt gcatggctgt     1080
cgtcagctcg tgtcgtgaga tgttgggtta agtcccgcaa cgagcgcaac ccttgtcttt     1140
agttgccatc attaagttgg gcactctaaa gagactgccg gtgacaaacc ggaggaaggt     1200
ggggatgacg tcaagtcatc atgccccta tgacctgggc tacacacgtg ctacaatggg     1260
cagtacaacg agaagcgaac ccgcgagggt aagcggatct cttaaagctg ctctcagttc     1320
ggactgcagg ctgcaactcg cctgcacgaa gctggaatcg ctagtaatcg cggatcagca     1380
cgccgcggta aatacgttcc cgggccttgt acacaccgcc cgtcacacca tggaagtctg     1440
caatgcccaa agtcggtgag ataacccttta taggagtcag ccgcctaagg cagggcagat     1500
gactggggtg aagtcgtaac aaggtagccg taggagaacc tgcggctgga tcacctcctt     1560
t                                                                    1561

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 25
caagtcgcac gaaggtttc                                                   19

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 26
cggggatttc acatctgact                                                  20

<210> SEQ ID NO 27
<211> LENGTH: 20
```

```
<212> TYPE: DNA
<213> ORGANISM: Artificial Sequence
<220> FEATURE:
<223> OTHER INFORMATION: Synthetic oligonucleotide primer

<400> SEQUENCE: 27
gggtcaagag cttcacctac                                             20

<210> SEQ ID NO 28
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 28
cgatgtctgc cagggaatg                                              19

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 29
tgcgcttatg aatggaggag                                             20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 30
ctttatcagg cctggtaccg                                             20

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 31
tctcttgcat aagagaaaat tgaaa                                       25

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 32
ctacgcattt caccgctaca                                             20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 33
```

```
ggagcttgct cccttaggtc                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 34
ctcaagttcc ccagtttcca                                              20

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 35
ccggatagga tcttctcctt c                                            21

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 36
ctacgcattt caccgctaca                                              20

<210> SEQ ID NO 37
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 37
tttatacata taattagatt gaaagatgg                                    29

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 38
ctacgcattt caccgctaca                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 39
gatctttctt ggggatggg                                               20

<210> SEQ ID NO 40
<211> LENGTH: 20
<212> TYPE: DNA
<213> ORGANISM: Artificial Sequence
```

```
<220> FEATURE:
<223> OTHER INFORMATION: Synthetic oligonucleotide primer

<400> SEQUENCE: 40
ccgaacccaa cagtccaata                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 41
gatgaagctc cttcgggagt                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 42
aatgcagcac ccaggttaag                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 43
caagtcgagc gagaaacctt                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 44
gaaatgcagt ccccaggtta                                               20

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 45
ggtgcttgca cttgaaagat t                                             21

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 46
ctcgctttac gcccaataaa                                               20
```

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 47
cgagcgagct gaattcaaag                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 48
ctcgctttac gcccaataaa                                                    20

<210> SEQ ID NO 49
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 49
ctcgttgatg atcggtgct                                                     19

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 50
taaatccgga taacgcttgc                                                    20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 51
accgcctggt tttgatgtta                                                    20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 52
catttcaccg ctacacatgg                                                    20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 53
ggaactcttc ggagggaagt                                               20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 54
cagtttccaa tgcacgtttg                                               20

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 55
tgcagcattg tgaaataatg aa                                            22

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 56
ctacgcattt caccgctaca                                               20

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 57
ccggataatt tattttctct cctg                                          24

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 58
ctacgcattt caccgctaca                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 59
atttatcgct tcgcatggag                                               20

<210> SEQ ID NO 60

```
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 60
ctacgcattt caccgctaca                                                    20

<210> SEQ ID NO 61
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 61
cgggagcttg ctccttga                                                      18

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 62
ctctagctcg ccagttttgg                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 63
aagtcgagcg gatgagaaga                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 64
cgctttacgc ccagtaattc                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 65
gtcgaacgat gaagcctttc                                                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 66
```
aggaattccg atctcccta                                                20

<210> SEQ ID NO 67
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 67
gtgccagcag ccgcggtaa                                                 19

<210> SEQ ID NO 68
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 68
tggactacca gggtatctaa tcctgtt                                        27

<210> SEQ ID NO 69
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 69
cctcatctga ggtgattcct g                                              21

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 70
tcctccagtt tccaatgacc                                                20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 71
tcgagcgaaa cagaagtgaa                                                20

<210> SEQ ID NO 72
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 72
tctgtgatga atgtgatgcg ga                                             22

<210> SEQ ID NO 73
<211> LENGTH: 20
<212> TYPE: DNA

```
<213> ORGANISM: Artificial Sequence
<220> FEATURE:
<223> OTHER INFORMATION: Synthetic oligonucleotide primer

<400> SEQUENCE: 73
gctgaacttt cacacgatgc                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 74
acgcaggcga tttatcatca                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 75
tttgctttcc ggtggctcat                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 76
agcccatatc aaccagcatc                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 77
gctgaaggag ggacactttt                                              20

<210> SEQ ID NO 78
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 78
agagtttgaa cgtgttggtg gt                                           22

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 79
tcagatcacg gtttgttgct                                              20
```

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 80
aacggttaac aatcagccca                                              20

<210> SEQ ID NO 81
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 81
tcttaccgga aagaattcg cca                                           23

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 82
cgcaagacaa gcagttcaag                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 83
caaccaactg gatcaaggga                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 84
acctgctgaa gcagcgattt                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 85
aatcataccg atcagtgccg                                              20

<210> SEQ ID NO 86
<211> LENGTH: 20
<212> TYPE: DNA
<213> ORGANISM: Artificial Sequence
<220> FEATURE:

<223> OTHER INFORMATION: Synthetic oligonucleotide primer

<400> SEQUENCE: 86
tgctgaacgg aaaacatcct                                         20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 87
aaaatcggtg cggaaggtcc                                         20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 88
tgcaactaca cttaccgcaa                                         20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 89
tgcgcttatg aatggaggag                                         20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 90
aaaagggccg atcacatggg                                         20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 91
ctgtaatccg gtccgtacac                                         20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 92
atatcctgcg ctggtacaac                                         20

```
<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 93
cggcagactt gaagctcgag                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 94
tcttgtacat ggaagccgtg                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 95
cgactaacct gatcgcactt                                               20

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 96
tgaagctcag atttcacggc t                                             21

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 97
attacgccga ttccttctgg                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 98
tgacattcca ttcatccggg                                               20

<210> SEQ ID NO 99
<211> LENGTH: 22
<212> TYPE: DNA
<213> ORGANISM: Artificial Sequence
<220> FEATURE:
<223> OTHER INFORMATION: Synthetic oligonucleotide probe
```

```
<400> SEQUENCE: 99
aaatggcgga gatcacgtat ca                                            22

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 100
atcccagcca aatttccaca                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 101
gcaaaacaaa caggctccaa                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 102
aaatcagcct ctggcttgcc                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 103
ctgaccggga tagttggttc                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 104
ctggatatcc cgcatttggt                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 105
ctgtatgccg ctttgacgga                                               20

<210> SEQ ID NO 106
<211> LENGTH: 20
```

```
<212> TYPE: DNA
<213> ORGANISM: Artificial Sequence
<220> FEATURE:
<223> OTHER INFORMATION: Synthetic oligonucleotide primer

<400> SEQUENCE: 106
gcgaggaatc atgtagcctt                                              20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 107
aggttccgat gtagtgcttg                                              20

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 108
acatacaacg cacaccgaga a                                            21

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 109
atttcctgca accagagctt                                              20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 110
tccgaagctg ctgaaatctt                                              20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 111
acctgaccgt ggtggagaaa                                              20

<210> SEQ ID NO 112
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 112
```
ttgaaagtaa atcgcgcgtc                                          20

<210> SEQ ID NO 113
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 113
aatcatcaca gatgcggagg                                          20

<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 114
attgtgccat ccggctatgg                                          20

<210> SEQ ID NO 115
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 115
gtgccgagat gaagaagtga                                          20

<210> SEQ ID NO 116
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 116
gctgacctat gtgaagtccc                                          20

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 117
agatcgatgg cgtgttggtg                                          20

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 118
tgataaagat ggacgccgac                                          20

<210> SEQ ID NO 119
<211> LENGTH: 20
<212> TYPE: DNA
<213> ORGANISM: Artificial Sequence

```
<220> FEATURE:
<223> OTHER INFORMATION: Synthetic oligonucleotide primer

<400> SEQUENCE: 119
ctgggactac atgaagcagg                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 120
tggacgccga gatcctctac                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 121
taggtcttct ggagcgactt                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 122
tgggcttggt gtatgtgttt                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 123
atggcacaaa gctacggctt                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 124
gaaccatgag cccgtaatga                                               20

<210> SEQ ID NO 125
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 125
ggatgtacag aaaattgcag c                                             21
```

<210> SEQ ID NO 126
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 126
agcttattgg agaggttaca actgt                                          25

<210> SEQ ID NO 127
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 127
aggagttgat atcaggtatg gt                                             22

<210> SEQ ID NO 128
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 128
gcatattgcc tttggtgtgg                                                20

<210> SEQ ID NO 129
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 129
ccccatgggg gtaaccattg                                                20

<210> SEQ ID NO 130
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 130
tccatcctgg ggttgttttc                                                20

<210> SEQ ID NO 131
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 131
gctatatggg ctccaaagca                                                20

<210> SEQ ID NO 132
<211> LENGTH: 22
<212> TYPE: DNA
<213> ORGANISM: Artificial Sequence
<220> FEATURE:
<223> OTHER INFORMATION: Synthetic oligonucleotide probe

```
<400> SEQUENCE: 132
aaaagccgat gtagtactcg ct                                            22

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 133
ttccgaaaac agacagcctt                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 134
accagtgaag aactggaagc                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 135
acgcgaagac aagatctgcc                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 136
tcaccgttca aagtccagtc                                               20
```

DEFINED MICROBIAL COMPOSITIONS

CROSS REFERENCE TO RELATED APPLICATION

This application is the § 371 U.S. National Stage of International Application No. PCT/US2017/049326, filed Aug. 30, 2017, which was published in English under PCT Article 21(2), which in turn claims the benefit of U.S. Provisional Application No. 62/381,441, filed Aug. 30, 2016, which is incorporated herein by reference in its entirety.

FIELD

This disclosure relates to microbial compositions and methods of their use, particularly for agricultural processes and uses.

BACKGROUND

As a consequence of population growth, food consumption is also increasing. On the other hand, cultivable agricultural land and productivity are significantly reduced due to global industrialization, drought, salinity, and global warming (Galamero et al., In *Microbial Strategies for Crop Improvement*, Springer Berlin, pp. 1-22, 2009). This problem may be addressed by practicing sustainable agriculture, the basic principle of which is to significantly reduce chemical inputs, such as fertilizers, insecticides, and herbicides, while reducing the emission of greenhouse gas.

Excessive use of chemical fertilizers in agriculture, results in a large number of environmental problems because some fertilizers contain heavy metals (e.g., cadmium and chromium) and high concentrations of radionuclides. These fertilizers in the agro-ecosystem constitute the main source of heavy metals and radionuclides in plants and some result in the accumulation of inorganic pollutants (Savci, *Int. J. Env. Sci. Dev.* 3:77-80, 2012; Malakoff, *Science* 281:190-192, 1998). Greenhouses and aquaculture use especially large amounts of chemical fertilizers during the peak season, resulting in polluted water resources, and crop production quantity and quality of product deteriorates. In light of these disadvantages of chemical fertilizers, plant-beneficial microbial inoculants provide promise as components of integrated nutrient management strategies.

SUMMARY

Disclosed herein are compositions including cells of a defined set of microbial species (for example, 3 microbial species, 16 microbial species, 17 microbial species, 19 microbial species, 20 microbial species, 21 microbial species, or 22 microbial species). In some embodiments, the compositions include cells of one or more microbial species having functional characteristics or activities (such as metabolic activities) including but not limited to nitrogen metabolism, salt tolerance, phosphate and/or calcium and/or zinc salt solubilization activity, cellulolytic activity, chitinolytic activity, phytohormone production, iron metabolism activity and/or dephosphorylation of organic matter activity. In some embodiments, the compositions include cells of one or more (such as 2 or more, 3, or more, 4 or more, 5 or more, 6 or more, 7 or more, 8 or more, 9 or more 10 or more, 11 or more, 12 or more, 13 or more, 14 or more, 15 or more) microbial species that grow under aerobic conditions. In other embodiments, the compositions include cells of one or more (such as 2 or more, 3, or more, 4 or more, 5 or more) microbial species that grow under anaerobic conditions. In one non-limiting example, the composition includes cells of 16 microbial species that grow under aerobic conditions and cells of 6 microbial species that grow under anaerobic conditions. Aerobic and anaerobic growth conditions include, but are not limited to, those described in Example 1 herein.

In one embodiment, the composition includes cells of microbial species including or consisting of each of *Lactobacillus delbrueckii, Virgibacillus halophilus, Azotobacter vinelandii, Clostridium pasteurianum, Paenibacillus chibensis, Streptomyces griseus, Pseudomonas* sp. (closely related to *P. entomophila, P. fluorescens*, and *P. putida*, for example, a microbial species with 16S rRNA sequence with at least 99% sequence identity to SEQ ID NO: 17), *Pseudomonas putida, Bacillus* sp. (closely related to *B. kochii, B. pocheonensis*, and *Bacillus* sp. (strain R-27341), for example, a microbial species with a 16S rRNA sequence with at least 99% sequence identity to SEQ ID NO: 15), *Bacillus amyloliquefaciens, Oceanobacillus oncorhynchi, Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12), *Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus*. In another embodiment, the composition includes cells of microbial species including or consisting of each of *Lactobacillus delbrueckii, Virgibacillus halophilus, Azotobacter vinelandii, Clostridium pasteurianum, Streptomyces griseus, Pseudomonas* sp. (closely related to *P. entomophila, P. fluorescens*, and *P. putida*, for example, a microbial species with 16S rRNA sequence with at least 99% sequence identity to SEQ ID NO: 17) *Pseudomonas putida, Bacillus* sp. (closely related to *B. kochii, B. pocheonensis*, and *Bacillus* sp. (strain R-27341), for example, a microbial species with a 16S rRNA sequence with at least 99% sequence identity to SEQ ID NO: 15), *Bacillus amyloliquefaciens. Oceanobacillus oncorhynchi, Bacillus licheniformis, Lactobacillus vini, Bacillus subtilis, Lactobacillus buchneri, Bacillus megaterium, Acetobacter pasteurianus, Clostridium beijerinckii, Lactobacillus casei/paracasei*, and *Bacillus flexus*. In other embodiments, the compositions include cells of microbial species including or consisting of microbes with 16S rDNA sequences having at least 99% sequence identity to each of SEQ ID NOs: 3-24; each of SEQ ID NOs: 3-8, 10, 11, 13-18, and 20-24; each of SEQ ID NOs: 3-7 and 9-24; each of SEQ ID NOs: 3-7, 10, 11, 13-18, and 20-24; each of SEQ ID NOs: 3-8, 10, 11, 14, 16-18, 20-22, and 24; or each of SEQ ID NOs: 3-14, 16-22, and 24. In another embodiment, the composition includes the collection of microbes contained in one or more of American Type Culture Collection deposit numbers PTA-123288, PTA-123298, and/or PTA-123289.

In other embodiments, the composition includes cells of at least one microbial species with nitrogen metabolism activity, at least one microbial species tolerant to 5% NaCl, at least one microbial species with phosphate and/or calcium and/or zinc salt solubilization activity, at least one microbial species with cellulolytic and/or chitinolytic activity, at least one microbial species with malic acid metabolism activity, at least one microbial species with phytohormone (such as indole (auxin)) production activity, at least one microbial species with iron metabolizing activity, at least one microbial species with dephosphorylation of organic matter activity, or a combination of any two or more thereof.

Also disclosed herein are methods of using the disclosed compositions that include contacting soil, plants, plant parts, or seeds with the composition. The microbial compositions may be applied to soil, plant, plant parts, and/or seeds alone or in combination with additional component(s) (such as chitin, chitosan, glucosamine, amino acids, and/or liquid fertilizer).

In additional embodiments, the disclosed microbial compositions are used in methods of degrading biological materials, such as chitin-containing biological materials. In some examples, the chitin-containing materials are mixed with a disclosed microbial composition and fermented to produce a fermented mixture. The fermented mixture optionally may be separated into solid and liquid fractions. These fractions can subsequently be used in agricultural applications in combination with the disclosed microbial compositions or can be used in further degradation processes.

The foregoing and other features of the disclosure will become more apparent from the following detailed description, which proceeds with reference to the accompanying figures.

SEQUENCE LISTING

Figure 1:
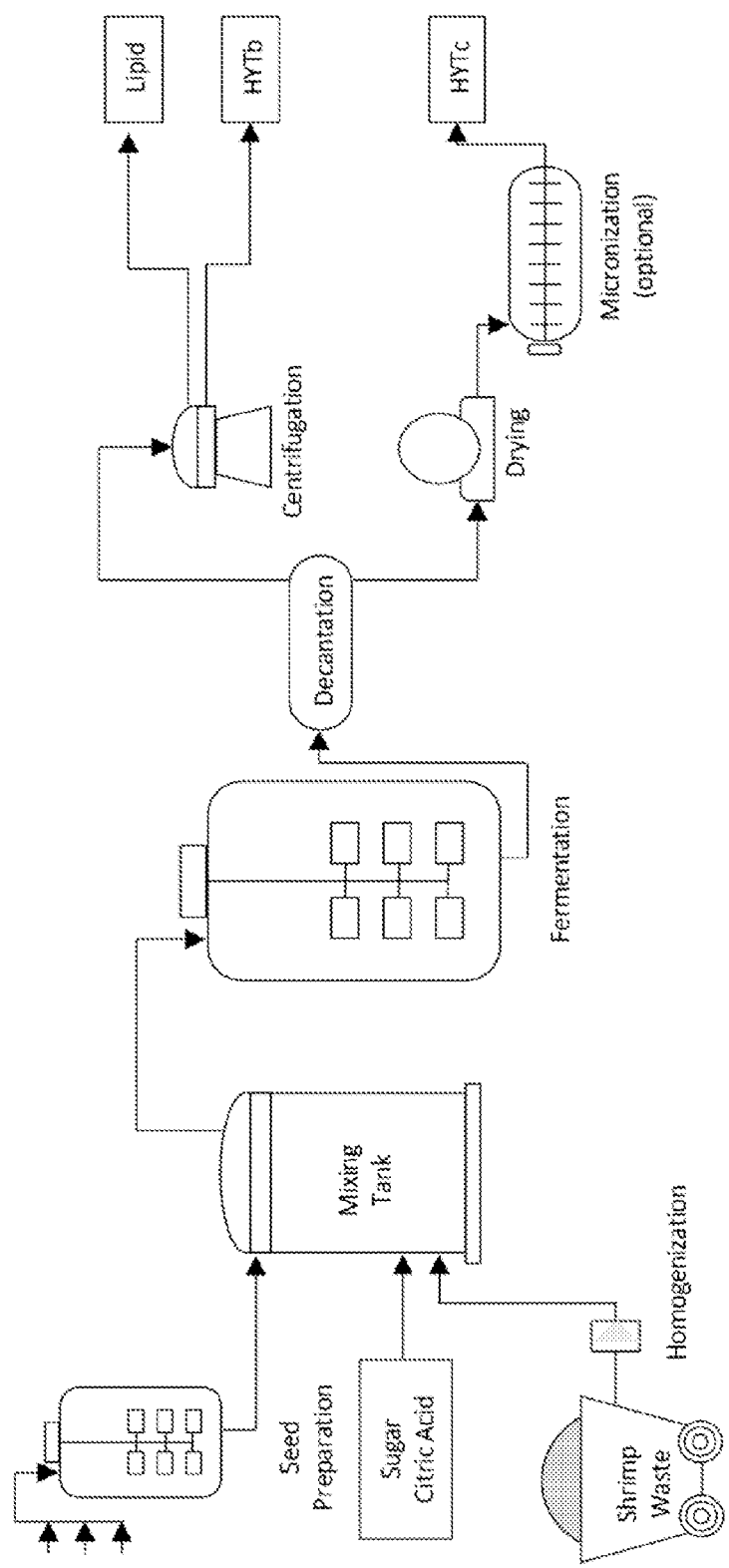
FIG. 1 is a schematic showing an exemplary process for biodegradation of a chitin-containing biological material (exemplified as shrimp waste) with a disclosed microbial composition.

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Feb. 26, 2019, and is ~69 kilobytes, which is incorporated by reference herein.

SEQ ID NOs: 1 and 2 are nucleic acid sequences of 16S rDNA forward and reverse primers, respectively.

SEQ ID NO: 3 is a 16S rDNA nucleotide sequence from a microbe identified as *Bacillus megaterium*.

SEQ ID NO: 4 is a 16S rDNA nucleotide sequence from a microbe identified as *Lactobacillus casei/paracasei*.

SEQ ID NO: 5 is a 16S rDNA nucleotide sequence from a microbe identified as *Clostridium beijerinckii*.

SEQ ID NO: 6 is a 16S rDNA nucleotide sequence from a microbe identified as *Acetobacter pasteurianus*.

SEQ ID NO: 7 is a 16S rDNA nucleotide sequence from a microbe identified as *Lactobacillus buchneri*.

SEQ ID NO: 8 is a 16S rDNA nucleotide sequence from a microbe identified as *Bacillus subtilis*.

SEQ ID NO: 9 is a 16S rDNA nucleotide sequence from a microbe identified as *Paenibacillus cookii*.

SEQ ID NO: 10 is a 16S rDNA nucleotide sequence from a microbe identified as *Lactobacillus vini*.

SEQ ID NO: 11 is a 16S rDNA nucleotide sequence from a microbe identified as *Bacillus licheniformis*.

SEQ ID NO: 12 is a 16S rDNA nucleotide sequence from a microbe identified as *Paenibacillus lautus*.

SEQ ID NO: 13 is a 16S rDNA nucleotide sequence from a microbe identified as *Oceanobacillus oncorhynchi*.

SEQ ID NO: 14 is a 16S rDNA nucleotide sequence from a microbe identified as *Bacillus amyloliquefaciens*.

SEQ ID NO: 15 is a 16S rDNA nucleotide sequence from a microbe identified as *Bacillus* sp.

SEQ ID NO: 16 is a 16S rDNA nucleotide sequence from a microbe identified as *Pseudomonas putida*, SEQ ID NO: 17 is a 16S rDNA nucleotide sequence from a microbe identified as *Pseudomonas* sp.

SEQ ID NO: 18 is a 16S rDNA nucleotide sequence from a microbe identified as *Streptomyces griseus*.

SEQ ID NO: 19 is a 16S rDNA nucleotide sequence from a microbe identified as *Paenibacillus chibensis*.

SEQ ID NO: 20 is a 16S rDNA nucleotide sequence from a microbe identified as *Bacillus flexus*.

SEQ ID NO: 21 is a 16S rDNA nucleotide sequence from a microbe identified as *Clostridium pasteurianum*.

SEQ ID NO: 22 is a 16S rDNA nucleotide sequence from a microbe identified as *Azotobacter vinelandii*.

SEQ ID NO: 23 is a 16S rDNA nucleotide sequence from a microbe identified as *Virgibacillus halophilus*.

SEQ ID NO: 24 is a 16S rDNA nucleotide sequence from a microbe identified as *Lactobacillus delbrueckii*.

SEQ ID NOs: 25-66 and 69-136 are nucleotide sequences of species-specific oligonucleotide primers and probes.

SEQ ID NOs: 67-68 are nucleotide sequences of universal 16S rRNA prokaryote primers.

DETAILED DESCRIPTION

I. Terms

Unless otherwise noted, technical terms are used according to conventional usage. Definitions of common terms in molecular biology may be found in Krebs et al., *Lewin's Genes XI*, published by Jones and Bartlett Learning, 2012 (ISBN 1449659853); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 2011 (ISBN 8126531789); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." As used herein, "comprises" means "includes." Thus, "comprising A or B," means "including A, B, or A and B," without excluding additional elements. All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Aquatic Animal: An animal that lives in salt or fresh water. In particular embodiments disclosed herein, an aquatic animal includes aquatic arthropods, such as shrimp, krill, copepods, barnacles, crab, lobsters, and crayfish. In other embodiments, an aquatic animal includes fish. An aquatic animal by-product includes any part of an aquatic animal, particularly parts resulting from commercial processing of an aquatic animal. Thus, in some examples, aquatic animal by-products include one or more of shrimp cephalothorax or exoskeleton, crab or lobster exoskeleton, or fish skin or scales.

Contacting: Placement in direct physical association, including both in solid and liquid form. For example, contacting can occur with one or more microbes (such as the microbes in a microbial consortium) and a biological sample in solution. Contacting can also occur with one or more microbes (such as the microbes in a microbial consortium) and soil, plants, and/or plant parts (such as foliage, stem, seedling, roots, and/or seeds).

Culture medium: A set of culture conditions (which in some examples is a synthetic or non-naturally occurring set of conditions) including nutrients to support the viability, function, and/or growth of a specific population of cells, such as one or more microbial species. Culture media generally include components such as a carbon source, a nitrogen source and a buffer to maintain pH. Additional components in culture media also may include one or more of hormones, growth factors, protease inhibitors, protein hydrolysates, shear force protectors, proteins, vitamins, trace elements, inorganic salts, minerals, and/or lipids.

Culturing: Intentional growth of one or more organisms or cells in the presence of assimilable sources of carbon, nitrogen and mineral salts. In an example, such growth can take place in a solid or semi-solid nutritive medium, or in a liquid medium in which the nutrients are dissolved or suspended. In a further example, the culturing may take place on a surface or by submerged culture. The nutritive medium can be composed of complex nutrients or can be chemically defined.

Fermenting: A process that results in the breakdown of complex organic compounds into simpler compounds, for example by microbial cells (such as bacteria and/or fungi). The fermentation process may occur under aerobic conditions, anaerobic conditions, or both (for example, in a large volume where some portions are aerobic and other portions are anaerobic). In some non-limiting embodiments, fermenting includes the enzymatic and/or non-enzymatic breakdown of compounds present in aquatic animals or animal by-products, such as chitin.

Isolated: An "isolated" biological component (such as a nucleic acid, protein or organism) has been substantially separated or purified away from other biological components (such as other cells, cell debris, or other proteins or nucleic acids). Biological components that have been "isolated" include those components purified by standard purification methods. The term also embraces recombinant nucleic acids, proteins or microbes, as well as chemically synthesized nucleic acids or peptides. The term "isolated" (or "enriched" or "purified") does not require absolute purity, and can include microbes or molecules that are at least 50% isolated, such as at least 75%, 80%, 90%, 95%, 98%, 99% or even 100% isolated.

Liquid fertilizer: An aqueous solution or suspension containing soluble nitrogen. In some examples, the soluble nitrogen in a liquid fertilizer includes an organic source of nitrogen such as urea, or urea derived from anhydrous ammonia (such as a solution of urea and ammonium nitrate (UAN)). Aqua ammonia (20-32% anhydrous ammonia) can also be used. In other examples, the soluble nitrogen in a liquid fertilizer includes nitrogen-containing inorganic salts such as ammonium hydroxide, ammonium nitrate, ammonium sulfate, ammonium pyrophosphate, ammonium thiosulfate or combinations of two or more thereof. In some embodiments the liquid fertilizer includes a non-naturally occurring nitrogen source (such as ammonium pyrophosphate or ammonium thiosulfate) and/or other non-naturally occurring components.

Common liquid non-natural fertilizer blends are specified by their content of nitrogen-phosphate-potassium (N-P-K percentages) and include addition of other components, such as sulfur or zinc. Examples of human-made blends include 10-34-0, 10-30-0 with 2% sulfur and 0.25% zinc (chelated), 11-37-0, 12-30-0 with 3% sulfur, 2-4-12, 2-6-12, 4-10-10, 3-18-6, 7-22-5, 8-25-3, 15-15-3, 17-17-0 with 2% sulfur, 18-18-0, 18-18-0 with 2% sulfur, 28-0-0 UAN, 9-27-0 with 2% sulfur and potassium thio-sulfate.

Microbe: A microorganism, including but not limited to bacteria, archaebacteria, fungi, and algae (such as microalgae). In some examples, microbes are single-cellular organisms (for example, bacteria, cyanobacteria, some fungi, or some algae). In other examples, the term microbes includes multi-cellular organisms, such as certain fungi or algae (for example, multicellular filamentous fungi or multicellular algae).

Microbial composition: A composition (which can be solid, liquid, or at least partially both) that includes cells of at least one type (or species) of microbe (or a population of cells of at least one type of microbe). In some examples, a microbial composition comprises cells of one or more types (species) of microbes (or one or more populations of microbes) in a liquid medium (such as a storage, culture, or fermentation medium), for example, as a suspension in the liquid medium. In other examples, a microbial composition includes cells of one or more types (species) of microbes (or one or more populations of microbes) on the surface of or embedded in a solid or gelatinous medium (including but not limited to a culture plate), or a slurry or paste.

Microbial consortium: A mixture, association, or assemblage of cells of two or more microbial species, which in some instances are in physical contact with one another. The microbes in a consortium may affect one another by direct physical contact, through biochemical interactions, or both. For example, microbes in a consortium may exchange nutrients, metabolites, or gases with one another. Thus, in some examples, at least some of the microbes in a consortium are metabolically interdependent. Such interdependent interactions may change in character and extent through time and with changing culture conditions.

II. Microbial Compositions

Disclosed herein are microbial compositions that include cells of a defined set of microbes or microbial species. In some embodiments, the disclosed compositions include cells of a defined set of microbes (for example, 3 microbial species, 16 microbial species, 19 microbial species, 20 microbial species, 21 microbial species, or 22 microbial species) as set forth below. Any of the compositions disclosed herein may also include one or more non-microbial components, including but not limited to one or more of carbon sources, nitrogen sources, buffers, hormones, growth factors, protease inhibitors, protein hydrolysates, shear force protectors, proteins, amino acids, vitamins, trace elements, inorganic salts, minerals, and/or lipids. In some examples, one or more additional microbial species may also be added to the composition, for example to provide or supplement a desired activity of the composition.

A. Defined Microbial Compositions

Disclosed herein are compositions including cells of a defined set of microbial species. For example, in some embodiments, the compositions include microbial isolates that are combined in a single composition, and in some examples co-cultured or co-fermented.

In one example, the composition includes cells of microbial species including or consisting of each of *Lactobacillus delbrueckii*, *Virgibacillus halophilus*, *Azotobacter vinelandii*, *Clostridium pasteurianum*, *Paenibacillus chibensis*, *Streptomyces griseus*, *Pseudomonas* sp. (closely related to *P. entomophila*, *P. fluorescens*, and *P. putida*; for example, a microbial species with 16S rRNA sequence with at least 99% sequence identity to SEQ ID NO: 17), *Pseudomonas putida*, *Bacillus* sp. (closely related to *B. kochii*, *B. pocheonensis*, and *Bacillus* sp. (strain R-27341); for example, a microbial species with a 16S rRNA sequence with at least 99% sequence identity to SEQ ID NO: 15), *Bacillus amyloliquefaciens*. *Oceanobacillus oncorhynchi*, *Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12), *Bacillus licheniformis*, *Lactobacillus vini*, *Paenibacillus cookii*, *Bacillus subtilis*, *Lactobacillus buchneri*, *Bacillus megaterium*, *Acetobacter pasteurianus*, *Clostridium beijerinckii*, *Lactobacillus casei/paracasei*, and *Bacillus flexus*. In another example, the composition includes cells of microbial species including or consisting of each of *Lactobacillus delbrueckii*, *Virgibacillus halophilus*, *Azotobacter vinelandii*, *Clostridium pasteurianum*, *Streptomyces griseus*, *Pseudomonas* sp. (closely related to *P. entomophila*, *P. fluorescens*, and *P. putida*, for example, a microbial species with 16S rRNA sequence with at least 99% sequence identity to SEQ ID NO: 17), *Pseudomonas putida*, *Bacillus* sp. (closely related to *B. kochii*, *B. pocheonensis*, and *Bacillus* sp. (strain R-27341), for example, a microbial species with a 16S rRNA sequence with at least 99% sequence identity to SEQ ID NO: 15), *Bacillus amyloliquefaciens*, *Oceanobacillus oncorhynchi*, *Bacillus licheniformis*, *Lactobacillus vini*, *Bacillus subtilis*, *Lactobacillus buchneri*, *Bacillus megaterium*, *Acetobacter pasteurianus*, *Clostridium beijerinckii*, *Lactobacillus casei/paracasei*, and *Bacillus flexus*. In an additional example, the composition includes cells of microbial species including or consisting of each of *Lactobacillus delbrueckii*, *Virgibacillus halophilus*, *Azotobacter vinelandii*, *Clostridium pasteurianum*, *Paenibacillus chibensis*, *Streptomyces griseus*, *Pseudomonas* sp. (closely related to *P. entomophila*, *P. fluorescens*, and *P. putida*, for example, a microbial species with 16S rRNA sequence with at least 99% sequence identity to SEQ ID NO: 17). *Pseudomonas putida*, *Bacillus* sp. (closely related to *B. kochii*, *B. pocheonensis*, and *Bacillus* sp. (strain R-27341), for example, a microbial species with a 16S rRNA sequence with at least 99% sequence identity to SEQ ID NO: 15), *Bacillus amyloliquefaciens*, *Oceanobacillus oncorhynchi*, *Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12), *Bacillus licheniformis*, *Lactobacillus vini*, *Paenibacillus cookii*, *Lactobacillus buchneri*, *Bacillus megaterium*, *Acetobacter pasteurianus*, *Clostridium beijerinckii*, *Lactobacillus casei/paracasei*, and *Bacillus flexus*. In a further example, the composition includes cells of microbial species including or consisting of *Lactobacillus delbrueckii*, *Virgibacillus halophilus*, *Azotobacter vinelandii*, *Clostridium pasteurianum*, *Streptomyces griseus*, *Pseudomonas* sp. (closely related to *P. entomophila*, *P. fluorescens*, and *P. putida*, for example, a microbial species with 16S rRNA sequence with at least 99% sequence identity to SEQ ID NO: 17). *Pseudomonas putida*, *Bacillus* sp. (closely related to *B. kochii*, *B. pocheonensis*, and *Bacillus* sp. (strain R-27341), for example, a microbial species with a 16S rRNA sequence with at least 99% sequence identity to SEQ ID NO: 15), *Bacillus amyloliquefaciens*, *Oceanobacillus oncorhynchi*, *Bacillus licheniformis*, *Lactobacillus vini*, *Bacillus subtilis*, *Lactobacillus buchneri*, *Bacillus megaterium*, *Acetobacter pasteurianus*, *Clostridium beijerinckii*, *Lactobacillus casei/paracasei*, and *Bacillus flexus*.

In other examples, the composition includes cells of microbial species including or consisting of each of *Lactobacillus delbrueckii*, *Virgibacillus halophilus*, *Azotobacter vinelandii*, *Clostridium pasteurianum*, *Paenibacillus chibensis*, *Pseudomonas* sp. (closely related to *P. entomophila*, *P. fluorescens*, and *P. putida*, for example, a microbial species with 16S rRNA sequence with at least 99% sequence identity to SEQ ID NO: 17), *Pseudomonas putida*, *Bacillus* sp. (closely related to *B. kochii*, *B. pocheonensis*, and *Bacillus* sp. (strain R-27341), for example, a microbial species with a 16S rRNA sequence with at least 99% sequence identity to SEQ ID NO: 15), *Bacillus amyloliquefaciens*, *Oceanobacillus oncorhynchi*, *Paenibacillus lautus* (e.g., closely related to *Paenibacillus launtus* and *Paenibacillus* sp. (strain Y412MC10), for example, a microbial species with 16S rRNA sequence with at least 99% sequence identity to SEQ ID NO: 12), *Bacillus licheniformis*, *Lactobacillus vini*, *Paenibacillus cookii*, *Bacillus subtilis*, *Lactobacillus buchneri*, *Bacillus megaterium*, *Acetobacter pasteurianus*, and *Lactobacillus casei/paracasei*. In further examples, the composition includes cells of microbial species including or consisting of each of *Lactobacillus delbrueckii*, *Virgibacillus halophilus*, *Azotobacter vinelandii*, *Clostridium pasteurianum*, *Pseudomonas* sp. (closely related to *P. entomophila*, *P. fluorescens*, and *P. putida*, for example, a microbial species with 16S rRNA sequence with at least 99% sequence identity to SEQ ID NO: 17), *Pseudomonas putida*, *Bacillus* sp. (closely related to *B. kochii*, *B. pocheonensis*, and *Bacillus* sp. (strain R-27341), for example, a microbial species with a 16S rRNA sequence with at least 99% sequence identity to SEQ ID NO: 15), *Bacillus amyloliquefaciens*, *Oceanobacillus oncorhynchi*, *Bacillus licheniformis*, *Lactobacillus vini*, *Bacillus subtilis*, *Lactobacillus buchneri*, *Bacillus megaterium*, *Acetobacter pasteurianus*, and *Lactobacillus casei/paracasei*.

In further examples, the composition includes cells of microbial species including or consisting of each of *Lactobacillus delbrueckii*, *Azotobacter vinelandii*, *Clostridium pasteurianum*, *Streptomyces griseus*, *Pseudomonas* sp. (closely related to *P. entomophila*, *P. fluorescens*, and *P.

*putida*; for example, a microbial species with 16S rRNA sequence with at least 99% sequence identity to SEQ ID NO: 17), *Pseudomonas putida, Bacillus amyloliquefaciens, Bacillus licheniformis, Lactobacillus vini, Bacillus subtilis, Lactobacillus buchneri, Bacillus megaterium, Acetobacter pasteurianus, Clostridium beijerinckii, Lactobacillus casei/paracasei*, and *Bacillus flexus*.

In another example, the composition includes cells of microbial species including or consisting of each of *Lactobacillus delbrueckii, Azotobacter vinelandii, Clostridium pasteurianum, Paenibacillus chibensis, Streptomyces griseus, Pseudomonas* sp. (closely related to *P. entomophila, P. fluorescens*, and *P. putida*; for example, a microbial species with 16S rRNA sequence with at least 99% sequence identity to SEQ ID NO: 17), *Pseudomonas putida, Bacillus amyloliquefaciens, Oceanobacillus oncorhynchi, Paenibacillus lautus* (e.g., closely related to *Paenibacillus launtus* and *Paenibacillus* sp. (strain Y412MC10), for example, a microbial species with 16S rRNA sequence with at least 99% sequence identity to SEQ ID NO: 12), *Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus*.

In another example, the composition includes cells of microbial species including or consisting of each of *Clostridium beijerinckii, Streptomyces griseus*, and *Bacillus flexus*.

In particular examples, combinations of these compositions are utilized to produce the compositions disclosed herein, for example, by mixing and co-fermenting two of the compositions.

One of ordinary skill in the art will recognize that identification of microbes, particularly at the species or strain level, is not always possible. As discussed in Example 1, the microbes in the compositions described herein were analyzed by 16S rDNA sequencing and whole genome sequencing followed by comparison to sequences in public databases. However, due to limitations of information in sequence databases (including little or no information for some species or strains and/or changes in nomenclature over time) it can be challenging to provide definitive species or strain identifications. Thus, in some embodiments, the microbial species included in the disclosed compositions are identified by their sequence identity to the 16S rDNA sequences provided herein (SEQ ID NOs: 3-24).

In some examples, the composition includes cells of microbial species including or consisting of microbes with 16S rDNA sequences having at least 95% sequence identity (such as at least 96%, at least 97%, at least 98%, at least 99%, or even 100% sequence identity) to each of SEQ ID NOs: 3-24. In another example, the composition includes cells of microbial species including or consisting of microbes with 16S rDNA sequences having at least 95% sequence identity (such as at least 96%, at least 97%, at least 98%, at least 99%, or even 100% sequence identity) to each of SEQ ID NOs: 3-7 and 9-24 or including or consisting of cells of microbes with 16S rDNA sequences having at least 95% sequence identity (such as at least 96%, at least 97%, at least 98%, at least 99%, or even 100% sequence identity) to each of SEQ ID NOs: 3-7, 10, 11, 13-18, and 20-24. In other examples, the composition includes cells of microbial species including or consisting of microbes with 16S rDNA sequences having at least 95% sequence identity (such as at least 96%, at least 97%, at least 98%, at least 99%, or even 100% sequence identity) to each of SEQ ID NOs: 3-8, 10, 11, 14, 16-18, 20-22, and 24 or includes cells of microbial species including or consisting of microbes with 16S rDNA sequences having at least 95% sequence identity (such as at least 96%, at least 97%, at least 98%, at least 99%, or even 100% sequence identity) to each of SEQ ID NOs: 3-14, 16-22, and 24.

In some embodiments, the composition includes cells of microbial species including or consisting of the collection of microbes deposited with the American Type Culture Collection (ATCC, 10801 University Boulevard Manassas, Va. 20110-2209) on Jul. 1, 2016 and assigned deposit number PTA-123288 (*Lactobacillus delbrueckii, Virgibacillus halophilus, Azotobacter vinelandii, Clostridium pasteurianum, Paenibacillus lautus, Paenibacillus chibensis, Paenibacillus cookii, Pseudomonas* sp., *Pseudomonas putida, Oceanobacillus oncorhynchi, Bacillus licheniformis, Lactobacillus vini, Lactobacillus buchneri, Lactobacillus casei/paracasei, Bacillus amyloliquefaciens, Bacillus megaterium, Bacillus subtilis, Bacillus* sp., and *Acetobacter pasteurianus*) or PTA-123289 (*Clostridium beijerinckii, Streptomyces griseus*, and *Bacillus flexus*), or deposited with ATCC on Jul. 8, 2016 and assigned deposit number PTA-123298 (*Lactobacillus delbrueckii, Virgibacillus halophilus, Azotobacter vinelandii, Clostridium pasteurianum, Pseudomonas* sp., *Pseudomonas putida, Oceanobacillus oncorhynchi, Bacillus licheniformis, Lactobacillus vini, Lactobacillus buchneri, Lactobacillus casei/paracasei, Bacillus amyloliquefaciens, Bacillus megaterium, Bacillus subtilis, Bacillus* sp., and *Acetobacter pasteurianus*). In some examples, the composition includes cells of microbial species including or consisting of the microbial species in two or more of the disclosed ATCC deposits, for example microbial species in ATCC deposit numbers PTA-123288 and PTA-123289 or microbial species in ATCC deposit numbers PTA-123298 and PTA-123289.

In additional embodiments, the composition includes cells of a combination of microbial species providing desirable metabolic characteristics or activities (for example, one or more activities that can promote plant growth). Thus, in some examples, the composition includes cells of at least one microbial species with nitrogen metabolism activity (such as denitrification, nitrogen fixation, and/or urease production), cells of at least one microbial species that is salt tolerant (for example, growth at 72 hours in medium containing 1%, 2.5%, 5%, 7.5%, or 10% salt), cells of at least one microbial species with phosphate and/or calcium and/or zinc salt solubilization activity, cells of at least one microbial species with cellulolytic and/or chitinolytic activity (such as GlcNAc degradation, chitin degradation, and/or cellobiose degradation), cells of at least one microbial species with malic acid metabolism activity (such as malic acid assimilation), cells of at least one microbial species with phytohormone (such as indole (auxin)) production activity, cells of at least one microbial species with iron metabolizing activity (such as iron binding activity (siderophores)), and/or cells of at least one microbial species with dephosphorylation of organic phosphate activity.

The composition may include cells of microbial species with one or more (such as 2 or more, 3 or more, 4 or more, 5 or more, 6 or more, 7 or more, or all) of the above-referenced characteristics or functions, as well as other desired characteristics or functions. In particular examples, the microbial composition includes cells of three or more microbial species each with at least one of the disclosed functionalities. In some examples, the composition includes cells of at least one microbial species with nitrogen metabolism activity and cells of at least one microbial species with salt tolerance; or cells of at least one microbial species with nitrogen metabolism activity, cells of at least one microbial species with salt tolerance, and cells of at least one microbial species with calcium and/or phosphate solubilizing activity; or cells of at least one microbial species with nitrogen metabolism activity, cells of at least one microbial species with salt tolerance, cells of at least one microbial species with calcium and/or phosphate and/or zinc salt solubilizing activity, and cells of at least one microbial species with cellulolytic/chitinolytic activity; or cells of at least one microbial species with nitrogen metabolism activity, cells of at least one microbial species with salt tolerance, cells of at least one microbial species with calcium and/or phosphate and/or zinc salt solubilizing activity, cells of at least one microbial species with cellulolytic/chitinolytic activity, and cells of at least one microbial species with malic acid metabolism activity; or cells of at least one microbial species with nitrogen metabolism activity, cells of at least one microbial species with salt tolerance, cells of at least one microbial species with calcium and/or phosphate and/or zinc salt solubilizing activity, cells of at least one microbial species with cellulolytic/chitinolytic activity, and cells of at least one microbial species with malic acid metabolism activity, and cells of at least one microbial species with phytohormone producing activity; or cells of at least one microbial species with nitrogen metabolism activity, cells of at least one microbial species with salt tolerance, cells of at least one microbial species with calcium and/or phosphate and/or zinc salt solubilizing activity, cells of at least one microbial species with cellulolytic/chitinolytic activity, and cells of at least one microbial species with malic acid metabolism activity, and cells of at least one microbial species with phytohormone producing activity, and cells of at least one microbial species with iron metabolizing activity; or cells of at least one microbial species with nitrogen metabolism activity, cells of at least one microbial species with salt tolerance, cells of at least one microbial species with calcium and/or phosphate and/or zinc salt solubilizing activity, cells of at least one microbial species with cellulolytic/chitinolytic activity, and cells of at least one microbial species with malic acid metabolism activity, and cells of at least one microbial species with phytohormone producing activity, cells of at least one microbial species with iron metabolizing activity, and cells of at least one microbial species with dephosphorylation of organic phosphate activity. These combinations of microbial species with the specified activities are only examples, and any factorial combination of the recited activities is contemplated herein. As discussed herein, a single microbial species may have more than one of the listed activities, thus, in some examples a composition including cells with a given number of the listed activities will not necessarily have cells of that number of different microbial species.

Exemplary methods for determining microbial cell metabolic characteristics or functions and identification of microbial species with particular characteristics are described in Example 3. One of ordinary skill in the art will recognize that a single microbial species may have more than one of these characteristics (for example, Table 11, below). In the examples described below, microbial species are identified by name; these identifications include microbial species with 16S rDNA with at least 95% (such as at least 96%, 97%, 98%, 99%, or even 100%) sequence identity to the sequences associated with each of these named species disclosed herein as SEQ ID NOs: 3-24.

Thus, in some embodiments the disclosed compositions include cells of at least one (such as at least 2, at least 3, at least 4, at least 5, at least 6, at least 7, at least 8, at least 9, at least 10, or more) microbial species with nitrogen metabolism activity, for example, at least one of *Acetobacter pasteurianus, Azotobacter vinelandii, Bacillus megaterium, Bacillus subtilis, Bacillus licheniformis, Oceanobacillus oncorhynchi, Bacillus amyloliquefaciens, Bacillus flexus, Virgibacillus halophilus, Clostridium beijerinckii, Clostridium pasteurianum, Paenibacillus cookii, Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12), *Pseudomonas* sp. (closely related to *P. entomophila, P. fluorescens,* and *P. putida,* for example, a microbial species with 16S rRNA sequence with at least 99% sequence identity to SEQ ID NO: 17), and *Streptomyces griseus*. In other examples, the disclosed compositions include cells of at least one (such as at least 2, at least 3, at least 4, at least 5, at least 6, at least 7, at least 8, at least 9, at least 10, or more) microbial species salt tolerant to 5% NaCl, for example *Bacillus megaterium, Bacillus subtilis, Bacillus licheniformis, Oceanobacillus oncorhynchi, Bacillus amyloliquefaciens, Bacillus* sp. (closely related to *B. kochii, B. pocheonensis,* and *Bacillus* sp. (strain R-27341), for example, a microbial species with a 16S rRNA sequence with at least 99% sequence identity to SEQ ID NO: 15), *Bacillus flexus. Lactobacillus casei/paracasei, Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12), *Pseudomonas putida,* and *Pseudomonas* sp. (closely related to *P. entomophila, P. fluorescens,* and *P. putida,* for example, a microbial species with 16S rRNA sequence with at least 99% sequence identity to SEQ ID NO: 17). In other examples, the disclosed compositions include cells of at least one (such as at least 2, at least 3, at least 4, at least 5, at least 6, at least 7, or more) microbial species with phosphate and/or calcium and/or zinc solubilization activity, for example, at least one of *Clostridium beijerinckii, Clostridium pasteurianum, Lactobacillus casei/paracasei, Lactobacillus buchneri, Lactobacillus vini, Lactobacillus delbrueckii,* and *Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12). In additional examples, the disclosed compositions include cells of at least one (such as at least 2, at least 3, at least 4, at least 5, at least 6, at least 7, at least 8, at least 9, at least 10, or more) microbial species with cellulolytic and/or chitinolytic activity, for example, one or more of *Bacillus megaterium, Bacillus subtilis, Bacillus amyloliquefaciens, Bacillus* sp. (closely related to *B. kochii, B. pocheonensis,* and *Bacillus* sp. (strain R-27341), for example, a microbial species with a 16S rRNA sequence with at least 99% sequence identity to SEQ ID NO: 15), *Bacillus flexus, Clostridium beijerinckii, Clostridium pasteurianum, Lactobacillus casei/paracasei, Lactobacillus vini, Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12), *Paenibacillus chibensis,* and *Streptomyces griseus.* In other examples, the disclosed compositions include cells of at least one (such as at least 2, at least 3, at least 4, at least 5, at least 6, or more) microbial species with malic acid metabolism activity, for example, at least one of *Bacillus megaterium, Bacillus subtilis, Bacillus licheniformis, Bacillus amyloliquefaciens, Bacillus* sp. (closely related to *B. kochii, B. pocheonensis*, and *Bacillus* sp. (strain R-27341), for example, a microbial species with a 16S rRNA sequence with at least 99% sequence identity to SEQ ID NO: 15), *Bacillus flexus, Paenibacillus cookii, Paenibacillus lautus* (e.g., closely related to *Paenibacillus lautus* and *Paenibacillus* sp. (strain Y412MC10), for example, a microbial species with 16S rRNA sequence with at least 99% sequence identity to SEQ ID NO: 12), *Paenibacillus chibensis, Pseudomonas putida, Pseudomonas* sp. (closely related to *P. entomophila, P. fluorescens*, and *P. putida*, for example, a microbial species with 16S rRNA sequence with at least 99% sequence identity to SEQ ID NO: 17), and *Streptomyces griseus*. In additional examples, the disclosed compositions include cells of at least one (such as at least 2, at least 3, or more) microbial species with phytohormone (e.g., indole (auxin)) production activity, for example, at least one of *Clostridium pasteurianum, Lactobacillus vini*, and *Lactobacillus buchneri*. In additional examples, the disclosed compositions include cells of at least one (such as at least 2, at least 3, or more) microbial species with iron metabolizing activity (e.g., iron binding activity), for example, at least one of *Clostridium pasteurianum* and *Clostridium beijerinckii*. Compositions including cells of microbial species with any combination of these characteristics or activities are contemplated herein.

In additional embodiments, any of the microbial compositions disclosed herein can further include cells of one or more (such as 2 or more, 3 or more, 4 or more, or all) of *Desulfosporosinus meridiei, Nitrosopumilus* sp., *Marinobacter bryozoorum, Leptospirillum ferrodiazotrophum*, and *Lactobacillus acidophilus*.

The disclosed compositions may include one or more further components in addition to the microbes, including but not limited to salts, metal ions, and/or buffers (for example, one or more of $KH_2PO_4$, $K_2HPO_4$, $CaCl_2$, $MgSO_4$, $FeCl_3$, $NaMoO_4$, and/or $Na_2MoO_4$), trace elements (such as sulfur, sulfate, sulfite, copper, or selenium), micronutrients (such as boron (B), zinc (Zn), manganese (Mn), iron (Fe), copper (Cu), molybdenum (Mo), chlorine (C)), vitamins (such as B vitamins or vitamin K), sugars (such as sucrose, glucose, or fructose), chitin, chitosan, glucosamine, protein, and/or one or more amino acids. Additional components that may also be included in the compositions include HYT B, HYT C, and/or HYT D, one or more fertilizers (e.g., liquid fertilizer), one or more pesticides, one or more fungicides, one or more herbicides, one or more insecticides, one or more plant hormones, one or more plant elicitors, or combinations of two or more of these components.

In some embodiments, the disclosed compositions are in a liquid medium (such as a culture or fermentation medium or storage medium) or inoculum. In other embodiments, the compositions are present on a solid or gelatinous medium (such as a culture plate) containing or supporting the microbes. In other examples, the disclosed compositions are freeze-dried and can be reconstituted by adding liquid (such as culture medium) and growing in a liquid medium or by streaking on solid medium.

In yet other embodiments, the compositions described herein are present in a dry formulation, such as a dry powder, pellet, or granule. Dry formulations can be prepared by adding an osmoprotectant (such as a sugar, for example, trehalose and/or maltodextrin) to a microbial composition in solution at a desired ratio. This solution is combined with dry carrier or absorptive agent, such as wood flour or clay, at the desired concentration of microbial composition (such as 2-30%, for example, 2.5-10%, 5-15%, 7.5-20%, or 15-30%). Granules can be created by incorporating clay or polymer binders that serve to hold the granules together or offer specific physical or degradation properties. Exemplary methods of forming granules include rotary granulation, mixer granulation, or extrusion. In further examples, dry formulations are produced by spraying or soaking a liquid microbial composition described herein on/in a solid carrier such as bentonite or coating the liquid microbial composition directly on a fertilizer granule. In further examples, dry formulations include compositions including cells of one or more of the microbial species disclosed herein (or any combination thereof) that has been lyophilized (freeze-dried). Additional methods for preparing dry formulations including one or more microbial species are known to one of ordinary skill in the art, for example as described in *Formulation of Microbial Biopesticides: Beneficial Microorganisms, Nematodes and Seed Treatments*, Burges, ed., Springer Science, 1998.

In some examples, composition is maintained at a temperature supporting growth of the microbes, for example at about 25-45° C. (such as about 30-35° C., about 30-40° C., or about 35-40° C.). In other examples, the composition is stored at temperatures at which the microbes are not growing or are inactive, such as less than 25° C. (for example, 20° C., 15° C., 10° C., 4° C., −20° C., −40° C., −70° C., or below). One of skill in the art can formulate the compositions for cold storage, for example by including stabilizers (such as glycerol). In still further examples, the composition is stored at ambient temperatures, such as about 0-35° C. (for examples, about 10-30° C. or about 15-25° C.).

B. Methods of Producing Defined Compositions

In some embodiments, the disclosed compositions are produced by co-culture or co-cultivation of cells of two or more of the disclosed microbial species (such as 2 or more 3 or more, 4 or more, 5 or more, 6 or more, 7 or more, 8 or more, 9 or more, 10 or more, 11 or more, 12 or more 13 or more, 14 or more, 15 or more, 16 or more 17 or more 18 or more, 19 or more, 20 or more, 21 or more, or 22 or more microbial species). In examples where fewer than all of the microbial species in the composition are co-cultured, the composition is produced by combining two or more co-cultured subsets (sub-compositions) of the microbial species in the composition. Additional components (e.g., non-microbial components) may be present during the production of the mixture of microbial species (full set or subset(s)) or may be added after production of the mixture of the microbial species in the composition.

In some examples, the disclosed compositions are produced by co-culture of all of the microbial species in the composition. Thus, in one example, a disclosed composition is produced by co-culture of cells of each of *Lactobacillus delbrueckii, Virgibacillus halophilus, Azotobacter vinelandii, Clostridium pasteurianum, Paenibacillus chibensis, Streptomyces griseus, Pseudomonas* sp. (closely related to *P. entomophila, P. fluorescens*, and *P. putida*, for example, a microbial species with 16S rRNA sequence with at least 99% sequence identity to SEQ ID NO: 17), *Pseudomonas putida, Bacillus* sp. (closely related to *B. kochii, B. pocheonensis*, and *Bacillus* sp. (strain R-27341), for example, a microbial species with a 16S rRNA sequence with at least 99% sequence identity to SEQ ID NO: 15), *Bacillus amyloliquefaciens, Oceanobacillus oncorhynchi, Paeniba-* cillus lautus, Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei, and Bacillus flexus. In another example, a disclosed composition is produced by co-culture of cells of each of Lactobacillus delbrueckii, Virgibacillus halophilus, Azotobacter vinelandii, Clostridium pasteurianum, Streptomyces griseus, Pseudomonas sp. (closely related to P. entomophila, P. fluorescens, and P. putida, for example, a microbial species with 16S rRNA sequence with at least 99% sequence identity to SEQ ID NO: 17), Pseudomonas putida, Bacillus sp. (closely related to B. kochii, B. pocheonensis, and Bacillus sp. (strain R-27341), for example, a microbial species with a 16S rRNA sequence with at least 99% sequence identity to SEQ ID NO: 15), Bacillus amyloliquefaciens, Oceanobacillus oncorhynchi, Bacillus licheniformis, Lactobacillus vini, Bacillus subtilis, Lactobacillus buchneri, Bacillus megaterium, Acetobacter pasteurianus, Clostridium beijerinckii, Lactobacillus casei/paracasei, and Bacillus flexus. In additional examples, a disclosed composition is produced by co-culture of cells of each of Lactobacillus delbrueckii, Virgibacillus halophilus, Azotobacter vinelandii, Clostridium pasteurianum, Paenibacillus chibensis, Streptomyces griseus, Pseudomonas sp. (closely related to P. entomophila, P. fluorescens, and P. putida, for example, a microbial species with 16S rRNA sequence with at least 99% sequence identity to SEQ ID NO: 17), Pseudomonas putida, Bacillus sp. (closely related to B. kochii, B. pocheonensis, and Bacillus sp. (strain R-27341), for example, a microbial species with a 16S rRNA sequence with at least 99% sequence identity to SEQ ID NO: 15), Bacillus amyloliquefaciens, Oceanobacillus oncorhynchi, Paenibacillus lautus, Bacillus licheniformis, Lactobacillus vini, Paenibacillus cookii, Lactobacillus buchneri, Bacillus megaterium, Acetobacter pasteurianus, Clostridium beijerinckii, Lactobacillus casei/paracasei, and Bacillus flexus. In another example, a disclosed composition is produced by co-culture of cells of each of Lactobacillus delbrueckii, Virgibacillus halophilus, Azotobacter vinelandii, Clostridium pasteurianum, Streptomyces griseus, Pseudomonas sp. (closely related to P. entomophila, P. fluorescens, and P. putida, for example, a microbial species with 16S rRNA sequence with at least 99% sequence identity to SEQ ID NO: 17), Pseudomonas putida, Bacillus sp. (closely related to B. kochii, B. pocheonensis, and Bacillus sp. (strain R-27341), for example, a microbial species with a 16S rRNA sequence with at least 99%/o sequence identity to SEQ ID NO: 15), Bacillus amyloliquefaciens, Oceanobacillus oncorhynchi, Bacillus licheniformis, Lactobacillus vini, Lactobacillus buchneri, Bacillus megaterium, Acetobacter pasteurianus, Clostridium beijerinckii, Lactobacillus casei/paracasei, and Bacillus flexus.

In another example, a disclosed composition is produced by co-culture of cells of each of Lactobacillus delbrueckii, Azotobacter vinelandii, Clostridium pasteurianum, Streptomyces griseus, Pseudomonas sp., Pseudomonas putida, Bacillus amyloliquefaciens, Bacillus licheniformis, Lactobacillus vini, Bacillus subtilis, Lactobacillus buchneri, Bacillus megaterium, Acetobacter pasteurianus, Clostridium beijerinckii, Lactobacillus casei/paracasei, and Bacillus flexus. In other examples, a disclosed composition is produced by co-culture of cells of each of Lactobacillus delbrueckii, Azotobacter vinelandii, Clostridium pasteurianum, Paenibacillus chibensis, Streptomyces griseus, Pseudomonas sp., Pseudomonas putida, Bacillus amyloliquefaciens, Oceanobacillus oncorhynchi, Paenibacillus lautus, Bacillus licheniformis, Lactobacillus vini, Paenibacillus cookii, Bacillus subtilis, Lactobacillus buchneri, Bacillus megaterium. Acetobacter pasteurianus, Clostridium beijerinckii, Lactobacillus casei/paracasei, and Bacillus flexus.

Culture media that can be used to produce these compositions by co-culture is described in Example 2, and includes, but is not limited to a medium including 2% molasses (w/v), 1× phosphate buffered saline (PBS), 0.1% whey proteins (w/v), and 0.25% Ferti-Nitro Plus (w/v). In other examples, the medium for co-culture of the microbial cells includes phosphate buffer saline (1×), Black strap molasses (2-10% w/v), whey proteins (0.1-0.5% w/v), Ferti-Nitro Plus Plant N (0.25-1.25% w/v), with or without kelp extract (0.0067%), yeast powder (0.0033% w/v), and/or spirulina (0.0067% w/v).

In other examples, the disclosed compositions are produced by co-culturing cells of at least two subsets of microbial species and then combining the two co-cultures to produce the composition. In one example, the composition is produced by co-culturing cells of Lactobacillus delbrueckii, Virgibacillus halophilus, Azotobacter vinelandii, Clostridium pasteurianum, Paenibacillus chibensis, Pseudomonas sp. (closely related to P. entomophila, P. fluorescens, and P. putida, for example, a microbial species with 16S rRNA sequence with at least 99% sequence identity to SEQ ID NO: 17), Pseudomonas putida, Bacillus sp. (closely related to B. kochii, B. pocheonensis, and Bacillus sp. (strain R-27341), for example, a microbial species with a 16S rRNA sequence with at least 99% sequence identity to SEQ ID NO: 15), Bacillus amyloliquefaciens, Oceanobacillus oncorhynchi, Paenibacillus lautus, Bacillus licheniformis, Lactobacillus vini, Paenibacillus cookii, Bacillus subtilis, Lactobacillus buchneri, Bacillus megaterium, Acetobacter pasteurianus, and Lactobacillus casei/paracasei (group of 19 microbial species) and separately co-culturing Clostridium beijerinckii, Streptomyces griseus, and Bacillus flexus (group of 3 microbial species).

In another example, the composition is produced by co-culturing Lactobacillus delbrueckii, Virgibacillus halophilus, Azotobacter vinelandii, Clostridium pasteurianum, Pseudomonas sp. (closely related to P. entomophila, P. fluorescens, and P. putida, for example, a microbial species with 16S rRNA sequence with at least 99% sequence identity to SEQ ID NO: 17), Pseudomonas putida, Bacillus sp. (closely related to B. kochii, B. pocheonensis, and Bacillus sp. (strain R-27341), for example, a microbial species with a 16S rRNA sequence with at least 99% sequence identity to SEQ ID NO: 15), Bacillus amyloliquefaciens, Oceanobacillus oncorhynchi, Bacillus licheniformis, Lactobacillus vini, Bacillus subtilis, Lactobacillus buchneri, Bacillus megaterium, Acetobacter pasteurianus, and Lactobacillus casei/paracasei (group of 16 microbial species) and separately co-culturing Clostridium beijerinckii, Streptomyces griseus, and Bacillus flexus. Following individual co-culture of the two mixtures under conditions sufficient for growth of the microbes (such as those described in Example 2), the individual co-cultures are mixed to produce the composition.

In some examples, the medium used to co-culture the group of 19 microbial species or the group of 16 microbial species includes 10% molasses (w/v), 1×PBS, 0.5% whey proteins (w/v), and 1.25% Ferti-Nitro Plus (w/v). In some examples, the medium used to co-culture the group of 3 microbial species includes 2% molasses (w/v), 1×PBS, 0.1% whey proteins (w/v), and 0.25% Ferti-Nitro Plus. However, one of ordinary skill in the art can identify other media that are suitable for co-culture of the microbes, including various amounts of the listed ingredients, as described in Example 2. Following individual co-culture of the two mixtures under conditions sufficient for growth of the microbes (such as those described in Example 2), the individual co-cultures (such as the group of 19 microbes and the group of 3 microbes, or the group of 16 microbes and the group of 3 microbes) are mixed to produce the composition. In some examples, the two co-cultures are mixed at a ratio of 10:1 to 1:0.5 (such as 8:1 to 1:1, 5:1 to 2:1, 3:1 to 1:0.5) of the large group (group of 19 microbial species or group of 16 microbial species):small group (group of 3 microbial species). In some examples, the ratio of the co-cultures is about 10:1, 9:1, 8:1, 7:1, 6:1, 5:1, 4:1, 3:1, 2:1, 1:1, or 1:0.5. In particular embodiments, the ratio of the co-cultures is about 6.5:1, 1:1, 2:1, or 1:0.5. Similar co-culture media and mixtures can be utilized with co-cultures that are identical to those listed above, but do not include *Bacillus subtilis*.

In further examples, the composition is produced by separately culturing the microbes in ATCC deposit numbers PTA-123288 and PTA-123289 and mixing the individual cultures to produce the composition. In still further examples, the composition is produced by separately culturing the microbes in ATCC deposit numbers PTA-123298 and PTA-123289 and mixing the individual cultures to produce the composition.

III. Biodegradation Processes

The disclosed compositions can be used to degrade biological materials, such as chitin-rich materials, for example, aquatic animals or aquatic animal by-products, insects, or fungi. Thus, in some embodiments, disclosed herein are methods including mixing one or more of the disclosed microbial compositions with a chitin-containing biological material to form a mixture, and fermenting the mixture. In some embodiments, the methods also include separating the mixture into solid, aqueous, and optionally, lipid fractions (FIG. 1).

In some embodiments, a biodegradation process disclosed herein includes mixing a microbial composition disclosed herein with one or more chitin-containing biological materials. Chitin-containing biological materials include, but are not limited to, aquatic animals or aquatic animal by-products, insects, and fungi. In some examples, the chitin-containing biological material is an aquatic animal, such as an aquatic arthropod (for example, a member of Class Malacostraca). Aquatic arthropods for use in the disclosed methods include shrimp, crab, lobster, crayfish, and krill. In some examples, the entire aquatic animal (such as an aquatic arthropod) or aquatic animal by-products are used in the biodegradation methods disclosed herein. Aquatic animal by-products include any part of an aquatic animal, such as any part produced by processing of the aquatic animal. In some examples, an aquatic animal by-product is all or a portion of an aquatic animal exoskeleton, such as shrimp, crab, crayfish, or lobster shell. In other examples, an aquatic animal by-product is a part of an aquatic animal, for example, shrimp cephalothoraxes.

In other examples, the chitin-containing biological material includes fungi, such as fungi from Phylum Zygomycota, Basidiomycota, Ascomycota, or Deuteromycota. Particular exemplary fungi include *Aspergillus* spp., *Penicillium* spp., *Trichoderma* spp., *Saccharomyces* spp., and *Schizosaccharomyces* spp. Thus, baker, brewer, and distiller waste streams can provide sources for chitin-containing biological material. In still further examples, the chitin-containing biological material includes insects that contain chitin in their exoskeletons, such as grasshoppers, crickets, beetles, and other insects. Byproducts of the processing of such insects are also contemplated to be sources of chitin.

The chitin-containing biological material is mixed with a composition described in Section II above to form a substantially homogeneous mixture. In some examples, the chitin-containing biological material is ground, crushed, minced, milled, or otherwise dispersed prior to mixing with the microbial composition described herein. In particular examples, the mixture contains about 10-50% (such as about 10-20%, about 20-30%, about 30-40%, about 25-40%, for example about 25%, about 30%, about 35%, about 40%, about 45%, or about 50%) chitin-containing material (such as shrimp heads) (w/v) in inoculum containing about 0.1-5% (such as about 0.1-1% about 0.5-2%, about 1-2%, about 2-3%, about 0.1%, about 0.2%, about 0.3%, about 0.5%, about 0.8%, about 1%, about 1.25%, about 1.5%, about 1.75%, about 2%, about 2.5%, about 3%, about 4%, or about 5%) of the microbial composition (v/v).

In some examples, the inoculum, chitin-containing biological material, and a sugar (or other carbon source) are mixed together, for example by stirring or agitation. In other examples, one or more of the microbes in the microbial composition is optionally activated prior to mixing with the chitin-containing biological material and fermentation. Activation is not required for the methods disclosed herein. Adjustments to the time and/or temperature of the fermentation can be made by one of skill in the art, depending on whether the microbes are activated prior to fermentation. Activation of the microbe(s) can be by incubating an inoculum of the microbial composition with a carbon source (such as a sugar, for example, glucose, sucrose, fructose, or other sugar) at a temperature and for a sufficient period of time for the microbes to grow. In some examples, an inoculum of the microbes (such as a microbial composition described herein) has a concentration of about 0.05-5% v/v (for example, about 0.5-5%, about 0.5-2%, about 1-2%, or about 2-3%) in a liquid medium. The inoculum is diluted in a solution containing about 0.1-1% sugar (for example, about 0.1-0.5%, about 0.1-0.3%, about 0.2-0.6%, or about 0.5-1%, such as about 0.1%, about 0.2%, about 0.3%, about 0.4%, about 0.5%, about 0.6%, about 0.7%, about 0.8%, about 0.9%, or about 1%) and incubated at ambient temperatures, for example about 20-40° C. (such as about 20° C., about 25° C., about 30° C., about 35° C., or about 40° C.) for about 1-5 days (such as about 24 hours, about 48 hours, about 72 hours, about 96 hours, or about 120 hours). In other examples, activation of the microbe(s) can be activated by incubating an inoculum of the microbial composition at a temperature and for a sufficient period of time for the microbes to grow, for example, incubation at about 20-40° C. (such as about 25-35° C.) for 12 hours to 5 days (such as 1-4 days or 2-3 days). In some non-limiting examples, the microbes are considered to be activated when the culture reaches an optical density of >0.005 at 600 nm.

After mixing of the chitin-containing biological material and the microbial composition (which is optionally activated), the mixture is fermented. In some examples, the pH of the mixture is measured prior to fermentation. The pH is adjusted to a selected range (e.g., pH about 3 to about 4 or about 3.5 to 4), if necessary, prior to fermentation. The mixture is incubated at a temperature of about 20-40° C. (for example, about 30°-36° C., such as about 30° C., about 31° C., about 32° C., about 33° C., about 34° C., about 35° C., about 36° C., about 37° C., about 38° C., about 39° C., or about 40° C.) for about 1-30 days (such as about 3-28 days, about 7-21 days, about 3, 5, 7, 10, 14, 16, 20, 24, 28, or 30 days). The mixture is agitated periodically (for example, non-continuous agitation). In some examples, the mixture is agitated for a period of time every 1-7 days, for example every 1, 2, 3, 4, 5, 6, or 7 days. In some non-limiting examples, the fermentation proceeds until the titratable acidity (TTA) is about 3-5% and the pH is about 4-5.

Following the fermentation, the resulting fermented mixture is separated into at least solid and liquid fractions. In some examples, the solid fraction is referred to as "HYT C" and in some examples, the liquid fraction is referred to as "HYT B." In some examples, the fermentation is passed from the tank to settling equipment. The liquid is subsequently decanted and centrifuged. In one non-limiting example, the fermented mixture is centrifuged at 1250 rpm (930×g) for 15 minutes at about 5° C. to obtain liquid and lipid (e.g., pigment) fractions. The liquid (or aqueous) fraction obtained from the biodegradation process can be stored at ambient temperature. In some non-limiting examples, a sugar is added to the liquid fraction, for example at 1-10% v/v.

The liquid fraction may include components such as protein, amino acids, glucosamine, trace elements (such as calcium, magnesium, zinc, copper, iron, and/or manganese), and/or enzymes (such as lactic enzymes, proteases, lipases, and/or chitinases). In some non-limiting examples, the liquid fraction contains (w/v) about 1-5% total amino acids, about 3-7% protein, about 0.1-2% nitrogen, less than about 0.2% phosphorus, about 0.5-1% potassium, about 4-8% carbon, about 0.2-1% calcium, less than about 0.2% magnesium, less than about 0.2% sodium, and/or about 0.1-0.4% sulfur. In additional non-limiting examples, the liquid fraction includes about 0.01-0.2% glucosamine (for example, about 0.1% or less). The liquid fraction also may contain one or more microbes (e.g., from the inoculum used to start the fermentation process) and/or trace amounts of chitosan or chitin. The liquid fraction is in some examples referred to herein as "HYT B."

The solid fraction obtained from the biodegradation process contains chitin (for example, about 50-70% or about 50-60% chitin). The solid fraction may also contain one or more of trace elements (such as calcium, magnesium, zinc, copper, iron, and/or manganese), protein or amino acids, and/or one or more microbes from the inoculum used to start the fermentation process. The solid fraction is in some examples referred to herein as "HYT C." HYT C is optionally micronized to form micronized chitin and residual chitin. In some non-limiting examples, the solid fraction contains (w/v) about 9-35% total amino acids, about 30-50% crude protein, about 5-10% nitrogen, about 0.3-1% phosphorus, less than about 0.3% potassium, about 35-55% carbon, about 0.5-2% calcium, less than about 0.1% magnesium, about 0.1-0.4% sodium, and/or about 0.2-0.5% sulfur.

In some examples, a lipid fraction is also separated from the solid and liquid fractions. The lipid fraction is the upper phase of the liquid fraction. The lipid fraction contains compounds such as sterols, vitamin A and/or vitamin E, fatty acids (such as DHA and/or EHA), and in some examples, carotenoid pigments (for example, astaxanthin). The lipid fraction may be used for a variety of purposes, including but not limited to production of cosmetics or nutritional products.

In additional embodiments, chitin is fermented with a disclosed microbial composition. In some examples chitin (such as HYT C, or micronized and/or residual chitin produced as described above) is mixed with a microbial consortium or composition containing microbes described herein and protein hydrolyzate (e.g., HYT B), and fermented to form a fermented mixture. At least a portion of the chitin in the starting mixture is digested as a result of the fermentation. In some examples, the mixture is incubated at a temperature of about 20-40° C. (for example, about 30°-35° C., such as about 30° C., about 31° C., about 32° C., about 33° C., about 34° C., about 35° C., about 36° C., about 37° C., about 38° C., about 39° C., or about 40° C.) for about 1 day to 30 days (such as about 2-28 days, about 4-24 days, about 16-30 days, about 10-20 days, or about 12-24 days). In some examples, the mixture is agitated periodically (for example, non-continuous agitation). In other examples, the mixture is continuously agitated. In one non-limiting example, the mixture is agitated for about 1-12 hours daily (such as about 2-8 hours or about 4-10 hours). The pH of the fermentation mixture may be monitored periodically. In some examples, the pH is optionally maintained at about 4-5. In some examples, the fermentation proceeds until Total Titratable Acidity (TTA) is at least about 1-10% (such as about 2-8%, about 4-8%, or about 5-10%).

Following the fermentation, the resulting fermented mixture is separated into at least solid and liquid fractions, for example by decanting, filtration, and/or centrifugation. The liquid fraction resulting from fermentation of HYT B and chitin with the microbial composition is in some examples referred to herein as "HYT D." In some non-limiting examples, the liquid fraction contains (w/v) about 0.5-2% total amino acids, about 3-7% protein, about 0.5-1% nitrogen, less than about 0.1% phosphorus, about 0.4-1% potassium, about 3-7% carbon, less than about 0.5% calcium, less than about 0.1% magnesium, less than about 0.3% sodium, and/or about less than about 0.3% sulfur. In addition, HYT D contains less than about 50% chitin (such as less than about 45%, less than about 40%, less than about 35%, or less than about 30% chitin) and less than 2% glucosamine (such as less than about 1.5% or less than about 1% glucosamine). In other examples, HYT D contains about 25-50% chitin and about 0.5-2% glucosamine.

IV. Processes for Treating Soil, Plants, and/or Seeds

The disclosed microbial compositions, alone or in combination with products disclosed herein (such as HYT B, HYT C, and/or HYT D), can be used to treat soil, plants, or plant parts (such as roots, stems, foliage, seeds, or seedlings). Methods of producing HYT B, HYT C, and HYT D are described in Section III (above) and also in U.S. Pat. No. 8,748,124 and International Pat. App. Publ. No. WO 2012/175738, both of which are incorporated herein by reference in their entirety.

In some examples, treatment with the disclosed compositions improve plant growth, improve stress tolerance, and/or increase crop yield. In some embodiments the methods include contacting soil, plants (such as plant foliage, stems, roots, seedlings, or other plant parts), or seeds with a microbial or composition disclosed herein. The methods may also include growing the treated plants, plant parts, or seeds and/or cultivating plants, plant parts, or seeds in the treated soil.

Microbes is the composition are optionally activated before application. In some examples, activation of the microbe(s) is as described in Section III, above. In other examples, microbe(s) are activated by mixing 100 parts water and 1 part microbial composition and incubating at about 15-40° C. (such as about 20-40° C., about 15-30° C., or about 25-35° C.) for about 12 hours-14 days (such as about 1-14 days, 3-10 days, 3-5 days, or 5-7 days). The activation mixture optionally can also include 1 part HYT B, if the microbial composition is to be applied in combination with HYT B.

In other embodiments, the methods include contacting soil, plants, plant parts, or seeds with a disclosed composition and one or more of HYT B, HYT C, and HYT D (such as one, two, or all of HYT B, HYT C, and HYT D). HYT B, HYT C, and/or HYT D may be separately applied to the soil, plants (or plant parts), and/or seeds, for example sequentially, simultaneously, or substantially simultaneously with the disclosed microbial compositions.

In some examples, the methods include contacting the soil, plants (or plant part), or seeds with a disclosed microbial composition and one or more additional components, including but not limited to chitin, chitosan, glucosamine, protein, amino acids, liquid fertilizer, one or more pesticides, one or more fungicides, one or more herbicides, one or more insecticides, one or more plant hormones, one or more plant elicitors, or combinations of two or more thereof. The additional components may be included in the composition including the microbes disclosed herein, or may be separately applied to the soil, plants (or plant parts), and/or seeds, for example sequentially, simultaneously, or substantially simultaneously with the disclosed compositions.

In particular embodiments, the microbial composition is combined with a liquid fertilizer (for example an aqueous solution or suspension containing soluble nitrogen). In some examples, the liquid fertilizer includes an organic source of nitrogen such as urea, or a nitrogen-containing inorganic salt such as ammonium hydroxide, ammonium nitrate, ammonium sulfate, ammonium pyrophosphate, ammonium thiosulfate or combinations thereof. Aqua ammonia (20-24.6% anhydrous ammonia) can also be used as the soluble nitrogen. In some examples, the microbial consortium or composition is combined with the liquid fertilizer (for example, mixed with the liquid fertilizer) immediately before use or a short time before use (such as within 10 minutes to 24 hours before use, for example, about 30 minutes, 1 hour, 2 hours, 3 hours, 4 hours, 6 hours, 8 hours, 12 hours, 16 hours, 18 hours, or 24 hours before use). In other examples, the microbial consortium or composition is combined with the liquid fertilizer (for example mixed with the liquid fertilizer) at least 24 hours before use (such as 24 hours to 6 months, for example, at least 36 hours, at least 48 hours, at least 72 hours, at least 96 hours, at least one week, at least two weeks, at least four weeks, at least eight weeks, or at least 12 weeks before use).

In some examples, the amount of the composition(s) to be applied (for example, per acre or hectare) is calculated and the composition is diluted in water (or in some examples, liquid fertilizer) to an amount sufficient to spray or irrigate the area to be treated (if the composition is a liquid). The composition can be applied at the time of seed planting at a rate of 0.5-2 liters per acre (such as 0.5 L/acre, 1 L/acre, 1.5 L/acre, or 2 L/acre). The microbial composition can also be applied to the soil (e.g., near the plant roots) or plant one or more times during growth, in the same or a different amount. In other examples, the composition can be mixed with diluted herbicides, insecticides, pesticides, or plant growth regulating chemicals. If the composition to be applied is a solid (such as a dry formulation), the solid can be applied directly to the soil, plants, or plant parts or can be suspended or dissolved in water (or other liquid) prior to use.

The disclosed microbial compositions (alone or in combination with other components disclosed herein) can be delivered in a variety of ways at different developmental stages of the plant, depending on the cropping situation and agricultural practices. In some examples, a disclosed microbial composition is mixed with liquid fertilizer and applied at the time of seed planting at a rate of 0.5-2 liters per acre (such as 0.5 L/acre, 1 L/acre, 1.5 L/acre, or 2 L/acre), or alternatively are applied individually. The microbial composition and liquid fertilizer can also be applied to the soil (e.g., near the plant roots) or plant one or more times during growth, in the same or a different amount. In other examples, a disclosed microbial composition and HYT B are mixed and diluted and applied at seed planting at a rate of 0.5-2 liters per acre (such as 0.5 L/acre, 1 L/acre, 1.5 L/acre, or 2 L/acre), or alternatively are applied individually. The microbial composition and HYT B can also be applied to the soil (e.g., near the plant roots) or plant one or more times during growth, in the same or a different amount.

In still further examples, a disclosed microbial composition and additional components (such as liquid fertilizer, HYT B, or other components) are diluted and delivered together through drip irrigation at low concentration as seedlings or transplants are being established, delivered in flood irrigation, or dispensed as a diluted mixture with nutrients in overhead or drip irrigation in greenhouses to seedlings or established plants, or alternatively are applied individually. In additional examples, a disclosed microbial composition is added to other soil treatments in the field, such as addition to insecticide treatments, to enable ease-of-use. In other examples, such as greenhouses, a disclosed microbial composition and HYT B are used individually or together, combined with liquid fertilizer (such as fish fertilizer) and other nutrients and injected into overhead water spray irrigation systems or drip irrigation lines over the course of the plant's growth. In one greenhouse example, a disclosed microbial composition and HYT B are used together, for example, diluted and applied during overhead irrigation or fertigation at a rate of 0.25 to 1 liter at seedling germination, followed by 0.25 to 1 liter mid-growth cycle with fertigation, and final 0.25 to 1 liter fertigation 5-10 days end of growth cycle.

In some embodiments, a disclosed microbial composition and HYT B are applied together or individually (for example sequentially) to promote yield, vigor, typeness, quality, root development, or stress tolerance in crops.

In all crops, HYT C may be added to the soil at a rate of about 0.5-2 kg/acre (such as about 0.5 kg/acre, about 1 kg/acre, about 1.5 kg/acre, or about 2 kg/acre) at the time of crop establishment or planting, for example in combination with a disclosed microbial composition. In other examples, HYT C is added to a drip irrigation solution of a disclosed microbial composition and HYT B is added to fertilization applications containing a disclosed microbial composition and HYT B in greenhouses, such as the examples above.

In additional embodiments, HYT D (alone or in combination with the microbial compositions or other components disclosed herein) is used at about 1-20 L/hectare (such as about 1-15 L/hectare, about 3-10 L/hectare, or about 3-5 L/hectare). In other examples, HYT D (alone or in combination with the microbial compositions or other components disclosed herein) is used as a seed treatment to enhance crop yield and performance (for example, about 1-10 L/kg seed, such as about 1-3 L/kg, about 3-5 L/kg, or about 5-10 L/kg). Alternatively, HYT D can be used in the soil (alone or in combination with the microbial compositions or other components disclosed herein) at about 1-3 L/hectare to increase plant growth, for example to help plants remain productive under conditions of stress.

In some examples, treatment of soil, seeds, plants, or plant parts with a disclosed composition increases plant growth (such as overall plant size, amount of foliage, root number, root diameter, root length, production of tillers, fruit production, pollen production, and/or seed production) by at least about 5% (for example, at least about 10%, at least about 30%, at least about 50%, at least about 75%, at least about 100%, at least about 2-fold, at least about 3-fold, at least about 5-fold, at least about 10-fold, or more). In other examples, the disclosed methods result in increased crop production by about 10-75% (such as about 20-60% or about 30-50%) compared to untreated crops. Other measures of crop performance include quality of fruit, yield, starch or solids content, sugar content or brix, shelf-life of fruit or harvestable product, production of marketable yield or target size, quality of fruit or product, grass tillering and resistance to foot traffic in turf, pollination and fruit set, bloom, flower number, flower lifespan, bloom quality, rooting and root mass, crop resistance to lodging, abiotic stress tolerance to heat, drought, cold and recovery after stress, adaptability to poor soils, level of photosynthesis and greening, and plant health. To determine efficacy of products, controls include the same agronomic practices without addition of microbes, performed in parallel.

The disclosed methods and compositions can be used in connection with any crop (for example, for direct crop treatment or for soil treatment prior to or after planting). Exemplary crops include, but are not limited to alfalfa, almond, banana, barley, broccoli, cabbage, canola, carrots, citrus and orchard tree crops, corn, cotton, cucumber, flowers and ornamentals, garlic, grapes, hops, horticultural plants, leek, melon, oil palm, onion, peanuts and legumes, pineapple, poplar, pine and wood-bearing trees, potato, raspberry, rice, sesame, sorghum, soybean, squash, strawberry, sugarcane, sunflower, tomato, turf and forage grasses, watermelon, wheat, and eucalyptus.

V. Examples

The following examples are provided to illustrate certain particular features and/or embodiments. These examples should not be construed to limit the disclosure to the particular features or embodiments described.

Example 1

Isolation and Identification of Microbes

This example describes isolation, identification, and characterization of microbes.

Isolation of Microbes:

Samples of HYT A (Agrinos AS; 50 mL to 5 L) were stored at room temperature away from light. Before sampling from a selected HYT A batch, the corresponding container was vigorously mixed to ensure the contents were evenly distributed, as a sedimentation usually occurs over time. Typically, a 1-10 mL aliquot was retained for the purpose of microbial isolation. In the case of *Azotobacter*, isolation was conducted from soil samples (obtained at N 38° 32' 49.55", W 121° 44' 13.54").

Isolation Through Spread Plating:

From retained HYT A aliquots, 0.1 mL was aseptically collected and mixed with 9.9 mL of sterile water or Peptone water in a culture tube ($10^{-2}$ dilution). The tubes were then vortexed (e.g., 60 seconds at 2,000 rpm) and 10-fold serial dilutions were prepared in water or peptone water (up to the 1:$10^9$ dilution). One hundred microliters of each dilution was subsequently spread on semi-solid media in 100 mm Petri plates using a sterile L-shaped spreader. Plates containing Standard Method Agar (SMA; BD #247940), Nutrient Agar (NA; BD #213000) or other selected growth medium (Table 1) were used. The inoculated plates were then incubated in temperature controlled chambers at 22° C. to 35° C. For isolation of anaerobic microbes, plates were first placed in anaerobic boxes (e.g. BD GasPak™ EZ Container Systems, BD Diagnostics) before incubation at the desired temperature(s).

TABLE 1

Semi-solid media used to isolate microbes from HYT A

| Genus | Semi-solid Medium * |
|---|---|
| *Bacillus* spp. | NA (*amyloliquefaciens, flexus*), YPD (*subtilis; pocheonensis*), SMA (*licheniformis*), AMA (*megaterium; licheniformis*), AMAG |
| *Lactobacillus* spp. | YPD (*casei/paracasei; buchneri*), MRS (*vini*), NA (*lautus; buchneri*), SMA (*buchneri*) |
| *Virgibacillus* spp. | YPD (*halophilus*) |
| *Paenibacillus* spp. | AMA (*chibensis*), NA (*cookii*), RMA, MRS |
| *Clostridium* spp. | SMA (*pasteurianum, beijerinckii*), RCM (*pasteurianum*) |
| *Oceanobacillus* spp. | RMA (*oncorhynchi-incaldanensis*) |
| *Acetobacter* spp. | YPD (*pasteurianus*), PA (*pasteurianus*) |
| *Pseudomonas* spp. | NA (*putida; fluorescens*) |
| *Streptomyces* spp. | YMEA (*griseus*) |

* NA: nutrient agar (BD #213000); SMA: standard method agar (BD #247940); YPD: yeast peptone dextrose (BD #242720); AMA: *azotobacter* medium agar (HIMEDIA #M372); AMAG: *azotobacter* medium agar supplement with 10 g/L glucose (HIMEDIA #M371); RCM: reinforce *clostridium* medium (BD#218081); RMA: *rhizobium* medium agar (HIMEDIA #M408); PA: Pikovskaya's medium (HIMEDIA #M520); MRS: *Lactobacilli* MRS (BD# 288210).

Isolation of Microbes from Soil Samples:

To 30-50 grams of soil, 1% w/w of mannitol or sucrose was added followed by 2 mL of sterile water for each 10 g of soil. In a sterile mortar, the resulting mud was kneaded to generate a homogenous paste. The paste was subsequently transferred to a Petri dish and incubated at 27-30° C. in a humidified chamber for up to 1 week. A sample of the slimy substance that formed on the surface of the soil paste was subsequently transferred to fresh and sterile semi-solid Nitrogen-free medium (see Example 3 for medium composition). The resulting microbial growth was rendered biologically pure through sub-culturing, as described below.

Preparation of Biologically Pure Microbial Isolates:

After incubation, plates were analyzed for microbial growth. Microbial strains were selected for further investigation based on traditional macroscopic and microscopic characteristics of the colonies growing on semi-solid media (*Bergey's Manual of Systematics of Archaea and Bacteria*; Ed., William B. Whitman). Criteria such as colony color, density, or morphology (e.g., form, elevation, and margin) were considered. In order to obtain well separated colonies on solid medium, the technique of "streaking out" was used. Briefly, the selected microbial clones were struck on fresh new solid medium and allowed to grow until well differentiated colonies appeared. If needed, multiple subcultures were performed until a biologically pure microbial clone was obtained; these were termed "isolate." Additional tests were then performed on the isolate to study the bacteria cell morphology. Differential Gram staining was also used to begin classification of the isolate into the appropriate most probable genus.

Microbial Genomic DNA Extraction:

Bacterial cells of different species were grown and harvested from optimized liquid broth and culture conditions. PowerSoil DNA isolation kit (MoBio, Cat#12888) is used for small scale genomic DNA preparation. For large scale genomic DNA extractions, cell lysate was prepared using GenElute Bacterial Genomic DNA kit (Sigma, Cat # NA2110) or Qiagen Genomic DNA Buffer Set and Genomic-tip 500/G (Qiagen, Cat #19060 and 10262) following the methods recommended by manufacturer. The genomic DNA was then precipitated with equal volume of isopropanol, washed with 70% ethanol, air-dried and resuspended in TE buffer.

Amplification and Sequencing of 16S for Taxonomy Confirmation:

Full length 16S genes were amplified from different bacterial species using genomic DNA and/or colonies as the PCR template directly. Forward primer (27F, 5'-AGRGTTT-GATCMTGGCTCAG-3'; SEQ ID NO: 1) and Reverse primer (1492R, 5'-GGTTACCTTGTTACGACTT-3'; SEQ ID NO: 2) were designed following Singer et al. (2016) with minor modifications. PCR products were sequenced directly using the forward and reverse PCR primers. The high-quality sequence traces were BLAST searched against NCBI Nucleotide Collection (nr/nt) Database for taxonomy confirmation. Full length 16S rDNA sequences obtained are provided herein as SEQ ID NOs: 3-24.

Whole Genome Sequencing (WGS):

Whole Genome Sequencing of biologically pure isolates was performed using PacBio RSII system (Pacific Biosciences Menlo Park, Calif. USA) following the manufacturer's recommended method for sequence library preparation and sequencing. An average of 73,000 reads of 24 kb in length on average were generated from the microbial isolates. De novo genome assembly was performed with Hierarchical Genome Assembly Process (HGAP, Pacific Biosciences, Menlo Park, Calif. USA).

Whole-Genome Alignment:

The number of named bacterial species with completely sequenced genomes has rapidly grown in the past few years, yet remains small compared to the number of 16S rRNA sequences. When a reference genome is available, however, performing a whole-genome alignment is one of the most definitive ways to confirm a species, or even strain level match. To that end, high-quality microbial genomes were downloaded from RefSeq and aligned against isolate whole genome sequences using MUMmer (Delcher et al., *Nucl. Acids Res.* 30:2478-2483, 2002; Kurtz et al., *Genome Biol.* 5:R12, 2004), which identifies Maximal Unique Matches ("MUM"s) between very long sequences.

Identification and Classification of 16S rRNA Genes and Conserved Phylogenetic Marker Genes (pMGs):

Ribosomal RNA (rRNA) genes were identified within the de novo genome assembly using the Barrnap program (Seemann, 2014), which is a wrapper for the NHMMer tool (Wheeler and Eddy, 2013) included with HMMer 3.1. The 16S rRNA sequences were then classified using the Ribosome Database Project (RDP) Naïve Bayesian Classifier, as well as pairwise alignment with BLASTn (Camacho et al., *BMC Bioinformatics* 10:421, 2009; Cole et al., *Nucleic Acids Research* 42(D1):633-642, 2014).

As the number of organisms with sequenced genomes has grown, it has become increasingly common to leverage this data for more specific taxonomic classification. The specI database contains sequences for 40 conserved phylogenetic marker genes (pMGs) that were selected from the COG (Conserved Orthologous Groups) database (Tatsuov et al., *Science* 278:631-637, 1997). Most of them are related to genetic information processing. There are sequences for several thousand species of bacteria within the specI database (Mende et al., *Nature Methods* 10:881-884, 2013). Therefore, protein coding genes were identified within the genomic sequence each microbial isolate assembled using Prodigal (v2.6.2) (Hyatt et al., *BMC Bioinformatics* 11:119, 2010), which leverages heuristic thresholds developed in coordination with genome curation experts at the US Department of Energy Joint Genome Institute (JGI). The translated coding sequences identified by Prodigal were annotated by the FetchMGs program included with specI (v1.0), which uses a set of empirically-determined cutoffs for identifying sequences belonging to each pMG COG within a given proteome. The coding genes whose translated sequences were identified by FetchMGs as belonging to one of the 40 specI pMGs were then aligned against the untranslated reference pMGs from the specI database using BLASTn.

Taxonomic Classification of Microbial Isolates:

Traditionally, identifying microorganisms at the species level is often decided on the basis of a single universal marker gene, the 16S rRNA gene (see, e.g., Stackebrandt et al., *Int. J. Syst. Bacteriol.* 44:846-849, 1994; Janda et al., *J. Clin. Microbiol.* 45:2761-2764, 2007). However, the microbiology community has noticed that the identity of microbes for which whole-genome information has become available does not always correlate with the identity determined by the approaches commonly used prior to the advent of next-generation high-throughput sequencing. Moreover, whole genome information is not available for every microbe and a large number of databases that capture the microbial genetic landscape are not validated/curated. Therefore, assigning a species/strain to new microbial isolates is a challenge.

Taking into account the taxonomic identification limitations described above, the approach taken for species assignment of each microbe isolate described herein was a multipronged approach. Genetic information such as whole genome sequencing, analysis of 40 conserved phylogenetic marker genes, and 16S rRNA gene analysis was generated for each isolate. Two third party laboratories offering taxonomic identification services were independently contracted to provide genus and species identification based on their proprietary databases and algorithms. In addition, sequence homology searches of the full length 16S rRNA gene for each microbe was performed in three independent databases: Greengenes database (DeSantis et al., *Appl. Environ. Microbiol.* 72:5069-5072, 2006), EZTaxon database (Kim et al., *Int. J. Syst. Evol. Microbiol.* 62:716-721, 2012), and the National Center for Biotechnology information database (U.S. National Library of Medicine, Bethesda, Md.).

A species was assigned to each isolate if at least three or more database searches (including third party proprietary databases and public databases as listed above) and identification services returned identical species assignment. For at least three isolates, the databases searches did not return identical species assignments in at least three databases. In those cases, an assignment was made on best judgment (*Bacillus* sp., *Pseudomonas* sp., and *Paenibacillus lautus*).

Based on the above, microbial identifications were made as follows:

*Lactobacillus delbrueckii*. The results of all analyses strongly supported the identification of this isolate as *Lactobacillus delbrueckii* subsp. *bulgaricus* ND02.

*Virgibacillus halophilus*. The 16S BLASTn results suggested that this isolate might be a strain of *Virgibacillus halophilus*, although this could not be confirmed by any other methods due to a lack of suitable reference sequences. The 16S BLASTn results were consistent with the genus-level assignment from the naïve Bayesian classifier (NBC), but were insufficient to confirm a species-level classification on their own.

*Azotobacter vinelandi.* This isolate appears to be a novel strain of *Azotobacter vinelandii.* This was supported by analysis of 16S rRNA and other phylogenetic marker genes, as well as whole-genome alignments to both of the two closest candidate strains. The large number of both small and large differences observed in the whole genome alignment, as well as the numerous small differences between the 16S and coding sequences, suggest that this may be a novel strain, and potentially even a novel species, although this isolate was clearly more closely related to *Azotobacter vinelandii* than to any other species contained in any of the databases.

*Clostridium pasteurianum.* The 16S analyses and whole-genome alignments supported the identification of this isolate as a novel strain of *Clostridium pasteurianum.* The specI database does not contain any reference sequences for *C. pasteurianum,* although the specI results do provide further support down to the genus level.

*Paenibacillus chibensis.* The strongest evidence for the positive identification of this isolate was the genus-level classification from the RDP NBC, which assigned this isolated to *Paenibacillus* with a probability of 1.0. Both the 16S and specI BLASTn results supported this assignment. A closely matching reference genome could not be found in RefSeq, although persistent syntemy was observed between the genome assembly and a reference sequence for *Paenibacillus* sp. Y412MC10. Full length 16S rRNA gene sequence alignment in available databases currently suggests that this isolate belongs to *Paenibacillus chibensis.*

*Streptomyces griseus.* This isolate was clearly a strain of *Streptomyces griseus* that is extremely closely related to NBRC 13350. This was supported by analysis of 16S rRNA and other phylogenetic marker genes, as well as whole-genome alignments to both of the two closest candidate strains. The whole-genome alignment did reveal a number of differences scattered across the genome, however, suggesting that this isolate should be classified as a separate strain.

*Pseudomonas* sp. It is clear that this isolate belongs in the genus *Pseudomonas* and that it is very closely related to *Pseudomonas entomophila,* but it is not an exact match to strain L48, the only *Pseudomonas entomophila* strain with an available reference genome. This isolate is also closely related to *P. putida,* and *P. fluorescens.*

*Pseudomonas putida.* The results of some analyses supported the identification of this isolate as *Pseudomonas putida.* While this isolate appears to be extremely closely related to strain *P. putida* NBRC 14164, the best available reference, the whole-genome analyses revealed numerous small differences across the entire genome, suggesting that this isolate should be classified as a separate strain.

*Oceanobacillus oncorhynchi.* The 16S analyses and whole-genome alignments supported the identification of this isolate as a novel strain *Oceanobacillus oncorhynchi.* The specI database does not contain any reference sequences for *O. oncorhynchi,* although the specI results do provide further support down to the genus level.

*Paenibacillus lautus.* The results of all analyses strongly supported the identification of this isolate as a strain of *Paenibacillus* that is closely related, though not identical, to the well characterized sp. Y412MC10. Considering the high density of small differences along the entire whole-genome alignment with sp. Y412MC10, the numerous small differences observed in the pair-wise alignments of the sp. Y412MC10 marker genes, and the observation of similarly good alignments to sequences from sp. HGF5, and the fact that *Paenibacillus* sp. Y412MC10 has yet to be formally named. Full length 16S rRNA gene sequence alignment in available databases currently suggests that this isolate belongs to species of *Paenibacillus lautus.*

*Bacillus licheniformis.* The results of all analyses strongly supported the identification of this isolate as *Bacillus licheniformis* DSM 13=ATCC 14580, possibly all the way down to the strain level. However, this isolate could be a unique strain based on the rather large rearrangement and other small differences revealed by the whole-genome alignment, as well as the point-mutations observed in the 16S and specI results, but it is rare to observe such a high degree of sequence identity between two genomes, even from the same species.

*Lactobacillus vini.* Bergey's Manual of Systematic Bacteriology did not contain any further information about *Lactobacillus mobilis,* or the potentially contra specific and equally poorly characterized *Lactobacillus vini* (Passoth et al., *Microbiology* 73:4354-4356, 2007). Whole-genome alignments against the only available references for *L. vini* indicated a large number of homologous regions, but the extreme fragmentation of the reference sequences made it difficult to assess the relationship between any of them and this isolate. Full length 16S rRNA gene sequence alignment in available databases currently suggests that this isolate belongs to species of *Lactobacillus vini.*

*Paenibacillus cookii.* The strongest evidence for the positive identification of this isolate is the genus-level classification from the RDP NBC, which assigned this isolate to *Paenibacillus* with a probability of 1.0. Both the 16S and specI BLASTn results supported this assignment. A closely matching reference genome could not be found in RefSeq, although persistent syntemy was observed between the isolate assembly and a reference sequence for *Paenibacillus* sp. Y412MC10. Full length 16S rRNA gene sequence alignment in available databases currently suggests that this isolate belongs to species of *Paenibacillus cookii.*

*Lactobacillus buchneri.* The results of all analyses strongly supported the identification of this isolate as *Lactobacillus buchneri,* although the specI results did not support the 16S analyses and whole-genome alignments, presumably because the database lacked the necessary reference sequences. While this sample appears to be extremely closely related to strain *L. buchneri* CD034, the best available reference, the whole-genome analyses still revealed dozens of differences including two large deletions, suggesting that this isolate should be classified as a separate strain.

*Bacillus megaterium.* The results of all analyses strongly supported the identification of this isolate as *Bacillus megaterium.* While this isolate appears to be extremely closely related to strain *B. megaterium* DSM319, the best available reference, the whole genome analyses revealed many small differences across the entire genome, suggesting that this isolate should be classified as a separate strain.

*Acetobacter pasteurianus.* The results of all analyses strongly supported the identification of this isolate as *Acetobacter pasteurianus.* This isolate appears to be extremely closely related to the *A. pasteurianus* IFO 3283 strains, the best available references, but the whole-genome analyses revealed many small differences across the entire genome for even the closest match, suggesting that this isolate should be classified as a separate strain.

*Clostridium beijerinckii*. The results of all analyses strongly supported the identification of this isolate as *Clostridium beijerinckii*. While it appears to be extremely closely related to strain *C. beijerinckii* NCIMB 8052, the best available reference, the whole-genome analyses revealed many small differences across the entire genome, suggesting that this isolate should be classified as a separate strain.

*Lactobacillus casei/paracasei*. The results of all analyses strongly supported the identification of this isolate as *Lactobacillus casei* or *Lactobacillus paracasei*. The best matches from all analyses were consistently from members of these two overlapping species, yet all analyses revealed many small differences spanning the entire length of the genome, suggesting that this isolate should be classified as a separate strain.

*Bacillus flexus*. The strongest evidence for the positive identification of this isolate is the genus-level classification from the RDP NBC, which assigned it to *Bacillus* with a probability of 1.0. Both the 16S and specI BLASTn results, as well as the MUMmer whole-genome alignments, supported this assignment down to the genus level. Full length 16S rRNA gene sequence alignment in available databases currently suggests that this isolate belongs to species of *Bacillus flexus*.

*Bacillus* sp. The 16S analyses strongly supported the identification of this isolate as a strain of *Bacillus*, but none of the analyses were able to positively assign it to a named species. The 16S BLASTn results suggest that it might be a strain of *Bacillus kochii*, but the lack of whole-genome sequences in available databases prevented this from being confirmed.

*Bacillus subtilis*. The results of all analyses strongly support the identification of this isolate as *Bacillus subtilis*. The taxonomies and nomenclatures for this genus and species are quite complex, although the results of all analyses were overwhelmingly dominated by strains that had been formally classified as *B. subtilis*. Despite an abundance of sequence data and many exact matches to individual genes, an exact genome-wide match could not be identified, strongly indicating that this isolate is a novel strain of *B. subtilis*.

*Bacillus amyloliquefaciens*. The results of all analyses strongly support the identification as *Bacillus amyloliquefaciens* subsp. *plantarum*, although the taxonomy for this species is currently quite complex. *Bacillus amyloliquefaciens* subsp. *plantarum* has undergone very recent renaming to *Bacillus velezensis* (Dunlap et al., *Int. J. System. Evol. Microbiol.* 65:2104-2109, 2015; Dunlap et al., *Int. J. System. Evol. Microbiol.* 66:1212-1217, 2015). These changes have led to partial reclassification and reorganization in RefSeq, although the sequence identifiers in the specI and RDP databases still refer to *Bacillus amyloliquefaciens* subsp. *plantarum*.

Example 2

Individual Growth and Co-Culture of Microbes

Growth Medium Preparation:

Growth media tested were prepared using off the shelf salts and reagents. Liquid media were sterilized by autoclaving at 121° C., 15 psi for at least 30 minutes or by filtration through 0.45 µm filter membranes.

Study of Individual Strain Growth Dynamics in Mono-Cultures:

The growth rate of each biologically pure microbial isolate was analyzed. Up to 3 mL liquid cultures were prepared for each isolate starting from master plates. Each isolate was grown for 1-3 days at 30° C. to obtain cultures with sufficient density at log state. Each isolate was then subcultured into 24 well microtiter plates containing 1 mL of growth medium (see below) at an optical density ($OD_{600}$) of ~0.05. Using the Cytation 5 Imaging Reader (BioTek, Winooski, Vt. USA) the growth profile of each isolate was recorded in real time (every 30 seconds) over a period of 1 week under aerobic conditions at 30° C. Sterile medium was used as negative control.

Co-Culture of Microbes in Fermentation Experiments

Continuously Stirred Bioreactors:

Fermentations were done in 2 liter DASGIP bioreactors (Eppendorf North America Hauppauge, N.Y.) with a 1.5 liter working volume. The vessels were sterilized by autoclaving at 121° C., 15 psi for one hour. The growth medium was sterilized along with the vessels except for PBS which was sterilized separately and aseptically added to the bioreactor prior to inoculation. Polypropylene glycol 2000 was used as a foam control agent. It was aseptically added to the bioreactor prior to inoculation at a concentration of 0.07 v/v %. Vessels were inoculated directly from thawed working cell bank vials at an inoculum volume of 0.1-0.4 v/v %. Fermentation temperature was controlled at 30° C. Depending on the fermentation, dissolved oxygen concentration was sometimes controlled and sometimes not. When controlled, the dissolved oxygen set point was in the range of 1-25% of air saturation. Dissolved oxygen control was effected using a cascade of agitation, then air flow to maintain the set point. When dissolved oxygen control was not used, agitation was fixed at a value between 200 and 800 rpm and the air flow rate was fixed at a value between 0.1 and 0.5 vvm. Similarly, the pH of the fermentation broth was sometimes controlled and sometimes not. When controlled, the pH set point was in the range of 6.3 to 6.9. The pH titrants were 20 w/w % KOH and 13.8 w/w % $H_3PO_4$. The pH of the fermentation broth was checked daily with an off-line pH meter to correct for any drift in the bioreactor pH probe.

Spinner Flask Bioreactor:

The microbial inoculum was mixed with a suspension containing 5.5% w/w whey protein and 1.2% w/w yogurt in water ("C vat") and a suspension containing 0.1% w/w *spirulina* and 0.1% w/w kelp extract in water ("A vat"). The A vat and C vat suspensions were each individually prepared 3 days before mixing with the seed culture and incubated at ambient temperature. The seed culture, C vat, and A vat were mixed at a proportion of about 81:9:9. After mixing, a suspension of additional components containing about 70% v/v molasses, 0.5% v/v HYT B, 0.003% w/v Arabic gum, and 0.02% w/v brewer's yeast (*S. cerevisiae*) were mixed with the mixture of the seed culture, C vat, and A vat, and additional water at a ratio of about 16:34:50. The mixture was fermented for about 7 days at ambient temperature (about 19-35° C.). After 7 days, the flasks (1.7 L) were aerated for 30 minutes every other day. Additional water was added (about 10% more v/v) and fermentation was continued under the same conditions for about 10 more days. Additional water was added (about 4% more v/v) and fermentation was continued for about 7 more days, at which time samples were collected for analysis.

Microbial Population Analysis—Droplet Digital PCR:

Droplet Digital PCR (ddPCR) system provides detection and absolute quantification of the presence of a target organism (Dreo et al., *Anal. Bioanal. Chem.* 406:6513-6528, 2014; Yin, et al., Journal of Microbiological Methods 65:21-31, 2006). Specific primers for the 22 bacterial species identified in Example 1 were designed using unique sequences from the 16S genes and/or unique coding gene sequences identified from WGS genome assemblies (Tables 2 and 3). ddPCR was performed using either EvaGreen Supermix or Supermix For Probes (BioRAD, Hercules Calif. USA) per manufacturer's recommendation QX200 Droplet Digital PCR System (BioRAD, Hercules Calif. USA), and the ddPCR data was then analyzed in QuantaSoft (BioRAD, Hercules Calif. USA).

TABLE 2

Forward and reverse primers for ddPCR EvaGreen Supermix method

| Bacteria | Forward Primer | Reverse Primer |
|---|---|---|
| *Acetobacter pasteurianus* | CAAGTCGCACGAAGGTTTC (SEQ ID NO: 25) | CGGGGATTTCACATCTGACT (SEQ ID NO: 26) |
| *Azotobacter vinelandii* | GGGTCAAGAGCTTCACCTAC (SEQ ID NO: 27) | CGATGTCTGCCAGGGAATG (SEQ ID NO: 28) |
| *Bacillus amyloliquefaciens* | TGCGCTTATGAATGGAGGAG (SEQ ID NO: 29) | CTTTATCAGGCCTGGTACCG (SEQ ID NO: 30) |
| *Bacillus flexus* | TCTCTTGCATAAGAGAAAATTGAAA (SEQ ID NO: 31) | CTACGCATTTCACCGCTACA (SEQ ID NO: 32) |
| *Bacillus licheniformis* | GGAGCTTGCTCCCTTAGGTC (SEQ ID NO: 33) | CTCAAGTTCCCCAGTTTCCA (SEQ ID NO: 34) |
| *Bacillus megaterium* | CCGGATAGGATCTTCTCCTTC (SEQ ID NO: 35) | CTACGCATTTCACCGCTACA (SEQ ID NO: 36) |
| *Bacillus sp.* | TTTATACATATAATTAGATTGAAAGATGG (SEQ ID NO: 37) | CTACGCATTTCACCGCTACA (SEQ ID NO: 38) |
| *Bacillus subtilis* | GATCTTTCTTGGGGATGGG (SEQ ID NO: 39) | CCGAACCCAACAGTCCAATA (SEQ ID NO: 40) |
| *Clostridium beijerinckii* | GATGAAGCTCCTTCGGGAGT (SEQ ID NO: 41) | AATGCAGCACCCAGGTTAAG (SEQ ID NO: 42) |
| *Clostridium pasteurianum* | CAAGTCGAGCGAGAAACCTT (SEQ ID NO 43) | GAAATGCAGTCCCCAGGTTA (SEQ ID NO: 44) |
| *Lactobacillus buchneri* | GGTGCTTGCACTTGAAAGATT (SEQ ID NO: 45) | CTCGCTTTACGCCCAATAAA (SEQ ID NO: 46) |
| *Lactobacillus delbrueckii* | CGAGCGAGCTGAATTCAAAG (SEQ ID NO 47) | CTCGCTTTACGCCCAATAAA (SEQ ID NO: 48) |
| *Lactobacillus paracasei (casei)* | CTCGTTGATGATCGGTGCT (SEQ ID NO: 49) | TAAATCCGGATAACGCTTGC (SEQ ID NO: 50) |
| *Lactobacillus vini* | ACCGCCTGGTTTTGATGTTA (SEQ ID NO 51) | CATTTCACCGCTACACATGG (SEQ ID NO: 52) |
| *Oceanobacillus oncorhynchi* | GGAACTCTTCGGAGGGAAGT (SEQ ID NO: 53) | CAGTTTCCAATGCACGTTTG (SEQ ID NO: 54) |
| *Paenibacillus lantus* | TGCAGCATTGTGAAATAATGAA (SEQ ID NO: 55) | CTACGCATTTCACCGCTACA (SEQ ID NO: 56) |
| *Paenibacillus chibensis* | CCGGATAATTTATTTTCTCTCCTG (SEQ ID NO: 57) | CTACGCATTTCACCGCTACA (SEQ ID NO: 58) |
| *Paenibacillus cookii* | ATTTATCGCTTCGCATGGAG (SEQ ID NO 59) | CTACGCATTTCACCGCTACA (SEQ ID NO: 60) |
| *Pseudomonas sp.* | CGGGAGCTTGCTCCTTGA (SEQ ID NO: 61) | CTCTAGCTCGCCAGTTTTGG (SEQ ID NO: 62) |
| *Pseudomonas putida* | AAGTCGAGCGGATGAGAAGA (SEQ ID NO: 63) | CGCTTTACGCCCAGTAATTC (SEQ ID NO: 64) |

TABLE 2-continued

Forward and reverse primers
for ddPCR EvaGreen Supermix method

| Bacteria | Forward Primer | Reverse Primer |
| --- | --- | --- |
| Streptomyces griseus | GTCGAACGATGAAGCCTTTC (SEQ ID NO: 65) | AGGAATTCCGATCTCCCCTA (SEQ ID NO: 66) |
| Universal prokaryote primers | GTGCCAGCAGCCGCGGTAA (SEQ ID NO: 67) | TGGACTACCAGGGTATCTAATCCTGTT (SEQ ID NO: 68) |
| Virgibacillus halophilus | CCTCATCTGAGGTGATTCCTG (SEQ ID NO: 69) | TCCTCCAGTTTCCAATGACC (SEQ ID NO: 70) |

TABLE 3

Oligonucleotides for ddPCR Supermix for Probes method

| Species Name | Forward Primer | IN Probe | Reverse Primer |
| --- | --- | --- | --- |
| Bacillus megaterium | TCGAGCGAAACAGAAGTGAA (SEQ ID NO: 71) | TCTGTGATGAATGTGATGCGGA (SEQ ID NO: 72) | GCTGAACTTTCACACGATGC (SEQ ID NO: 73) |
| Lactobacillus paracasei (casei) | ACGCAGGCGATTTATCATCA (SEQ ID NO: 74) | TTTGCTTTCCGGTGGCTCAT (SEQ ID NO: 75) | AGCCCATATCAACCAGCATC (SEQ ID NO: 76) |
| Clostridium beijerinckii | GCTGAAGGAGGGACACTTTT (SEQ ID NO: 77) | AGAGTTTGAACGTGTTGGTGGT (SEQ ID NO: 78) | TCAGATCACGGTTTGTTGCT (SEQ ID NO: 79) |
| Acetobacter pasteurianus | AACGGTTAACAATCAGCCCA (SEQ ID NO: 80) | TCTTACCGGAAAAGAATTCGCCA (SEQ ID NO: 81) | CGCAAGACAAGCAGTTCAAG (SEQ ID NO: 82) |
| Lactobacillus buchneri | CAACCAACTGGATCAAGGGA (SEQ ID NO: 83) | ACCTGCTGAAGCAGCGATTT (SEQ ID NO: 84) | AATCATACCGATCAGTGCCG (SEQ ID NO: 85) |
| Bacillus subtilis | TGCTGAACGGAAAACATCCT (SEQ ID NO: 86) | AAAATCGGTGCGGAAGGTCC (SEQ ID NO: 87) | TGCAACTACACTTACCGCAA (SEQ ID NO: 88) |
| Bacillus amyloliquefaciens | TGCGCTTATGAATGGAGGAG (SEQ ID NO: 89) | AAAAGGGCCGATCACATGGG (SEQ ID NO: 90) | CTGTAATCCGGTCCGTACAC (SEQ ID NO: 91) |
| Paenibacillus cookii | ATATCCTGCGCTGGTACAAC (SEQ ID NO: 92) | CGGCAGACTTGAAGCTCGAG (SEQ ID NO: 93) | TCTTGTACATGGAAGCCGTG (SEQ ID NO: 94) |
| Lactobacillus vini | CGACTAACCTGATCGCACTT (SEQ ID NO: 95) | TGAAGCTCAGATTTCACGGCT (SEQ ID NO: 96) | ATTACGCCGATTCCTTCTGG (SEQ ID NO: 97) |
| Paenibacillus chibensis | TGACATTCCATTCATCCGGG (SEQ ID NO: 98) | AAATGGCGGAGATCACGTATCA (SEQ ID NO: 99) | ATCCCAGCCAAATTTCCACA (SEQ ID NO: 100) |
| Bacillus licheniformis | GCAAAACAAACAGGCTCCAA (SEQ ID NO: 101) | AAATCAGCCTCTGGCTTGCC (SEQ ID NO: 102) | CTGACCGGGATAGTTGGTTC (SEQ ID NO: 103) |
| Paenibacillus lantus | CTGGATATCCCGCATTTGGT (SEQ ID NO: 104) | CTGTATGCCGCTTTGACGGA (SEQ ID NO: 105) | GCGAGGAATCATGTAGCCTT (SEQ ID NO: 106) |
| Oceanobacillus oncorhynchi | AGGTTCCGATGTAGTGCTTG (SEQ ID NO: 107) | ACATACAACGCACACCGAGAA (SEQ ID NO: 108) | ATTTCCTGCAACCAGAGCTT (SEQ ID NO: 109) |
| Bacillus sp. | TCCGAAGCTGCTGAAATCTT (SEQ ID NO: 110) | ACCTGACCGTGGTGGAGAAA (SEQ ID NO: 111) | TTGAAAGTAAATCGCGCGTC (SEQ ID NO: 112) |

TABLE 3-continued

Oligonucleotides for ddPCR Supermix for Probes method

| Species Name | Forward Primer | IN Probe | Reverse Primer |
|---|---|---|---|
| Pseudomonas putida | AATCATCACAGATGCG GAGG (SEQ ID NO: 113) | ATTGTGCCATCCGGCT ATGG (SEQ ID NO: 114) | GTGCCGAGATGAAGAA GTGA (SEQ ID NO: 115) |
| Pseudomonas sp. | GCTGACCTATGTGAAG TCCC (SEQ ID NO: 116) | AGATCGATGGCGTGTT GGTG (SEQ ID NO: 117) | TGATAAAGATGGACGC CGAC (SEQ ID NO: 118) |
| Streptomyces griseus | CTGGGACTACATGAAG CAGG (SEQ ID NO: 119) | TGGACGCCGAGATCCT CTAC (SEQ ID NO: 120) | TAGGTCTTCTGGAGCG ACTT (SEQ ID NO: 121) |
| Bacillus flexus | TGGGCTTGGTGTATGT GTTT (SEQ ID NO: 122) | ATGGCACAAAGCTACG GCTT (SEQ ID NO: 123) | GAACCATGAGCCCGTA ATGA (SEQ ID NO: 124) |
| Clostridium pasteurianum | GGATGTACAGAAAATT GCAGC (SEQ ID NO: 125) | AGCTTATTGGAGAGGT TACAACTGT (SEQ ID NO: 126) | AGGAGTTGATATCAGG TATGGT (SEQ ID NO: 127) |
| Azotobacter vinelandii | GCATATTGCCTTTGGT GTGG (SEQ ID NO: 128) | CCCCATGGGGGTAACC ATTG (SEQ ID NO: 129) | TCCATCCTGGGGTTGT TTTC (SEQ ID NO: 130) |
| Virgibacillus halophilus | GCTATATGGGCTCCAA AGCA (SEQ ID NO: 131) | AAAAGCCGATGTAGTA CTCGCT (SEQ ID NO: 132) | TTCCGAAAACAGACAG CCTT (SEQ ID NO: 133) |
| Lactobacillus delbrueckii | ACCAGTGAAGAACTG GAAGC (SEQ ID NO: 134) | ACGCGAAGACAAGA TCTGCC (SEQ ID NO: 135) | TCACCGTTCAAAGTCC AGTC (SEQ ID NO: 136) |

Medium Development for Mono-Cultures:

Each of the microbes were isolated on various media. We analyzed whether one medium formulation was sufficient for the growth of all 22 isolates.

The growth of all 22 isolates was first tested on Molasses alone. We found that 5 of the 22 strains demonstrated detectable growth. The formulation of the medium was then optimized to include essential elements such as phosphates, sodium, potassium and chloride (in the form of commercially available Phosphate Buffer Saline). This resulted in the growth of an additional 6 isolates. Sources of amino acids, nitrogen and peptides/proteins in the form of food grade Whey powder and non-GMO soybean extract produced enzymatically (Ferti-Nitro Plus Plant N; Ferti-Organic, Brownsville, Tex. USA) were then added. Whey alone did not significantly improve the growth performance of most isolates, except for *Bacillus* sp. Ferti-Nitro Plus Plant N alone appeared to stimulate the growth of a large number of microbes. Together whey protein and Ferti-Nitro Plus Plant N seemed to have a modest synergistic effect, further stimulating growth of *A. pasteurianus, O. oncorhynchi, C. pasteurianum, L. delbrueckii* and *V. halophilus*. The results are summarized in Table 4.

TABLE 4

Growth performance evaluation of individual microbes in PBS/molasses medium

| | | | | | |
|---|---|---|---|---|---|
| Black strap Molasses (in water) (% w/v) | 2 | 2 | 2 | 2 | 2 |
| 1x PBS | − | + | + | + | + |
| Whey proteins (% w/v) | − | − | 0.1 | − | 0.1 |
| Ferti-Nitro Plus (% w/v) | − | − | − | 0.25 | 0.25 |

TABLE 4-continued

Growth performance evaluation of individual microbes in PBS/molasses medium

| Microorganisms | Growth performance | | | | |
|---|---|---|---|---|---|
| Bacillus megaterium | (−) | (+++) | (+++) | (+++) | (+++) |
| Lactobacillus casei/paracasei* | (−) | (−) | (−) | (+++) | (+++) |
| Clostridium beijerinckii* | (−) | (−) | (−) | (+++) | (+++) |
| Acetobacter pasteurianus | (−) | (+) | (+) | (+) | (++) |
| Lactobacillus buchneri* | (−) | (−) | (−) | (+++) | (+++) |
| Bacillus subtilis | (+++) | (+++) | (+++) | (+++) | (+++) |
| Paenibacillus cookii | (−) | (+) | (+) | (+++) | (+++) |
| Lactobacillus vini* | (−) | (−) | (−) | (++) | (++) |
| Bacillus licheniformis | (++) | (++) | (+++) | (+++) | (+++) |
| Paenibacillus lautus | (−) | (−) | (−) | (++) | (++) |
| Oceanobacillus oncorhynchi | (−) | (−) | (−) | (−) | (+) |
| Bacillus amyloliquefaciens | (+) | (++) | (+++) | (+++) | (+++) |
| Bacillus sp. | (−) | (−) | (+) | (+++) | (+++) |
| Pseudomonas putida | (+) | (+) | (+) | (+++) | (+++) |
| Pseudomonas sp. | (−) | (−) | (−) | (+++) | (+++) |
| Streptomyces griseus | (−) | (+++) | (+++) | (+++) | (+++) |
| Paenibacillus chibensis | (−) | (+) | (+) | (+++) | (+++) |
| Bacillus flexus | (+) | (++) | (+++) | (+++) | (+++) |
| Clostridium pasteurianum* | (++) | (−) | (−) | (−) | (++) |
| Virgibacillus halophilus | (−) | (+) | (+) | (+) | (++) |
| Azotobacter vinelandii | (−) | (+++) | (+++) | (+++) | (+++) |
| Lactobacillus delbrueckii* | (−) | (−) | (−) | (−) | (+) |

(−): no growth detected; (+): low growth; (++): moderate growth; (+++): robust growth.
*Isolates grown under anaerobic conditions.

In other experiments, a medium that would support growth of two isolates—*C. pasteurianum* and *Azotobacter vinelandii*—was explored. In addition, it was intended to develop a medium that would improve the growth of some isolates such as *O. oncorhynchi* and *V. halophilus, L. delbrueckii* and *L. vini*, which did not show robust growth in the medium detailed above.

Using information on optimal growth conditions for each isolate (*Bergey's Manual of Systematics of Archaea and Bacteria*; Ed., William B. Whitman), the data above, publically available information on the elemental composition of bacteria (Rittmann and McCarty; *Environmental Biotechnology: Principles and Applications*; 2001 ISBN 0072345535), and a recommended growth medium for *Azotobacter* (1713 Modified *Azotobacter* Medium I; ATCC), various medium formulations were tested for growth of the 22 microbial isolates in mono-cultures. The results are summarized in Table 5.

In these experiments, potassium phosphate was tested as a source of elemental phosphorous and potassium together with various concentration of sodium chloride (to meet the requirement for halophilic microbes such as *O. oncorhynchi* and *V. halophilus*) as well as the requirement for whey and Ferti-Nitro plus Plant N as source of (but not limited to) amino acids and nitrogen. In addition to molasses, trace elements were supplemented in a designed mix of salts as described below.

In these experiments, *Azotobacter vinelandii* and *C. pasteurianum* performed well. Many other isolates also successfully grew, however, unlike the previous formulation (e.g., PBS/Molasses) not all of the strains grew consistently in one medium.

In other experiments growth of individual microbe isolates were evaluated in a medium that included yeast powder (0.021 g/L; YP), Arabic gum (0.028 g/L; AG), black strap molasses, whey powder (1.56 g/L; WP), *spirulina* (0.029 g/L, SP), kelp extract (0.029 g/L; KE), and 0.8% w/v NaCl (as there is evidence that isolates such as *O. oncorhynchi* and *V. halophilus* grow better in the presence of this salt). This medium is referred to as "Extract" medium herein. Microbial composition was monitored over time using ddPCR, as described above. Detected microbes were scored as (+). Microbes that were below the detection limit (BDL) of the ddPCR method were scored as such. The result of this experiment is summarized in Table 6.

TABLE 5

Growth performance evaluation of individual microbes in AAM01/molasses medium

| AAM01** | + | + | + | + | + | + | + | + |
|---|---|---|---|---|---|---|---|---|
| NaCl (g/L) | 5 | 5 | 5 | 5 | 10 | 10 | 10 | 10 |
| Molasses (% w/v) | 2 | 2 | 2 | 2 | 2 | 2 | 2 | 2 |
| K$_2$HPO$_4$ (g/L) | 1 | 1 | 1 | 1 | 1 | 1 | 1 | 1 |
| Ferti-Nitro Plus (% w/v) | 0.25 | 0.25 | 0.5 | 0.25 | 0.25 | 0.25 | 0.5 | 0.5 |
| Whey (% w/v) | 0 | 0.1 | 0 | 0.1 | 0 | 0.1 | 0 | 0.1 |

| Microorganisms | Growth performance | | | | | | | |
|---|---|---|---|---|---|---|---|---|
| *Bacillus megaterium* | (+++) | (+++) | (+++) | (+++) | (+++) | (+++) | (+++) | (+++) |
| *Lactobacillus. casei/paracasei** | (+++) | (+++) | (+++) | (+++) | (+++) | (+++) | (+++) | (+++) |
| *Clostridium beijerinckii** | (+++) | (+++) | (+++) | (+++) | (+++) | (+++) | (+++) | (++) |
| *Acetobacter pasteurianus* | (+) | (+) | (+) | (+) | (+) | (+) | (+) | (+++) |
| *Lactobacillus buchneri** | (++) | (++) | (++) | (++) | (++) | (++) | (++) | (+) |
| *Bacillus subtilis* | (+++) | (+++) | (+++) | (+++) | (+++) | (+++) | (+++) | (++) |
| *Paenibacillus cookii* | (+++) | (+++) | (+++) | (+++) | (+++) | (+++) | (+++) | (+++) |
| *Lactobacillus vini** | (++) | (++) | (++) | (++) | (++) | (++) | (++) | (+++) |
| *Bacillus licheniformis* | (+++) | (+++) | (+++) | (+++) | (+++) | (+++) | (+++) | (++) |
| *Paenibacillus lautus* | (+++) | (+++) | (+++) | (+++) | (+++) | (+++) | (+++) | (+++) |
| *Oceanobacillus oncorhynchi* | (−) | (+) | (−) | (−) | (−) | (−) | (−) | (+++) |
| *Bacillus amyloliquefaciens* | (+++) | (+++) | (+++) | (+++) | (+++) | (+++) | (+++) | (−) |
| *Bacillus* sp. | (+++) | (+++) | (+++) | (+++) | (+++) | (+++) | (+++) | (+++) |
| *Pseudomonas putida* | (+++) | (+++) | (+++) | (+++) | (+++) | (+++) | (+++) | (+++) |
| *Pseudomonas* sp. | (+++) | (+++) | (+++) | (+++) | (+++) | (+++) | (+++) | (+++) |
| *Streptomyces griseus* | (+++) | (+++) | (+++) | (+++) | (+++) | (+++) | (+++) | (+++) |
| *Paenibacillus chibensis* | (+++) | (+++) | (+++) | (+++) | (+++) | (+++) | (+++) | (+++) |
| *Bacillus flexus* | (+++) | (+++) | (+++) | (+++) | (+++) | (+++) | (+++) | (+++) |
| *Clostridium pasteurianum** | (++) | (++) | (++) | (++) | (++) | (++) | (++) | (+++) |
| *Virgibacillus halophilus* | (−) | (−) | (−) | (+) | (−) | (−) | (−) | (++) |
| *Azotobacter vinelandii* | (+++) | (+++) | (+++) | (+++) | (+++) | (+++) | (+++) | (−) |
| *Lactobacillus delbrueckii** | (+++) | (+++) | (+++) | (+++) | (+++) | (+++) | (+++) | (+++) |

**AAM01(Agrinos *Azotobacter* medium 01) is comprised of Ferrous sulfate (0.12 g/L); Magnesium sulfate (0.3 g/L); Calcium chloride (0.1 g/L); Manganese chloride (0.001 g/L), Sodium molybdate (0.001 g/L); Citric acid potassium sulfate (0.12 g/L).
*Isolates grown under anaerobic conditions.
(−): no growth detected;
(+): low growth;
(++): moderate growth;
(+++): robust growth

TABLE 6

Growth performance evaluation of individual microbes in Extract medium

| YP, AG, WP, SP, KE | + | + | + | + | + | + |
|---|---|---|---|---|---|---|
| Molasses | 14% w/v | 14% w/v | 10% w/v | 10% w/v | 2% w/v | 10% w/v |
| NaCl (w/v) | 0.8% | 0.8% | – | – | – | – |
| Ferti Nitro Plus (w/v) | – | 1.25% | – | 1.25% | 0.25% | – |
| 1× PBS | – | – | + | + | + | – |
| Microorganism | | | | | | |
| Bacillus megaterium | (+++) | (+++) | (+) | (–) | (++++) | (++) |
| Lactobacillus casei/paracasei* | (–) | (++) | (–) | (–) | (+) | (–) |
| Clostridium beijerinckii* | (–) | (+) | (–) | (–) | (+++) | (–) |
| Acetobacter pasteurianus | (++) | (+++) | (++) | (++) | (++) | (+++) |
| Lactobacillus buchneri* | (–) | (+) | (–) | (–) | (±) | (±) |
| Bacillus subtilis | (+++) | (–) | (++) | (++) | (++++) | (++) |
| Paenibacillus cookii | (–) | (–) | (++) | (+) | (++) | (–) |
| Lactobacillus vini* | (–) | (++) | (–) | (+) | (+) | (+) |
| Bacillus licheniformis | (+++) | (+) | (++) | (+) | (++++) | (++) |
| Paenibacillus lautus | (–) | (–) | (+++) | (++) | (+) | (+++) |
| Oceanobacillus oncorhynchi | (++) | (–) | (++) | (++) | (+) | (++) |
| Bacillus sp. | (–) | (–) | (++) | (++) | (++++) | (+++) |
| Pseudomonas putida | (+) | (–) | (++) | (++) | (+++) | (++) |
| Pseudomonas sp. | (–) | (–) | (++) | (++) | (+++) | (++) |
| Streptomyces griseus | (–) | (–) | (++) | (+++) | (+++) | (+) |
| Paenibacillus chibensis | (+) | (–) | (+++) | (+) | (+++) | (++) |
| Bacillus flexus | (+++) | (+) | (++) | (++) | (++++) | (++) |
| Clostridium pasteurianum* | (++) | (++) | (+) | (++) | (+++) | (+) |
| Azotobacter vinelandii | (–) | (+) | (+++) | (+) | (+++) | (++) |
| Virgibacillus halophilus | (–) | (–) | (++) | (++) | (+) | (+) |
| Lactobacillus delbrueckii* | (–) | (–) | (–) | (–) | (±) | (±) |
| Bacillus amyloliquefaciens | (+++) | (+++) | (++) | (–) | (+++) | (+) |

*Grown under anaerobic conditions

The fermentation performance in small scale bioreactors was investigated with two media formulations. The first medium consisted of Molasses, PBS, whey protein and Ferti-Nitro Plus Plant N (Table 4). Unlike media based on chemicals used in lab scale fermentation of Azotobacter (such as AAM01), no salt with potential safety concerns are present. Many research grade formulations of optimal media for growth of microorganisms recommend the use of trace metals such as Selenium and molybdenum (which is a potent enzyme cofactor, especially for nitrogenases). The Extract medium (Table 6) consisting of molasses and other natural extracts is highly similar to media currently in use.

Co-Culture in Small Scale Fermentation Experiments:

In order to evaluate fermentation conditions that would support the co-culture of all 22 microbial strains, bench scale fermenters were used. The resulting fermentation product was analyzed for the presence and abundance of each microbe, 4-28 days after inoculation. Two types of fermentation bioreactor configurations were used.

Continuous Stirred-Tank Reactor:

The first bioreactor configuration was a continuous stirred-tank reactor (CSTR). Two liter DASGIP bioreactors containing 1.5 L of medium were inoculated with 22 ODs of microbes (1 OD for each individual strain). The medium used in these experiments was based on results from Table 3 and contained the following ingredients phosphate buffer saline (1×), Black strap molasses (2-10% w/v), whey proteins (0.1-0.5% w/v), Ferti-Nitro Plus Plant N (0.25-1.25% w/v), with or without kelp extract (0.0067%), yeast powder (0.0033% w/v), and spirulina (0.0067% w/v). In these experiments, the gas composition (5% to 21% O2; 95 to 79% N2), gas flow rate (5 to 45 standard liters/hr), pH (6.3 to 6.7), agitation (200-1100 rpm), and dissolved oxygen (no control to 25%) was varied. Temperature remained constant at 30° C. The quantification and analysis of the microbial composition at the end of the fermentation runs was determined using ddPCR with strain specific probes, as described above. Detected microbes were scored as (+). Microbes that were below the detection limit (BDL) of the ddPCR method were scored as such examples of results are illustrated in Table 7.

TABLE 7

Summary microbial profile in co-culture fermentation using 1.5 L CSTR.

| | Medium permutations | | |
|---|---|---|---|
| Microbe | 10% Molasses | 2% Molasses | Kelp Extract Yeast Powder Spirulina w/10% molasses |
| Bacillus megaterium | (+) | (+) | (+) |
| Lactobacillus. casei/paracasei | (+) | (+) | (+) |
| Clostridium beijerinckii | BDL* | (+) | BDL |
| Acetobacter pasteurianus | (+) | (+) | (+) |
| Lactobacillus buchneri | (+) | (+) | (+) |
| Bacillus subtilis | (+) | (+) | (+) |
| Paenibacillus cookie | (+) | (+) | (+) |
| Lactobacillus vini | (+) | (+) | (+) |
| Bacillus licheniformis | (+) | (+) | (+) |
| Paenibacillus lautus | (+) | (+) | (+) |
| Oceanobacillus oncorhynchi | (+) | BDL | BDL |
| Bacillus sp. | (+) | (+) | (+) |
| Pseudomonas putida | (+) | (+) | (+) |
| Pseudomonas sp. | (+) | (+) | (+) |
| Streptomyces griseus | BDL | (+) | (+) |
| Paenibacillus chibensis | (+) | (+) | (+) |
| Bacillus flexus | BDL | BDL | (+) |
| Clostridium pasteurianum | (+) | (+) | (+) |
| Azotobacter vinelandii | (+) | (+) | (+) |
| Virgibacillus halophilus | (+) | BDL | BDL |
| Lactobacillus delbrueckii | (+) | (+) | (+) |
| Bacillus amyloliquefaciens | (+) | (+) | (+) |

*BDL: Below detection limit

In other experiments, the microbes that were not detected in co-culturing experiments containing all 22 strains (see above) were tested to determine if they could grow together. To that end, the effect of the sequence of inoculation of said microbes (all together vs. anaerobe first vs aerobes first) as well as the dissolved oxygen levels at the time of inoculation and during fermentation, as well as medium composition, were tested. Dissolved oxygen levels were controlled through variation in gas mass transfer using flow and/or agitation rates. Table 8 summarizes the results for the co-culture of C. beijerinckii (strict anaerobe), S. griseus, and B. flexus (strict aerobes). As in previous experiments, detection and evaluation of microbial growth was performed by ddPCR.

TABLE 8

Summary of experimental design and microbial profile in co-culture experiments for C. beijerinckii, S. griseus and B. flexus

| Oxygen levels at the start of fermentation | Aerobic (25% DO) | Aerobic | Anaerobic |
|---|---|---|---|
| Transition when microbial growth reaches OD 1 | Anaerobic (100% N$_2$) | Anaerobic | Aerobic |
| Inoculation | Co-inoculation: C. beijerinckii S. griseus B. flexus | Sequential inoculation: S. griseus B. flexus C. beijerinckii | Sequential inoculation: C. beijerinckii S. griseus B. flexus |

| Microbe | Growth | | |
|---|---|---|---|
| Clostridium beijerinckii | (+) | (+) | (−) |
| Streptomyces griseus | (+) | (+) | (+) |
| Bacillus flexus | (+) | (+) | (+) |

Spinner Flask Bioreactor:

The inoculum containing all 22 microbes was diluted in Extract medium and molasses fermentation proceeded in spinner flasks as described above. The microbial composition was monitored over time using ddPCR. Detected microbes were scored as (+). Microbes that were below the detection limit (BDL) of the ddPCR method were scored as such. The result of the experiment is summarized in Table 9.

TABLE 9

Summary of microbial profile in co-culture experiments of the 22 microbes in spinner flasks over a period of 28 days

| Microbes | Inoculum | Day 7 | Day 14 | Day 21 | Day 28 (End of fermentation) |
|---|---|---|---|---|---|
| Bacillus megaterium | (+) | BDL | BDL | BDL | BDL |
| Lactobacillus casei/paracasei | (+) | (+) | (+) | (+) | (+) |
| Clostridium beijerinckii | (+) | (+) | BDL | BDL | BDL |
| Acetobacter pasteurianus | (+) | (+) | (+) | (+) | (+) |
| Lactobacillus buchneri | (+) | ND | (+) | (+) | (+) |
| Bacillus subtilis | (+) | (+) | (+) | BDL | BDL |
| Paenibacillus cookii | (+) | (+) | (+) | (+) | (+) |
| Lactobacillus vini | (+) | (+) | (+) | (+) | (+) |
| Bacillus licheniformis | (+) | (+) | (+) | (+) | BDL |
| Paenibacillus lautus | (+) | (+) | (+) | (+) | (+) |
| Oceanobacillus oncorhynchi | (+) | (+) | BDL | BDL | BDL |
| Bacillus sp. | (+) | (+) | (+) | (+) | (+) |
| Pseudomonas putida | (+) | (+) | (+) | (+) | (+) |
| Pseudomonas sp. | (+) | BDL | (+) | (+) | (+) |
| Streptomyces griseus | (+) | (+) | (+) | (+) | (+) |
| Paenibacillus chibensis | (+) | (+) | (+) | (+) | (+) |
| Bacillus flexus | (+) | (+) | (+) | (+) | (+) |
| Clostridium pasteurianum | (+) | (+) | (+) | (+) | (+) |
| Azotobacter vinelandii | (+) | BDL | (+) | (+) | (+) |
| Virgibacillus halophilus | (+) | (+) | (+) | (+) | (+) |
| Lactobacillus delbrueckii | (+) | (+) | (+) | (+) | (+) |
| Bacillus amyloliquefaciens | (+) | (+) | BDL | BDL | BDL |

Co-Culture in Commercial Scale Fermenters:

Based on bacteria requirements for optimal co-culture and desired final microbial consortium quality (assessed by ddPCR), aerobic and/or anaerobic bacteria from the groups described above were inoculated into fermenters up to 300 L scale. The final inoculation OD$_{600}$ for each strain was calculated to be between 6.67E-05 to 6.67E-04. Fermentation media included molasses, whey proteins, kelp extract, yeast powder, spirulina, Arabica gum, and sodium chloride. Ammonium hydroxide and phosphoric acid were used as base and acid solutions respectively to maintain pH between pH 5.2 and 7.2. Temperature was controlled between 28° C., and 35° C., and dissolved oxygen was maintained between 0% and 25% during the length of fermentation (up to 3 days). The average microbial composition in fermentation products is summarized in Table 10.

TABLE 10

Average microbial composition in fermentation products

| Microbes | Average number of bacteria per strain in 1 mL of final fermentate |
|---|---|
| B. megaterium | 2.02E+06 |
| L. casei/paracasei | 1.77E+08 |
| C. beijerinckii | 1.53E+07 |
| A. pasteurianus | 4.99E+04 |
| L. buchneri | 2.37E+06 |
| B. subtilis | 1.96E+06 |
| P. cookie | 1.79E+07 |
| L. vini | 2.46E+06 |
| B. licheniformis | 7.08E+05 |
| P. lautus | 8.43E+06 |
| O. oncorhynchi | 1.18E+06 |
| B. amyloliquefaciens | 9.22E+06 |
| Bacillus sp. | BDL |
| P. putida | 2.68E+09 |
| Pseudomonas sp. | 1.62E+09 |
| S. griseus | 7.51E+03 |
| P. chibensis | 1.13E+06 |
| B. flexus | 7.83E+04 |
| C. pasteurianum | 1.05E+07 |
| A. vinelandii | 1.13E+06 |
| V. halophilus | BDL |
| L. delbrueckii | 3.64E+07 | n = 16, anaerobic;
n = 10, aerobic
BDL—below detection limit

Analysis of the Viable Microbial Load by Spread-Plating Under Aerobic and Anaerobic Conditions.

Analysis of the microbial count was conducted using a spread-plating methodology to determine the colony forming units (CFU) in the sample(s). All samples were stored at room temperature in light and air tight containers. After vigorous mixing of the sample to ensure the contents were evenly dispersed, 1 mL was retained. From this aliquot, 0.1 mL was aseptically collected and mixed with 9.9 mL of sterile water in a culture tube ($10^{-2}$ dilution). The tube was then vortexed (e.g., 60 seconds at 2000 rpm) and 10 fold serial dilutions prepared in water (up to $1:10^9$ dilution). One hundred microliters of each dilution was subsequently spread on semi-solid media in 100 mm Petri plates using a sterile L-shaped spreader. Plates containing industry standard media such as Standard Method Agar (SMA; BD #247940), Nutrient Agar (NA; BD #213000) were used. The inoculated plates were then incubated in temperature controlled chambers at 22° C. to 35° C. For evaluation of anaerobic microbe counts, plates were first placed in anaerobic boxes (e.g. BD GasPak™ EZ Container Systems, BD Diagnostics) before incubation at the desired temperature(s). In some instances, the aliquot to be tested was first incubated in sterile peptone water for a period of up to 3 days at temperatures up to 35° C. prior to performing serial dilutions and plating as described above. Post-incubation, all colonies on selected plates were counted using a colony counter such as Quebec® Dark-Field Colony Counter (Reichert) and CFU/mL were calculated. Plating showed up to 1.1E+09 CFU/mL under aerobic and anaerobic conditions.

Example 3

Identification of Microbial Metabolic Activity Potential

Salt Tolerance Assay:

All strains in the microbial consortium demonstrated acceptable growth in laboratory-grade Yeast Peptone Dextrose medium (YPD, Difco 242820). This medium was therefore used to determine the salt tolerance of each isolate using variable amounts of sodium chloride (a standard for salt-tolerance testing) up to 5% w/v. Each isolate was cultured in 2 ml of medium under ideal growth conditions: 30° C. with agitation (125-175 rpm) for aerobes and 35° C. with no agitation for anaerobes in anaerobic chambers (BD diagnostics). At 24, 48, and 72 hours, growth was recorded for each culture based on the general equivalence to Mac-Farland standards (available on the World Wide Web at pro-lab.com/inserts/McFarland.pdf). Any isolate showing growth at 5% NaCl at 72 hours was recorded as having a NaCl tolerance≥25%, growth at 2.5% is ≥22.5% and so on.

Nitrogen (N) Fixation Assay:

Nitrogen-free semi-solid medium containing sucrose 5.0 g/L, $MgSO_4$ 0.2 g/L; $KH_2PO_4$ 0.8 g/L; $FeSO_4$ 0.04 g/L; $Na_2MoO_4$; 0.005 g/L, $CaCO_3$ 2 g/L and 15 g/L Agar was prepared and sterilized by autoclaving. From a master culture plate, a single colony of each isolate was transferred to a N-free plate aseptically. Using the streaking-out method, colonies were spread onto fresh N-free plates. Growth conditions varied based on the isolate: anaerobic/microaerophilic bacteria were incubated at 35° C. in anaerobic chambers, while aerobic bacteria were incubated at 30° C. Incubation times extended up to 1 week before scoring for growth. Only robust nitrogen fixers (e.g., robust growth) were scored as positive.

Calcium Salt Solubilization Assay:

Calcium carbonate semi-solid medium containing $MgSO_4$ 0.3/L; $CaCl_2$ 01 g/L; $FeSO_4$ 0.12 g/L; $K_2SO_4$ 1 g/L; Sucrose 20 g/L; $Na_2MoO_4$ 0.01 g/L; $MnCl_2$ 0.01 g/L; yeast extract 5 g/L; peptone 10 g/L; $CaCO_3$ 2 g/L; agar 15 g/L was prepared and sterilized by autoclaving. From a master culture plate, a single colony of each isolate was transferred to a carbonate plate, aseptically. A single streak was drawn down the middle of the plate. Growth conditions varied based on the isolate: anaerobic/microaerophilic bacteria were incubated at 35° C. in anaerobic chambers, while aerobic bacteria were incubated at 30° C. Incubation times extended up to 1 week before scoring for the presence of a clearing area adjacent to the bacteria. Only obvious clearing of the $CaCO_3$ precipitate was scored as positive.

Phosphate Salt Solubilization Assay:

Calcium Phosphate semi-solid medium containing $MgSO_4$ 0.3/L; $CaCl_2$ 01 g/L; $FeSO_4$ 0.12 g/L; $K_2SO_4$ 1 g/L; Sucrose 20 g/L; $Na_2MoO_4$ 0.01 g/L; $MnCl_2$ 0.01 g/L; yeast extract 5 g/L; peptone 10 g/L; $Ca_3(PO_4)_2$ 5 g/L; agar 15 g/L was prepared and sterilized by autoclaving. From a master culture plate, a single colony of each isolate was transferred to a carbonate plate, aseptically. A single streak was drawn down the middle of the plate. Growth conditions varied based on the isolate: anaerobic/microaerophilic bacteria were incubated at 35° C. in anaerobic chambers, while aerobic bacteria were incubated at 30° C. Incubation times extended up to 1 week before scoring for the presence of a clearing area adjacent to the bacteria. Only obvious clearing of the calcium phosphate precipitate was scored as positive.

Zinc Salt Solubilizing Assay:

To test strains for the ability to solubilize zinc, four types of zinc were utilized in the assay: $Zn_5(CO_3)_2(OH)_6$ (zinc carbonate hydroxide). $Zn_3(PO_4)_2$ (zinc phosphate), ZnO (zinc oxide), and $ZnSO_4$ (zinc sulfate). Each type of zinc was then added at 0.2% (w/v) to either Brain-Heart Infusion (BHI) or YPD agar media. For each strain, a single colony was then selected and streaked out onto both semi-solid media in Petri dishes. Aerobes were incubated at 30° C., and anaerobes were incubated at 35° C. in a static incubator for 3 days. Plates were checked after 24, 48 and 72 hours for signs of clearing in the medium, which is interpreted as a positive indicator of zinc-solubilization.

Iron Mobilizing Analysis:

A number of soil microbes produce so-called siderophores in environments with low concentrations of iron—an essential micronutrient. These compounds form water soluble complexes with $Fe^{3+}$, which can be released in situations of iron deficiency. Both bacteria siderophores benefit both plants and microbes as a localized source of iron. Whole-genome sequences analysis for each of the 22 isolates was performed focusing on the detection of genes coding for the siderophores, siderophore biosynthesis pathway(s) as well as siderophore receptors and transporters such as Yus, Yfh, Yfi, Asb, Fur, TonB, ExbB, ExbD, Citrate, Desferrioxamine, Deferoxamine, Ferrichrome, Fusarinine, Ornibactin, Chrysobactin, Vibriobactin, Mycobactin, Pyoverdin, Pyochelin, Yersiniabactin, Enterobactin, Achromobactin, Acinetobactin, Azotobactin, Bacillibactin, and Anguibactin. This enabled determination of whether not a given microbe possessed the metabolic arsenal to perform to produce and/or transport iron mobilizing compounds.

Analysis of Microbial Organic Matter Dephosphorylation Potential:

Bacteria can release a range of microbial enzymes which through there action on organic matter, can produce phosphate forms accessible by plants. These enzymes include non-specific phosphatases that dephosphorylate phosphoester and/or phosphoanhydride bonds in organic matter, phytases that release phosphorus from phytic acid and phosphonatases and C—P lyases that dissociate C—P bonds in organophosphonates. Whole-genome sequence analysis for each of the 22 isolates was performed focusing on the detection of genes coding for these enzymes in functional metabolic pathways. This enabled determination of whether or not a given microbe possessed the enzymatic arsenal to perform the dephosphorylation of organic matter in the soil.

Chitinase Assay:

Colloidal chitin plate assays were performed essentially as described by Hsu and Lockwood (*Applied Microbiology*, 29:422-426, 1975). Bacteria colonies (1-3 days old) picked from master plates were streaked on colloidal chitin plates (semi-dry chitin, 5 g/L; $K_2HPO_4$, 0.7 g/L; $KH_2PO_4$, 0.3 g/L; $MgSO_4.5H_2O$, 0.5 g/L; $FeSO_4.7H_2O$, 0.01 g/L; $ZnSO_4$, 0.001 g/L; $MnCl_2$, 0.001 g/L and agar, 15 g/L). Plates were incubated for up to 1 week at 30° C. for aerobes or at 35° C. under anaerobic conditions for anaerobes. Chitinase positive isolates were identified by clearing in the medium and/or significant microbial growth.

Cellulase Assay:

The Deoxymethyl Cellulose Plate Assay was adapted from Alves et al. (*The Open Microbiology Journal*, 8:25-31, 2014). In brief, bacteria colonies (1-3 days old) picked from master plates were streaked on semi-solid medium (Deoxymethyl cellulose, 0.5% w/v; agarose 1.5% w/v; Tris-HCl, 50 mM pH 6.8; $CaCl_2$, 1 mM). Bacteria isolates were subsequently incubated at 30° C. for aerobes, 35° C. under anaerobic conditions for anaerobes for up to 1 week. Each plate was subsequently treated with a solution of Congo Red (0.25% w/v in 0.1M Tris-HCl pH 8.0) and destained with NaCl 0.5% w/v in 0.1 M Tris-HCl, pH 8.0. Cellulase positive isolates were identified by clearing in the medium and/or significant microbial growth.

Indole-3-Acetic Acid (IAA) Production Assay:

IAA assay was conducted on each microbial isolate grown in liquid media supplemented with 1-5 mg/mL of Tryptophan. Seven to fourteen days post inoculation, the cultures were tested for IAA production using Salkowski's reagent as described in Glickmann et al. (*Applied and Environmental Microbiology*, February 1995, p 793-796). Briefly, clarified spent medium from each culture was mixed with Salkwoski's reagent at a ratio of 1:1. After 30 min incubation, the absorbance at 540 nm was measured. Assessment of IAA production was conducted using a previously prepared standard curve using purified IAA (Alfa-Aesar, Tewksbury, Mass. USA). In addition, whole-genome sequence analysis for each of the 22 isolates was performed focusing on the detection of the auxin biosynthesis pathways.

Other Metabolic Assays:

For additional metabolic activities including denitrification assays, urease production, and malic acid assimilation, bioMérieux's API® identification products were used according to the manufacturer's recommendations (bioMérieux, Inc., Durham, N.C. USA).

The results of key metabolic activity profiling are shown in Table 11.

TABLE 11

Metabolic activities of microbial isolates

| Microbes | Nitrogen metabolism | Salt tolerant | Mineral salt solubilization | Cellulolytic/ chitinolytic | Other Plant Beneficial Activity | Iron metabolism |
|---|---|---|---|---|---|---|
| *Acetobacter pasteurianus* | Denitrification | ≤1% | Zn | | Indole production (IAA) | Iron mobilizing |
| *Azotobacter vinelandii* | Denitrification + $N_2$ fixation | <2.5% | | | IAA | Iron mobilizing |
| *Bacillus megaterium* | Denitrification + $N_2$ fixation | ≥5% | | | Malic Acid assimilation | Iron mobilizing |
| *Bacillus subtilis* | Denitrification + $N_2$ fixation | ≥5% | | Cellulose degradation | Malic Acid assimilation + IAA | Iron mobilizing |
| *Bacillus licheniformis* | Denitrification + $N_2$ fixation | ≥5% | | Chitin degradation | Malic Acid assimilation + IAA | Iron mobilizing |
| *Oceanobacillus oncorhynchi* | Denitrification | ≥5% | | | IAA | Iron mobilizing |
| *Bacillus amyloliquefaciens* | Denitrification + $N_2$ fixation | ≥5% | | Cellulose degradation | Malic Acid assimilation + IAA | Iron mobilizing |
| *Bacillus sp.* | Denitrification | ≥5% | | | Malic Acid assimilation + IAA | Iron mobilizing |
| *Bacillus flexus* | $N_2$ fixation | ≥5% | | Cellulose degradation | Malic Acid assimilation + IAA | Iron mobilizing |
| *Virgibacillus halophilus* | Denitrification + urease production | | | | | |
| *Clostridium beijerinckii* | $N_2$ fixation | <2.5% | P, Ca & Zn solubilization | | | Iron mobilizing |
| *Clostridium pasteurianum* | $N_2$ fixation | ≤2.5% | P, Ca & Zn solubilization | | | |
| *Lactobacillus casei/paracasei** | | ≥5% | P, Ca & Zn solubilization | | IAA | |
| *Lactobacillus buchneri* | | ≤2.5% | P & Ca solubilization | | | Iron mobilizing |
| *Lactobacillus vini* | | <2.5% | P & Ca solubilization | | | |
| *Lactobacillus delbrueckii* | | ≤2.5% | P, Ca & Zn solubilization | | | |

TABLE 11-continued

Metabolic activities of microbial isolates

| Microbes | Nitrogen metabolism | Salt tolerant | Mineral salt solubilization | Cellulolytic/ chitinolytic | Other Plant Beneficial Activity | Iron metabolism |
|---|---|---|---|---|---|---|
| Paenibacillus cookii | Denitrification + N$_2$ fixation | ≤2.5% | | | Malic Acid assimilation + IAA | Iron mobilizing |
| Paenibacillus lautus | Denitrification | ≥5% | P & Ca solubilization | Chitin degradation | Malic Acid assimilation | Iron mobilizing |
| Paenibacillus chibensis | | <5% | | | Malic Acid assimilation + IAA | Iron mobilizing |
| Pseudomonas putida | | ≥5% | Zn | | Malic Acid assimilation + IAA | Iron mobilizing |
| Pseudomonas sp. | Denitrification | ≥5% | Zn | | Malic Acid assimilation + IAA | Iron mobilizing |
| Streptomyces griseus | Denitrification + N$_2$ fixation | ≥5% | | Chitin & Cellulose degradation | Malic Acid assimilation + IAA | Iron mobilizing |

Example 4

Evaluation of Plant Growth Promoting Activity

Cucumber seeds purchased from The Seed Kingdom were pre-germinated for 4 days at 22-24° C. in a temperature and humidity controlled growth chamber (Sheldon Manufacturing, Inc. Cornelius, Oreg.). Pre-germination was performed in rolled germination paper (Anchor Paper, Saint Paul, Minn.) impregnated with a dilute mixture of liquid fertilizer (50 ppm of 20-20-20 NPK (Grow More, Gardena. Calif.) in water) and Agrinos microbial consortium (AMC) product ranging from 1:1,000 to 1:2,000. AMC product is the liquid product obtained from co-cultivation of the 22 microbes listed in Table 10 using the commercial scale co-culture described in Example 2.

Figure 2:
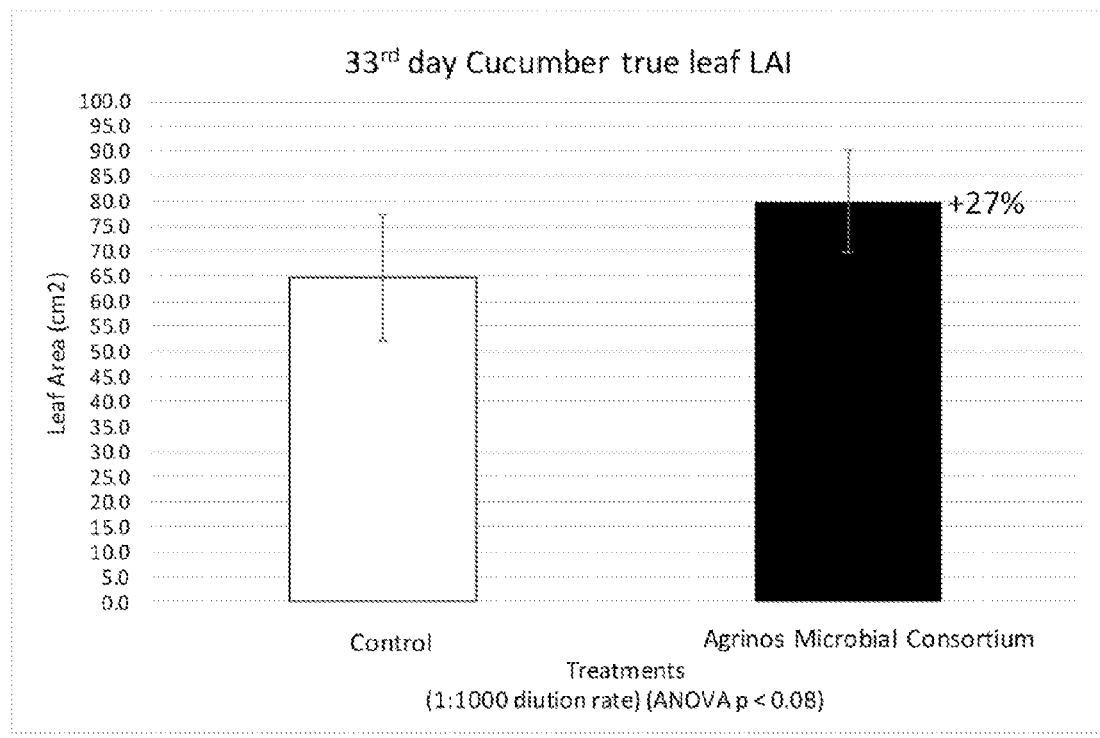
FIG. 2 is a graph showing day 33 Leaf Area Index (LAI) of the terminal true leaf of cucumber plants treated as indicated.

Staged and synchronized plantlets were then transplanted into prepared potting soil growth medium (Sunshine Mix) pre-treated with fertilizer and the microbes. Pre-treatment of potting soil consisted of diluted mixtures of liquid fertilizer (50 ppm NPK) and AMC product ranging from 1:1000 to 1:2000. For each treatment, 17-18 plants were used. Pots were randomized in flats in defined growth conditions: 16-24° C., and 12 hours photoperiod. The flats were watered 2 to 3 times a week with 50 ppm NPK. After 33 days, the Leaf Area Index (LAI) of the terminal true leaf of each plant was measured (FIG. 2). The data was analyzed by One-way ANOVA (Analysis Of Variance) to compare samples within the experiment.

Example 5

Evaluation of Activity in Crops

This Example describes particular methods for assessing activity of the disclosed compositions in crops such as corn, tomato, and cabbage. However, one skilled in the art will appreciate that methods that deviate from these specific methods can also be used to assess the activity of the compositions.

Figure 3:
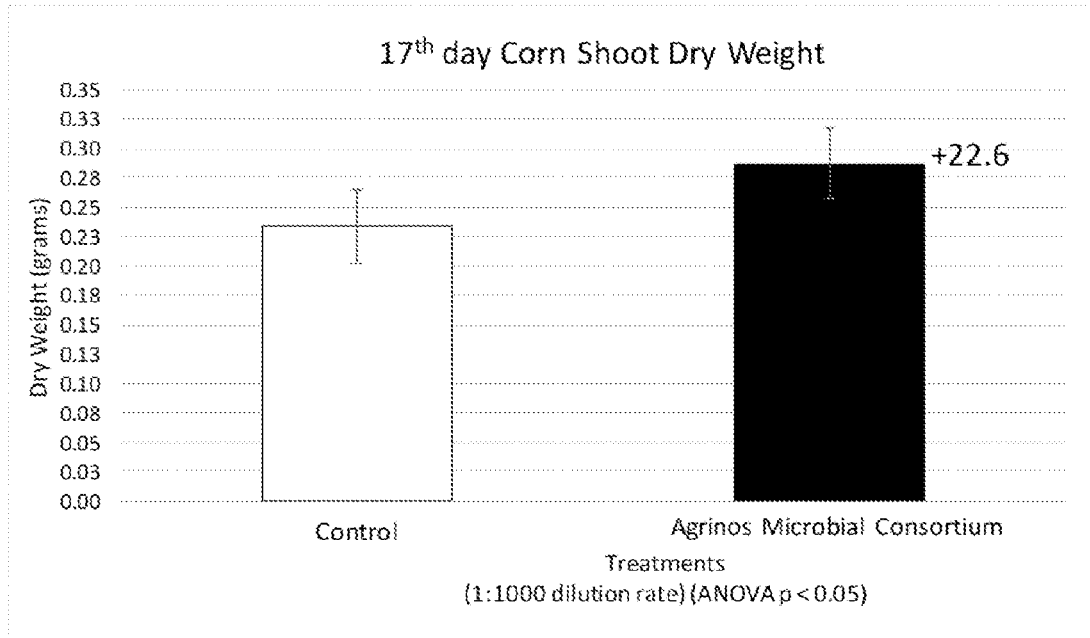
FIG. 3 is a graph showing corn day 17 shoot dry weight with the indicated treatments.

Corn Assay (Growth Room):

Corn seeds (Alberta Lea Seeds, Albert Lea, Minn.) were soaked in water for 4 hrs at room temperature before planting in potting soil or soilless growth medium (Sunshine Mix) pre-treated with fertilizer and the AMC product as follows: Modified Hoagland solution (P, 30.97 ppm; K, 39.1 ppm; Ca, 40.0 ppm; Mg, 14.59 ppm; S, 20.143 ppm; Fe, 1.010 ppm; Cu, 0.019 ppm; Co, 0.012 ppm; B, 2.44 ppm; Mn, 0.494 ppm; Mo, 0.001 ppm and Zn, 0.056 ppm) and 1:1,000 dilution of AMC product. At seed planting, 100 mg of a slow release Urea formulation was added to the soil. Trays with 8 to 9 pots were incubated in the dark for 3 days at 25° C. in a temperature and humidity controlled growth chamber (Sheldon Manufacturing, Inc. Cornelius, Oreg.). The plants were then grown for 13 to 16 days in growth room conditions: 16-24° C., and 12 hours photoperiod. Watering was performed 2 to 3 times per week with modified Hoagland solution. Dry shoot weights were subsequently determined after 4 days of drying at 75° C. (FIG. 3). Data were analyzed by One-way ANOVA (Analysis Of Variance).

Field Tomato Trials:

Tomato variety Sun 6366 was transplanted into 6 m×1.8 m size bedded plots with additional water at transplanting. The field was fertilized prior to transplanting with 201 kg N/ha and 224 kg P$_2$O$_5$ and K$_2$O/ha. Two split applications of AMC were applied to the tomatoes in each plot. The first application occurred after the field was transplanted. AMC was applied through drip irrigation (TTAPE, 20 cm spacing between emitters) at a 1 L/acre rate. The second application of AMC was directly injected and applied 36 days after transplanting together with N fertilizer in the form of UAN 28 at the rate of 38 L/acre. Control plots were treated exactly the same as experimental except that no AMC was used during the cultivation process.

Figure 4:
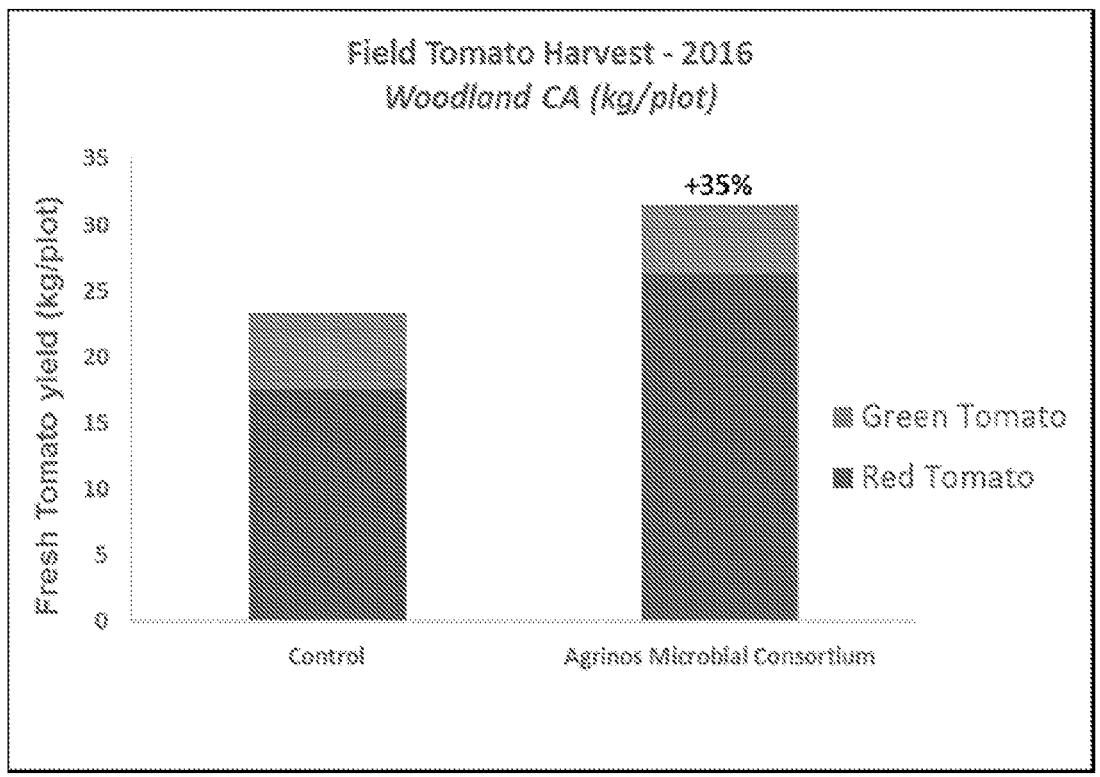
FIG. 4 is a graph showing tomato yield (green and red tomato) with the indicated treatments.

Tomato stands were managed to have equal plant populations. Tomatoes were harvested by hand 2 months after the last AMC application. A total of 6 plants were harvested from a 3.35 m$^2$ area in the center of the plot. Tomato yield and quality (Green versus Red) were recorded. Weights were recorded and analyzed using XCELSTAT2016.4 (Addinsoft Inc.) (FIG. 4).

Field Corn Trials:

Maize variety Mycogen 2H723 (Mycogen Seeds, Indianapolis, Ind.) was planted into a 4-row configuration with 75 cm between rows and rows 6.1 m long. The field was fertilized prior to transplanting with 201 kg N/ha and 224 kg P$_2$O$_5$ and K$_2$O/ha. Two split applications of AMC were applied in each plot. The first application occurred after the field was planted. AMC was applied with backpack sprayer at a 1 L/acre rate and water was applied into the soil using drip irrigation (TTape, 20 cm emitters). Irrigation water was restricted to 75% of normal levels in this study. Water restrictions were imposed for 5 weeks leading up to full flowering. The second AMC application was directly injected and applied 35 days after planting. Control Maize plots received additional N fertilizer at the time of injection in the form of UAN 28 at the rate of 38 L/acre rate=33 kg N/ha rate for a total of 234 kg N/ha over the course of the study. The AMC plots did not receive additional N and ended up with 201 kg N/ha. Soil pH is high in in the area of the field and averages 8.1.

Figure 5:
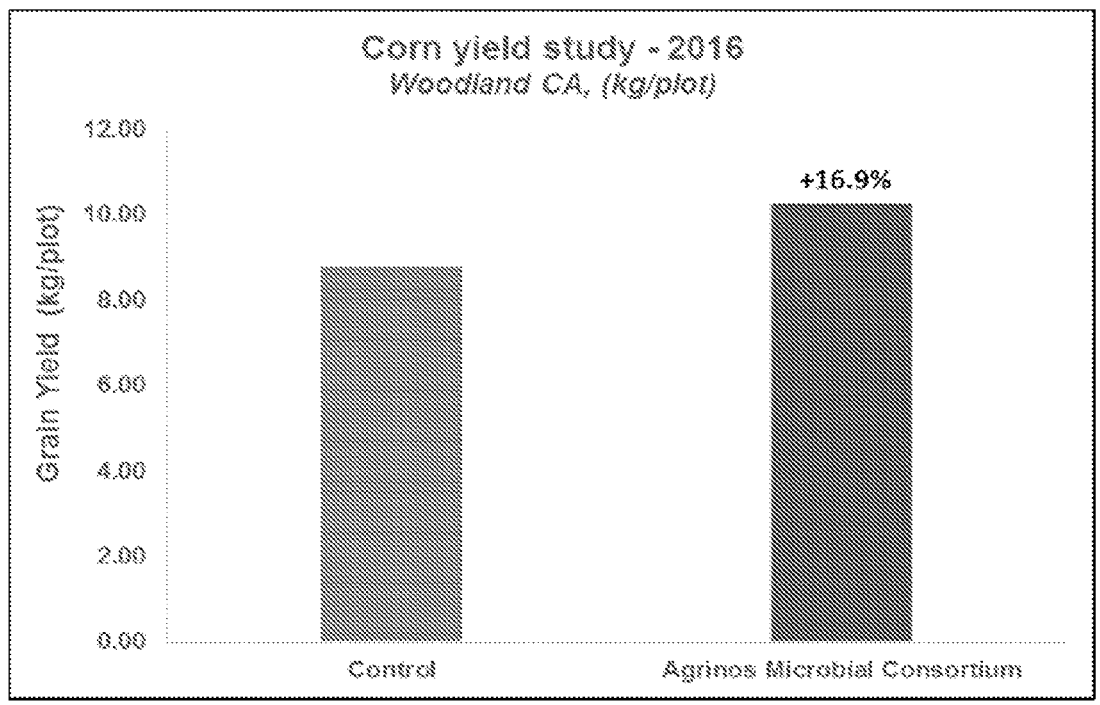
FIG. 5 is a graph showing corn yield with the indicated treatments.

Maize stands were thinned to a plant population of 34,000 plants to assure equal plant populations. Maize was harvested by a corn harvester 5 months after planting. Only the center 2 rows were harvested from the 4 row plots representing 9.3 m² area in the center of the plot, which provided plenty of border plants around the harvested area. Maize grain was dried to a 15% moisture over several days weighed. Grain weights were recorded and analyzed using XCELSTAT2016.4 (Addinsoft Inc) (FIG. 5).

Field Cabbage Trials:

Cabbage variety Golden Acres was planted as seed into 4 row bedded plots 12 feet long by 11 feet wide. The field was fertilized prior to planting with 20 gallons/acre 25-7-0-3 S in a double-row 16 inches apart from the center of the bed. Additional fertilizer was applied as a side dress application using UAN (32% N) at 10 gallons/acre resulting in 90 lb N, 15 lbs P, 0 lbs K and 6.5 lbs S/acre rate. AMC product was applied at 1 L/acre rate in the furrow at planting and in the case of treatment 2, a second application of AMC (1 L/acre rate) was applied 42 days after planting. The field was furrow irrigated 4 times with a range of irrigation of 6.3 to 8.9 acre inch of water/irrigation for a total of 29.7 acre inches. Rainfall supplied an additional 10.7 inches during the life of the crop. The crop was sprayed with a variety of insecticides, herbicides and fungicides to protect the cabbages from biotic stresses. Soil pH was 8.0

Figure 6:
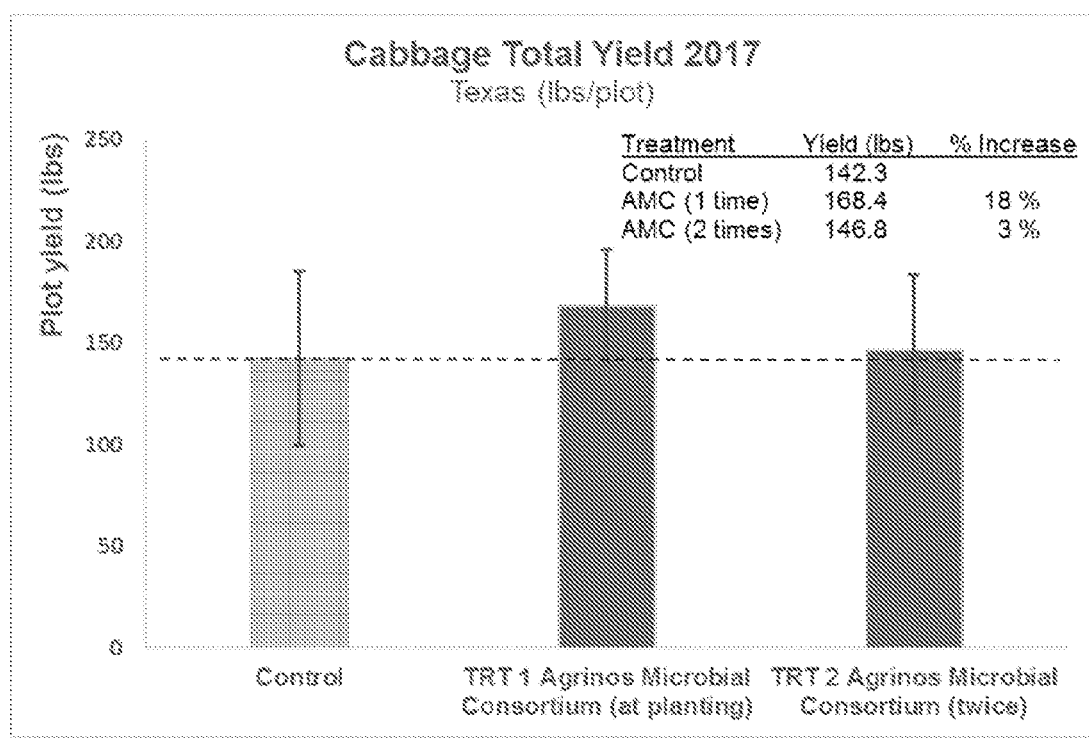
FIG. 6 is a graph showing total cabbage yield with the indicated treatments.

Cabbages had equal stand count populations and were harvested one time 95 days after sowing. All plants in the middle 2 rows of the plot were harvested from an effective harvest plot of 220 ft². Heads were then graded into size 24 and 18 categories and weighed. Graded weights and total weights were analyzed using XCELSTAT2016.4 (Addinsoft Inc.) (FIG. 6).

Example 6

Root Assays

Commodity crop seeds such as but not limited to corn and tomato are pre-germinated for 3 days at 22-24° C. in a temperature and humidity controlled growth chamber (Sheldon Manufacturing, Inc. Cornelius, Oreg.). Pre-germination is performed in rolled germination paper (Anchor Paper, Saint Paul, Minn.) impregnated with a dilute mixtures of liquid fertilizer (25-100 ppm of 20-20-20 NPK (Grow More, Gardena, Calif.) in water) and AMC product ranging from 1:1000 to 1:5000. Staged and synchronized plantlets are transplanted in pre-treated soilless medium such as sand, rockwool, vermiculite or other inert matrices. Pre-treatment of the growth medium consists of diluted mixtures of hydroponic nutrient solution such as Hoagland's Complete Nutrient Solution (Hoaglund and Amon, *The Water-Culture Method for Growing Plants Without Soil*, 1938) and AMC product ranging from 1:1000 to 1:5000. At least 12 plants of each treatment including control plants, are randomized in support trays. The plants are grown in standard greenhouse conditions for up to 45 days. Root anatomy and morphology are analyzed upon completion of the experiments.

Example 7

Viability of Freeze-Dried Microbes

Freeze Drying:

Individually cultured or co-cultured microbes in optimal media (Table 12) were subjected to freeze-drying in order to evaluate viability. Briefly, for mono-cultures, microbes were grown at 30-35° C. under constant agitation (200 rpm) in temperature controlled incubator in 5 mL culture volumes for 24 hours, under either anaerobic or aerobic conditions. For co-culture experiments, microbes were grown in 2 L DASGIP bioreactors (Eppendorf North America Hauppauge, N.Y.) using medium containing 2% w/v molasses, 0.1% w/v whey powder, 0.25% w/v Ferti-Nitro Plus Plant N (Ferti-Organic, Brownsville, Tex. USA), 0-4% w/v NaCl, 0.02% KCl, 0.115% w/v $Na_2HPO_4$ and 0.02% $KH_2PO_4$; pH 5.7-7.0 at 30-35° C. Anaerobic groups were grown in the absence of oxygen.

Optical density was determined for each culture at 600 nm. Each culture was subsequently mixed with mannitol/lyoprotectant solution (OPS Diagnostics Lebanon, N.J., USA) as per manufacturer's recommendation and the microbial suspension was aliquoted into lyophilization vials (OPS Diagnostics, Lebanon, N.J., USA) which were filled ⅓-⅕ the volume and then fitted with a split stopper. After 60 minutes at −80° C., the vials were placed in the FreeZone 6 freeze dry system (Labconco, Kansas City, Mo.), vacuum was applied, and the water in the samples was allowed to sublimate overnight (0.04 mBa, −50° C.). After freeze drying, the split stoppers were lowered into the vials and were further secured with an aluminum band crimped in place. Samples were stored at 4° C. until needed.

TABLE 12

Media used for growth of individual microbes.

| Microorganisms | Growth media |
| --- | --- |
| *Acetobacter pasteurianus* | YPD, MP, M-HYTA |
| *Azotobacter vinelandii* | RhX, MP, M-HYTA |
| *Bacillus amyloliquefaciens* | YPD, MP, YPDS, M-HYTA |
| *Bacillus flexus* | BHI, MP, M-HYTA, NA, YPD |
| *Bacillus licheniformis* | BHI, MP, M-HYTA |
| *Bacillus megaterium* | YPD, MP, YPDS, M-HYTA |
| *Bacillus* sp. | BHI, MP, M-HYTA, YPD |
| *Bacillus subtilis* | BHI, MP, M-HYTA, YPD |
| *Clostridium beijerinckii* | RCM, MP, M-HYTA |
| *Clostridium pasteurianum* | RCM, MP, M-HYTA, |
| *Lactobacillus buchneri* | RCM, MRS, MP, M-HYTA |
| *Lactobacillus casei/paracasei* | RCM, MRS, MP, M-HYTA |
| *Lactobacillus delbrueckii* | RCM, MRS, MP, M-HYTA |
| *Lactobacillus vini* | RCM, MRS, MP, M-HYTA |
| *Oceanobacillus oncorhynchi* | BHI, MP, BHIS, M-HYTA |
| *Paenibacillus chibensis* | BHI, MP, M-HYTA, |
| *Paenibacillus cookii* | BHI, MP, M-HYTA |
| *Paenibacillus lautus* | BHI, MP, M-HYTA |
| *Pseudomonas putida* | YPD, MP, YPDS, M-HYTA |

TABLE 12-continued

Media used for growth of individual microbes.

| Microorganisms | Growth media |
|---|---|
| *Pseudomonas* sp. | YPD, MP, YPDS, M-HYTA |
| *Streptomyces griseus* | YPD, MP, YPDS, M-HYTA |
| *Virgibacillus halophilus* | BHI, MP, BHIS, M-HYTA, YPD |

YPD: yeast peptone dextrose (BD #242720),
YPDS: YPD + 8 g/L NaCl,
RCM: reinforce *clostridium* medium (BD#218081),
BHI: Brain Heart Infusion Broth (HiMedia, # LQ077),
BHIS: BHI + 45 g/L NaCl,
RhX: ATCC Medium: 111 *Rhizobium* X Medium,
MRS: *Lactobacilli* MRS (BD# 288210);
M-HYTA: Molasses, whey proteins, kelp extract, yeast powder, *spirulina*, and NaCl To evaluate the viability, each freeze-dried culture was rehydrated and the growth potential determined. Fresh medium was inoculated with rehydrated culture at an $OD_{600}$ of 0.1. Growth was monitored over a period of 3 days. As control, non-lyophilized cultures were used. The results are summarized in Table 13.

TABLE 13

Microbial growth following freeze-drying and rehydration

| | Growth | |
|---|---|---|
| Microorganism | Control | Freeze-dried[a] |
| *Acetobacter pasteurianus* | (+++) | (++) |
| *Azotobacter vinelandii* | (+++) | (+) |
| *Bacillus amyloliquefaciens* | (+++) | (++) |

TABLE 13-continued

Microbial growth following freeze-drying and rehydration

| | Growth | |
|---|---|---|
| Microorganism | Control | Freeze-dried[a] |
| *Bacillus flexus* | (+++) | (+++) |
| *Bacillus licheniformis* | (+++) | (++) |
| *Bacillus megaterium* | (+++) | (+++) |
| *Bacillus* sp. | (+++) | (+++) |
| *Bacillus subtilis* | (+++) | (+++) |
| *Clostridium beijerinckii** | (+++) | (++) |
| *Clostridium pasteurianum** | (+++) | (+) |
| *Lactobacillus buchneri** | (+++) | (+++) |
| *Lactobacillus delbrueckii** | (+++) | (++) |
| *Lactobacillus paracasei (casei)** | (+++) | (++) |
| *Lactobacillus vini** | (+++) | (+++) |
| *Paenibacillus cookii* | (+++) | (+++) |
| *Paenibacillus lautus* | (+++) | (++) |
| *Paenibacillus chibensis* | (+++) | (++) |
| *Pseudomonas putida* | (+++) | (+++) |
| *Pseudomonas* sp. | (+++) | (+) |
| *Streptomyces griseus* | (+++) | (+++) |
| *Oceanobacillus oncorhynchi* | (+++) | (+++) |
| *Virgibacillus halophilus* | (+++) | (+++) |

[a](+) indicates growth after freeze drying.
*Grown anaerobically.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method comprising contacting soil, plants, plant parts, or seeds with a composition consisting of cells of microbial species of each of *Lactobacillus delbrueckii*, *Virgibacillus halophilus*, *Azotobacter vinelandii*, *Clostridium pasteurianum*, *Paenibacillus chibensis*, *Streptomyces griseus*, *Pseudomonas* sp., *Pseudomonas putida*, *Bacillus* sp., *Bacillus amyloliquefaciens*, *Oceanobacillus oncorhynchi*, *Paenibacillus lautus*, *Bacillus licheniformis*, *Lactobacillus vini*, *Paenibacillus cookii*, *Bacillus subtilis*, *Lactobacillus buchneri*, *Bacillus megaterium*, *Acetobacter pasteurianus*, *Clostridium beijerinckii*, *Lactobacillus casei/paracasei*, and *Bacillus flexus* in a liquid medium.

2. The method of claim 1, further comprising contacting the soil, plants, plant parts, or seeds with one or more of chitin, chitosan, glucosamine, and amino acids.

3. The method of claim 1, further comprising contacting the soil, plants, plant parts, or seeds with one or more of HYT B, HYT C, and HYT D.

4. The method of claim 1, further comprising contacting the soil, plants, plant parts, or seeds with a liquid fertilizer.

5. The method of claim 1, further comprising contacting the soil, plants, plant parts, or seeds with one or more pesticides, one or more fungicides, one or more herbicides, one or more insecticides, one or more plant hormones, one or more plant elicitors, or combinations of two or more thereof.

6. The method of claim 1, further comprising activating the microbial species in the composition prior to contacting the soil, plants, plant parts, or seeds with the composition.

7. The method of claim 1, comprising contacting the soil with the composition to produce treated soil and cultivating seeds, seedlings, or plants in the treated soil.

8. A method comprising contacting soil, plants, plant parts, or seeds with a composition consisting of cells of microbial species with 16S rDNA sequences having at least 99% sequence identity to each of SEQ ID NOs: 3-24 in a liquid medium.

9. A method comprising contacting soil, plants, plant parts, or seeds with a composition consisting of American Type Culture Collection deposit number PTA-123288 and PTA-123289 in a liquid medium.

10. The method of claim 8, wherein the composition consists of cells of microbes with 16S rDNA sequences of each of SEQ ID NOs: 3-24 in the liquid medium.

* * * * *